United States Patent
Van Den Brink et al.

(10) Patent No.: US 11,597,979 B2
(45) Date of Patent: Mar. 7, 2023

(54) METHODS AND COMPOSITIONS FOR DETECTING RISK OF CANCER RELAPSE

(71) Applicant: MEMORIAL SLOAN-KETTERING CANCER CENTER, New York, NY (US)

(72) Inventors: Marcel Van Den Brink, New York, NY (US); Robert Jenq, New York, NY (US); Jonathan U. Peled, Roosevelt Island, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 1235 days.

(21) Appl. No.: 15/756,845

(22) PCT Filed: Sep. 2, 2016

(86) PCT No.: PCT/US2016/050269
§ 371 (c)(1),
(2) Date: Mar. 1, 2018

(87) PCT Pub. No.: WO2017/041039
PCT Pub. Date: Mar. 9, 2017

(65) Prior Publication Data
US 2018/0274036 A1    Sep. 27, 2018

Related U.S. Application Data

(60) Provisional application No. 62/298,258, filed on Feb. 22, 2016, provisional application No. 62/265,327, filed on Dec. 9, 2015, provisional application No. 62/214,604, filed on Sep. 4, 2015.

(51) Int. Cl.
| | |
|---|---|
| C12Q 1/6886 | (2018.01) |
| A23L 33/135 | (2016.01) |
| A61K 35/74 | (2015.01) |
| C12N 1/20 | (2006.01) |
| A61K 35/28 | (2015.01) |
| C12Q 1/689 | (2018.01) |
| A61P 35/00 | (2006.01) |
| A61K 9/00 | (2006.01) |
| A61K 35/741 | (2015.01) |
| A61K 38/16 | (2006.01) |
| A61K 45/06 | (2006.01) |
| C12R 1/01 | (2006.01) |

(52) U.S. Cl.
CPC .......... *C12Q 1/6886* (2013.01); *A23L 33/135* (2016.08); *A61K 9/0031* (2013.01); *A61K 9/0043* (2013.01); *A61K 9/0053* (2013.01); *A61K 35/28* (2013.01); *A61K 35/74* (2013.01); *A61K 35/741* (2013.01); *A61K 38/164* (2013.01); *A61K 45/06* (2013.01); *A61P 35/00* (2018.01); *C12N 1/20* (2013.01); *C12N 1/205* (2021.05); *C12Q 1/689* (2013.01); *A23V 2002/00* (2013.01); *C12Q 2600/158* (2013.01); *C12R 2001/01* (2021.05)

(58) Field of Classification Search
None
See application file for complete search history.

(56) References Cited

U.S. PATENT DOCUMENTS

| | | | |
|---|---|---|---|
| 2006/0172330 | A1 | 8/2006 | Osborn et al. |
| 2014/0135398 | A1 | 5/2014 | Matar et al. |
| 2015/0011415 | A1 | 1/2015 | Levin et al. |
| 2015/0093360 | A1 | 4/2015 | McKenzie et al. |

FOREIGN PATENT DOCUMENTS

| | | |
|---|---|---|
| CN | 102 940 652 B | 3/2015 |
| JP | 2008-532558 A | 8/2008 |
| JP | 2010-280640 A | 12/2010 |
| WO | WO 2006/099699 A1 | 9/2006 |
| WO | WO 2014/121302 A2 | 8/2014 |
| WO | WO 2015/018307 A1 | 2/2015 |

OTHER PUBLICATIONS

Santos-de-Frutos, K. et al., Comm. Biol., vol. 4, 2021 12 pages.*
PCT International Search Report and Written Report application No. PCT/US16/50269, filed Sep. 2, 2016, dated Jan. 24, 2017, 12 pages.
Sakamoto et al., "Eubacterium limosum strain JCM 6421 16S ribosomal RNA gene, partial sequence" NCBI Reference Sequence, 2 pages, Nov. 23, 2016.
Scott J. Bultman, "Emerging roles of the microbiome in cancer", Carcinogenesis vol. 35 No. 2 pp. 249-255, 2014.
Evelien Wynendaele et al., "Crosstalk between the microbiome and cancer cells by quorum sensing peptides", Elsevier Peptides 65 (2015) 40-48.
Khan et al., "Identification of predominant human and animal anaerobic intestinal bacterial species by terminal restriction fragment patterns (TRFPs): a rapid, PCR-based method," Molecular and Cellular Probes 15:349-355 (2001).
Peled et al., "Intestinal Microbiota and Relapse After Hematopoietic-Cell Transplantation," Journal of Clinical Oncology 35(15):1650-1659 (2017).

(Continued)

*Primary Examiner* — Michael D Burkhart
(74) *Attorney, Agent, or Firm* — Baker Botts L.L.P.

(57) ABSTRACT

The present invention relates to methods and compositions for reducing the risk of cancer relapse in a subject who has received cancer treatment. It is based, at least in part, on the discovery that a restricted fraction of the gut microbiota, including the bacteria *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica,* and *Eubacterium brachy* are associated with a reduced risk of cancer relapse.

12 Claims, 34 Drawing Sheets
Specification includes a Sequence Listing.

(56) References Cited

OTHER PUBLICATIONS

Sungkanuparph et al., "Eubacterium Bacteremia and Colon Cancer," Scandinavian Journal of Infectious Disease 34(12):941-943 (2002).
Supplementary Partial European Search Report dated Apr. 25, 2019 in Application No. EP 16843142.
Wang et al., "DNA microarray analysis of predominant human intestinal bacteria in fecal samples," Molecular and Cellular Pro 18:223-234 (2004).
Wang, et al., "PCR Detection and Quantitation of Predominant Anaerobic Bacteria in Human and Fecal Samples," Applied and Environmental Microbiology 62(4):1242-1247 (1996).
Office Action dated Aug. 28, 2020 corresponding to Japanese Patent Application No. 2018-511660.

* cited by examiner

*Acidaminococcus intestini* is associated with less relapse after multivariate adjustment

Acidaminococcus intestini

| Variable | HR | Lower 95% CI | Upper 95% CI | p value |
|---|---|---|---|---|
| Unadjusted | 0.899 | 0.829 | 0.974 | 0.010 |
| Conditioning Intensity | 0.903 | 0.833 | 0.980 | 0.015 |
| Graft Source | 0.896 | 0.827 | 0.972 | 0.008 |
| Disease Risk Index | 0.902 | 0.832 | 0.979 | 0.013 |
| All 3: DRI, Intensity, and Source | 0.899 | 0.828 | 0.975 | 0.010 |

Refined Disease Risk Index

| Predictor | HR | Lower 95% CI | Upper 95% CI | p value |
|---|---|---|---|---|
| DRI | 0.51 | 0.38 | 0.70 | 0.00002 |

HR–Hazard Ratio

Combined discovery & validation cohorts (n=466)
Conditioning Intensity (Bacigalupo, *BBMT* 2009)
Graft Source (T-cell depleted, cord, unmodified PBSC/BM)
Refined Desease Risk Index (Armand *Blood* 2014)

FIG. 13

| Taxon | multivariate p value | multivariate HR | univariate p value | univariate HR | Selected member species |
|---|---|---|---|---|---|
| crOTU 1614 | 0.01 | 0.83 | 0.01 | 0.84 | Eubacterium limosum, Peptococcus niger, Anaerofustis stercorihominis, Pseudoramibacter alactolyticus |
| crOTU 2022 | 0.01 | 1.29 | 0.03 | 1.24 | Streptococus sinensis, S. salivarius, S. thermophilus, S. dentisani |
| crOTU 2023 | 0.01 | 1.29 | 0.03 | 1.25 | Streptococus sinensis, S. salivarius, S. thermophilus, S. dentisani |
| crOTU 1638 | 0.02 | 0.86 | 0.02 | 0.85 | Eubacterium limosum, Pseudoramibacter alactolyticus |
| crOTU 0951 | 0.02 | 1.17 | 0.05 | 1.14 | Leptotrichia hongkongensis, L. trevisanii, L. wadei, L. buccalis, L. hofstadii |
| crOTU 0953 | 0.02 | 1.17 | 0.05 | 1.14 | Leptotrichia hongkongensis, L. trevisanii, L. wadei, L. buccalis, L. hofstadii |
| crOTU 0952 | 0.03 | 1.17 | 0.06 | 1.14 | Leptotrichia hongkongensis, L. trevisanii, L. wadei, L. buccalis, L. hofstadii |
| crOTU 2986 | 0.03 | 1.25 | 0.05 | 1.23 | Flavonifractor plautii, Oscillibacter ruminantium, Eubacterium desmolans |
| crOTU 3010 | 0.03 | 1.25 | 0.05 | 1.22 | Flavonifractor plautii, Oscillibacter ruminantium, Eubacterium desmolans |
| crOTU 2987 | 0.03 | 1.25 | 0.05 | 1.22 | Flavonifractor plautii, Oscillibacter ruminantium, Eubacterium desmolans |

FIG. 21

| Combined Cohort n=541 | Univariate HR(95%CI) | P-value | Multivariate I crOTU log transformed HR(95%CI) | P-value | Multivariate II crOTU log present/absent HR(95%CI) | P-value | Multivariate III crOTU log abundance bins HR(95%CI) | P-value |
|---|---|---|---|---|---|---|---|---|
| crOTU 1614, log transformed | 0.83(0.75–0.92) | <0.001 | 0.84(0.76–0.93) | <0.001 | | | | |
| OTU 1614, present | 0.51(0.36–0.73) | <0.001 | | | 0.54(0.38–0.78) | <0.001 | | |
| crOTU 1614, abundance bins | | 0.001 | | | | | | 0.004 |
| Absent | (reference) | | | | | | (reference) | |
| Present, tertile 1 | 0.63(0.41–0.98) | | | | | | 0.64(0.42–0.99) | |
| Present, tertile 2 | 0.51(0.32–0.81) | | | | | | 0.56(0.35–0.89) | |
| Present, tertile 3 | 0.4(0.25–0.66) | | | | | | 0.42(0.26–0.69) | |
| Intensity | | 0.27 | | 0.760 | | 0.66 | | 0.77 |
| Myeloablative | (reference) | | (reference) | | (reference) | | (reference) | |
| Reduced Intensity | 0.8 (0.54–1.19) | | 0.94(0.53–1.65) | | 0.92(0.52–1.61) | | 0.96(0.54–1.69) | |
| Nonmyeloablative | 0.67 (0.37–1.19) | | 0.75(0.35–1.61) | | 0.7(0.33–1.5) | | 0.76(0.35–1.64) | |
| Source | | 0.004 | | <0.001 | | 0.001 | | 0.001 |
| Unmodified | (reference) | | (reference) | | (reference) | | (reference) | |
| Cord Blood | 0.34(0.18–0.65) | | 0.32(0.16–0.63) | | 0.33(0.17–0.65) | | 0.32(0.16–0.64) | |
| TCD | 0.75(0.53–1.07) | | 0.6(0.37–0.97) | | 0.59(0.36–0.96) | | 0.6(0.37–0.98) | |
| DRI | | <0.001 | | <0.001 | | <0.001 | | <0.001 |
| Low | 0.61(0.32–1.18) | | 0.61(0.29–1.26) | | 0.61(0.29–1.25) | | 0.61(0.29–1.26) | |
| Intermediate | (reference) | | (reference) | | (reference) | | (reference) | |
| High | 2.05(1.43–2.93) | | 1.91(1.33–2.74) | | 1.89(1.32–2.72) | | 1.89(1.32–2.72) | |

FIG. 22A

| Discovery Cohort n=271 | Univariate HR(95%CI) | P-value | Multivariate I crOTU log transformed HR(95%CI) | P-value | Multivariate II crOTU log present/absent HR(95%CI) | P-value | Multivariate III crOTU log abundance bins HR(95%CI) | P-value |
|---|---|---|---|---|---|---|---|---|
| crOTU 1614, log transformed | 0.84(0.73–0.96) | 0.01 | 0.83(0.71–0.96) | 0.01 | | | | |
| OTU 1614, present | 0.49(0.3–0.82) | 0.006 | | | 0.46(0.27–0.78) | 0.004 | | |
| crOTU 1614, abundance bins | | 0.03 | | | | | | 0.03 |
| Absent | (reference) | | | | | | (reference) | |
| Present, tertile 1 | 0.59(0.32–1.1) | | | | | | 0.53(0.28–1) | |
| Present, tertile 2 | 0.55(0.3–1.03) | | | | | | 0.51(0.27–0.98) | |
| Present, tertile 3 | 0.38(0.2–0.72) | | | | | | 0.37(0.19–0.72) | |
| Intensity | | 0.30 | | 0.53 | | 0.44 | | 0.57 |
| Myeloablative | (reference) | | (reference) | | (reference) | | (reference) | |
| Reduced Intensity | 0.73(0.4–1.32) | | 0.69(0.31–1.54) | | 0.66(0.3–1.47) | | 0.7(0.31–1.57) | |
| Nonmyeloablative | 0.63(0.32–1.24) | | 0.63(0.25–1.57) | | 0.58(0.23–1.45) | | 0.64(0.25–1.62) | |
| Source | | 0.04 | | 0.03 | | 0.04 | | 0.04 |
| Unmodified | (reference) | | (reference) | | (reference) | | (reference) | |
| Cord Blood | 0.35(0.15–0.8) | | 0.41(0.17–0.99) | | 0.43(0.18–1.05) | | 0.53(0.28–1.02) | |
| TCD | 0.72(0.45–1.17) | | 0.52(0.27–1) | | 0.51(0.27–0.98) | | 0.43(0.17–1.05) | |
| DRI | | <0.001 | | 0.005 | | 0.004 | | 0.004 |
| Low | 0.55(0.23–1.29) | | 0.52(0.2–1.33) | | 0.52(0.2–1.35) | | 0.51(0.19–1.31) | |
| Intermediate | (reference) | | (reference) | | (reference) | | (reference) | |
| High | 2.19(1.35–3.55) | | 2.02(1.23–3.33) | | 2.07(1.22–3.42) | | 2.07(1.25–3.44) | |

FIG. 22B

| Validation Cohort n=270 | Univariate HR(95%CI) | P-value | Multivariate I crOTU log transformed HR(95%CI) | P-value | Multivariate II crOTU log present/absent HR(95%CI) | P-value | Multivariate III crOTU log abundance bins HR(95%CI) | P-value |
|---|---|---|---|---|---|---|---|---|
| crOTU 1614, log transformed | 0.82(0.71–0.95) | 0.009 | 0.82(0.7–0.96) | 0.01 | | | | |
| OTU 1614, present | 0.52(0.31–0.87) | 0.01 | | | 0.54(0.31–0.92) | 0.03 | | |
| crOTU 1614, abundance bins | | 0.05 | | | | | | 0.09 |
| Absent | (reference) | | | | | | (reference) | |
| Present, tertile 1 | 0.68(0.37–1.25) | | | | | | 0.67(0.36–1.26) | |
| Present, tertile 2 | 0.43(0.21–0.89) | | | | | | 0.48(0.23–1.01) | |
| Present, tertile 3 | 0.43(0.2–0.91) | | | | | | 0.4(0.18–0.88) | |
| Intensity | | 0.79 | | 0.71 | | 0.72 | | 0.66 |
| Myeloablative | (reference) | | (reference) | | (reference) | | (reference) | |
| Reduced Intensity | 0.87(0.51–1.49) | | 1.36(0.61–3.04) | | 1.33(0.6–2.99) | | 1.41(0.63–3.18) | |
| Nonmyeloablative | 0.72(0.22–2.34) | | 1.03(0.25–4.24) | | 0.95(0.23–3.87) | | 1.02(0.25–4.21) | |
| Source | | 0.10 | | 0.03 | | 0.03 | | 0.03 |
| Unmodified | (reference) | | (reference) | | (reference) | | (reference) | |
| Cord Blood | 0.32(0.11–0.91) | | 0.23(0.07–0.69) | | 0.24(0.08–0.72) | | 0.23(0.07–0.69) | |
| TCD | 0.79(0.47–1.32) | | 0.76(0.37–1.56) | | 0.75(0.37–1.56) | | 0.76(0.37–1.58) | |
| DRI | | 0.03 | | 0.07 | | 0.08 | | 0.09 |
| Low | 0.73(0.26–2.04) | | 0.76(0.24–2.36) | | 0.7(0.23–2.16) | | 0.79(0.25–2.49) | |
| Intermediate | (reference) | | (reference) | | (reference) | | (reference) | |
| High | 1.91(1.13–3.25) | | 1.81(1.06–3.11) | | 1.78(1.04–3.05) | | 1.79(1.04–3.08) | |

FIG. 22C

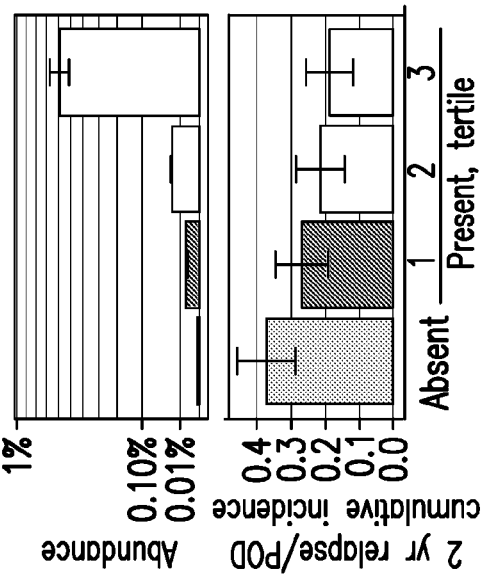
FIG. 25
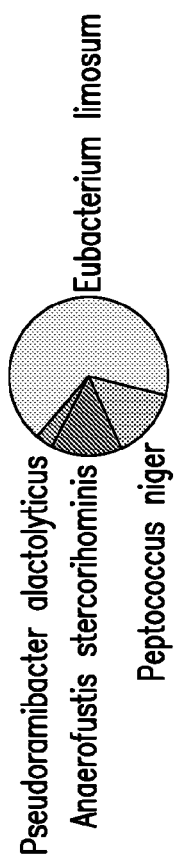
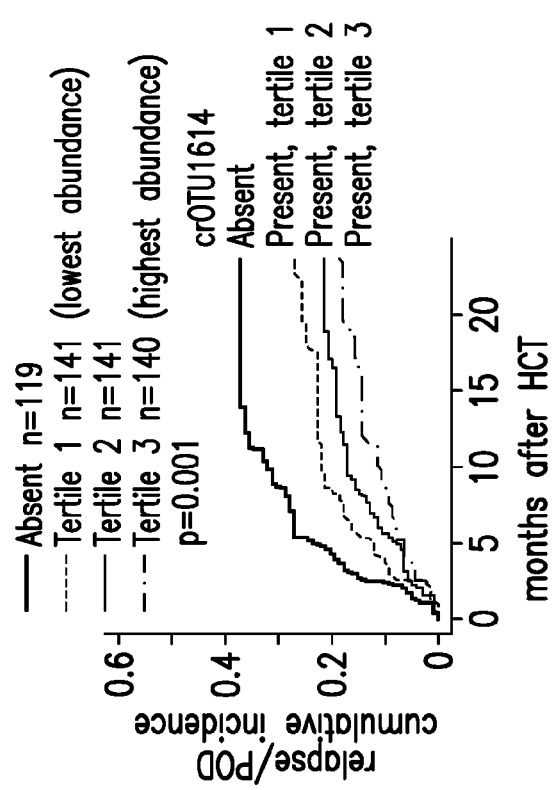
FIG. 26B
FIG. 26A

| Abundance Bin | minimum | mean | median | maximum | n |
|---|---|---|---|---|---|
| Absent | 0 | 0 | 0 | 0 | 119 |
| Present, Tertile 1 | 1.69E-07 | 4.16E-05 | 4.21E-05 | 9.33E-05 | 141 |
| Present, Tertile 2 | 9.46E-05 | 2.22E-04 | 1.76E-04 | 5.22E-04 | 141 |
| Present, Tertile 3 | 5.34E-04 | 5.79E-03 | 1.85E-03 | 8.00E-02 | 140 |

Abundance of crOTU 1614 used in the analysis of post-transplant samples (Figures 26B, C)

| Abundance Bin | minimum | mean | median | maximum | n |
|---|---|---|---|---|---|
| Absent | 0 | 0 | 0 | 0 | 154 |
| Present, Tertile 1 | 2.14E-05 | 1.23E-04 | 1.13E-04 | 2.45E-04 | 105 |
| Present, Tertile 2 | 2.46E-04 | 7.04E-04 | 6.28E-04 | 1.50E-03 | 105 |
| Present, Tertile 3 | 1.53E-03 | 2.51E-02 | 1.51E-02 | 3.46E-01 | 105 |

Abundance of crOTU 1614 used in the analysis of pre-transplant (Figure 33)

| Abundance Bin | minimum | mean | median | maximum | n |
|---|---|---|---|---|---|
| Absent | 0 | 0 | 0 | 0 | 54 |
| Present, Tertile 1 | 2.21E-05 | 1.47E-04 | 1.16E-04 | 3.80E-04 | 30 |
| Present, Tertile 2 | 3.96E-04 | 8.88E-04 | 7.80E-04 | 1.57E-03 | 30 |
| Present, Tertile 3 | 1.59E-03 | 1.85E-02 | 9.33E-03 | 6.59E-02 | 29 |

Abundance of crOTU 1614 used in the analysis of pre-transplant samples from recipients of BM/PBSC grafts (Figure 32)

FIG. 34

METHODS AND COMPOSITIONS FOR DETECTING RISK OF CANCER RELAPSE

CROSS-REFERENCE TO RELATED APPLICATIONS

This application is a national phase of International Application No. PCT/US2016/050269 filed Sep. 2, 2016, which claims priority to U.S. Provisional Application Ser. No. 62/214,604, filed on Sep. 4, 2015, U.S. Provisional Application Ser. No. 62/265,327, filed on Dec. 9, 2015, and U.S. Provisional Application Ser. No. 62/298,258, filed on Feb. 22, 2016, priority to each of which is claimed, and the contents of each of which are incorporated in their entireties herein.

STATEMENT OF GOVERNMENT INTEREST

This invention was made with government support under AI100288 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, is named 0727340414seqlist_ST25.txt and is 3,500 bytes in size.

1. INTRODUCTION

The present invention relates to compositions and methods for diagnosing a subject as being at a greater or reduced risk for cancer relapse, and to compositions and methods for treating said subject.

2. BACKGROUND OF THE INVENTION

The gastrointestinal tract of mammals is densely colonized by hundreds of microbial species that coexist symbiotically with their hosts. The microbes, collectively referred to as the microbiota, contribute to numerous aspects of host health, including nutrient metabolism, homeostasis of intestinal tissues, development of innate and adaptive immune responses, and more generally, defense against intestinal infection. Bacteria antagonize intestinal pathogens directly, through contact-dependent and soluble factor-mediated inhibition, as well as indirectly by modulating and inducing host immune responses, but the contributions of individual bacteria to colonization resistance against specific pathogens are not well understood.

It has been reported that changes in the intestinal flora can affect graft-versus-host disease (GVHD) and are associated with bacteremia and overall survival after allogeneic hematopoietic stem cell transplantation (allo-HSCT). The major causes of mortality after allo-HSCT are relapse, GVHD, and infection. Identifying components of the intestinal flora that are associated with relapse after allo-HSCT would allow for therapeutic intervention in specific patient populations at risk for a relapse.

3. SUMMARY OF THE INVENTION

Applicants have discovered that, surprisingly, the risk of cancer relapse after HSCT is associated with the presence and/or absence of a specific group of bacteria. Accordingly, the present invention relates to methods and compositions for determining the likelihood of relapse of a subject's cancer as well as methods and compositions for decreasing the risk of relapse in at risk patients. In certain non-limiting embodiments, the present invention further provides for methods of treating a subject determined to be at greater or reduced risk for a cancer relapse.

In certain non-limiting embodiments, the present invention provides for a method of determining the presence of bacteria or spores thereof in a sample from a subject who has been diagnosed with, or is at risk for having, cancer. In certain non-limiting embodiments, the subject has received cancer treatment, for example, a hematopoietic stem cell transplantation (HSCT), such as an allogeneic stem cell transplantation (allo-HSCT), before or after determining the presence of bacteria in the sample.

In certain non-limiting embodiments, detection of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, in a subject sample indicates a reduced risk of cancer relapse.

In certain non-limiting embodiments, the bacteria or spores thereof detected is *Eubacterium limosum, Peptococcus niger, Anaerofustis stercorihominis, Pseudoramibacter alactolyticus, Saccharofermentans acetigenes, Armatimonas rosea*, a combination thereof, or a cluster comprising any one or more of the foregoing bacteria.

In certain non-limiting embodiments, the bacteria or spores thereof detected is *Eubacterium limosum*, or a cluster comprising *Eubacterium limosum*.

In certain non-limiting embodiments, the bacteria detected is *Parvimonas micra, Finegoldia magna, Levyella massiliensis, Gallicola barnesae, Murdochiella asaccharolytica, Eubacterium brachy*, a combination thereof, or a cluster comprising any one or more of the foregoing bacteria.

In certain non-limiting embodiments, the bacteria or spores thereof comprise a 16S rRNA sequence that has between about 85 and 100% identity with a nucleic acid sequence described by any one of SEQ ID NOS: 1-12 or SEQ ID NOS: 1-17.

In certain non-limiting embodiments, the subject sample is a fecal sample or intestinal microbiota sample. In certain non-limiting embodiments, the abundance of bacteria in the sample from a first subject indicates a reduced risk of cancer relapse when the abundance of the bacteria is greater than the level of said bacteria in a sample from a second subject that has had a cancer relapse, or greater than a reference level, for example, a level of bacteria present in the intestinal microbiota above which is indicative of a reduced risk of cancer relapse.

In certain non-limiting embodiments, detecting an abundance of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, in a sample from a first subject that is lower than the abundance of the bacteria in a sample from a second subject that has not had a cancer relapse is indicative of the first subject being at greater risk for a cancer relapse. In certain non-limiting embodiments, an abundance in the sample from the first subject that is lower than a reference level is indicative of the first subject being at greater risk of cancer relapse, for example, a level of bacteria present in the intestinal microbiota below which is indicative of being at a greater risk of cancer relapse.

In certain non-limiting embodiments, detection of *Enterococcus faecium* in a subject sample indicates greater risk of cancer relapse. In certain non-limiting embodiments, the subject sample is a fecal sample or intestinal microbiota sample. In certain non-limiting embodiments, the abundance of bacteria in the sample from a first subject indicates greater risk of cancer relapse when the abundance of the bacteria is greater than the abundance of said bacteria in a sample from a second subject that has not had a cancer relapse, or greater than a reference level, for example, a level of bacteria present in the intestinal microbiota above which is indicative of being at a greater risk of cancer relapse.

In certain non-limiting embodiments, detecting an abundance of *Enterococcus faecium* in the sample from a first subject that is lower than the abundance of the bacteria in a sample from a second subject that has had a cancer relapse is indicative of the first subject being at a reduced risk for a cancer relapse. In certain non-limiting embodiments, an abundance in the sample from the first subject that is lower than a reference level is indicative of the first subject being at a reduced risk of cancer relapse, for example, a level of bacteria present in the intestinal microbiota below which is indicative of a reduced risk of cancer relapse.

In certain non-limiting embodiments, the methods of detecting the abundance of one or more bacteria in a fecal sample or intestinal microbiota sample are conducted on the sample in vitro.

In certain non-limiting embodiments, the methods of the present invention further comprise administering cancer therapy to a subject when the subject has been determined to have a greater risk of cancer relapse.

In certain non-limiting embodiments the therapy comprises administering a probiotic to the subject, wherein the probiotic comprises *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria.

In certain non-limiting embodiments the therapy comprises administering a prebiotic to the subject, wherein the prebiotic comprises one or more agents, for example, a nutritional supplement, that increases growth and survival of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria. In certain non-limiting embodiments, the prebiotic comprises one or more of poorly-absorbed complex carbohydrates, oligosaccharides, inulin-type fructans or arabinoxylans.

In certain non-limiting embodiments the therapy comprises administering a postbiotic to the subject, wherein the postbiotic comprises one or more agents, such as a protein, expressed by *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria. In certain non-limiting embodiments, the postbiotic comprises media from a culture of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria. In certain non-limiting embodiments, the postbiotic comprises a short-chain fatty acid such as butyrate or similar acids, or secondary bile acids.

In certain non-limiting embodiments, the therapy comprises administering an antibiotic that is specific for *Enterococcus faecium*. In certain non-limiting embodiments, the antibiotic comprises a penicillin, vancomycin, and/or linezolid antibiotic. In certain non-limiting embodiments the antibiotic selectively spares *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria.

In certain non-limiting embodiments, the therapy comprises administering a recombinant *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, or progeny thereof, to the subject. In certain non-limiting embodiments, the recombinant bacteria expresses an antibiotic resistance gene.

In certain non-limiting embodiments, the therapy comprises surgery, radiation therapy, chemotherapy, immunotherapy, stem cell therapy or other cellular therapies such as administration of Chimeric Antigen Receptor modified T cells (CAR-modified T cells) and/or antigen-specific T cells, or a combination thereof.

In certain non-limiting embodiments, the present invention provides for a composition, and therapeutic uses thereof as described herein, comprising one or more isolated bacteria, or spores thereof, selected from the group consisting of Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, or Eubacterium brachy bacteria, a combination thereof, or a cluster comprising any one or more of the foregoing bacteria. In some non-limiting embodiments, the bacteria is in a formulation for administration to a subject. In certain non-limiting embodiments, the bacteria is in a pharmaceutical formulation. In certain non-limiting embodiments, the bacteria is recombinant bacteria, for example, recombinant bacteria expressing an antibiotic resistant gene.

In certain non-limiting embodiments, the composition is formulated for oral, nasogastric, or rectal administration. In certain non-limiting embodiments, the composition further includes probiotic bacteria and/or yeast, a prebiotic, a postbiotic, or an antibiotic. In certain non-limiting embodiments, the composition is formulated as a liquid, suspension, dried powder, tablet, capsule or food product. In certain non-limiting embodiments, the bacteria or cluster thereof is recombinant bacteria, or progeny thereof, which can include one or more exogenous nucleic acids encoding a protein that confers antibiotic sensitivity or resistance to the recombinant bacteria.

In certain non-limiting embodiments, the present invention provides for a method for reducing the risk of cancer relapse, or increasing the rate of survival of a subject having a cancer relapse, comprising administering, to a subject in need of such treatment, an effective amount of a composition comprising a Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica or Eubacterium brachy bacteria, a combination thereof, or a cluster comprising any one or more of the foregoing bacteria.

In various non-limiting embodiments of the invention, bacteria may be administered in the vegetative or dormant state, or as spores, or a mixture thereof.

In some non-limiting embodiments, the present disclosure provides for a method for decreasing the severity of one or more symptoms and/or clinical signs of cancer relapse comprising administering, to a subject in need of such treatment, an effective amount of one or more of a recombinant cell as described herein, or progeny thereof a composition comprising a Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, or Eubacterium brachy bacteria, a combination thereof, or a cluster comprising any one or more of the foregoing bacteria; a probiotic, prebiotic, postbiotic, and/or antibiotic as described herein; surgery; radiation therapy; chemotherapy; immunotherapy; stem cellular therapy; cellular therapy, and combinations thereof, wherein the symptoms and/or clinical signs are selected from the group consisting of presence of cancer cells, cancer cell proliferation, tumor growth, tumor presence, tumor volume, detectable amount of minimal residual disease, or a combination thereof.

The present invention further provides for kits comprising a Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica or Eubacterium brachy, bacteria, a combination thereof, or a cluster comprising any one or more of the foregoing bacteria. In certain non-limiting embodiments, the kit further comprises instructions comprising information about the use of the cells or composition for treating or preventing cancer relapse. In certain non-limiting embodiments, the instructions comprise at least one of the following: description of the therapeutic agent; dosage schedule and administration for treating or preventing cancer relapse or symptoms thereof precautions; warnings; indications; counter-indications; over dosage information; adverse reactions; animal pharmacology; clinical studies; and/or references. The instructions can be printed directly on the container (when present), or as a label applied to the container, or as a separate sheet, pamphlet, card, or folder supplied in or with the container.

The present invention further provides for kits for diagnosing a subject as having an increased risk of cancer relapse, comprising one or more agents for detecting the abundance of one or more bacteria in an intestinal microbiota sample, wherein the one or more bacteria is selected from the group consisting of Streptococcus anginosus, Parvimonas micra, Acidaminococcus intestini, Eubacterium limosum, Clostridium glycyrrhizinilyticum, Desulfosporosinus lacus, Eubacterium biforme, Enterococcus faecium, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, or Eubacterium brachy, bacteria, and a cluster comprising any one or more of the foregoing bacteria.

The present disclosure further provides compositions comprising one or more isolated bacteria, or spores thereof, or cluster comprising said one or more bacteria, as described herein, for use in reducing the risk of cancer relapse and/or increasing likelihood of survival from a cancer relapse in a subject. In certain non-limiting embodiments, the subject has received cancer treatment, for example, a hematopoietic stem cell transplantation (HSCT), such as an allogeneic stem cell transplantation (allo-HSCT), before or after determining the presence of bacteria in the sample. The allogeneic stem cell transplantation (allo-HSCT) can be a T-cell replete allo-HSCT.

In certain non-limiting embodiments, the composition is administrable in an amount effective to decrease the presence of Enterococcus faecium in the subject, and/or decrease the amount of Enterococcus faecium toxin in the subject.

In certain non-limiting embodiments, the subject is at increased risk of cancer relapse, where an intestinal microbiota sample from the subject has a level of one or more of a Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella

*massiliensis, Gallicola barnesae, Murdochiella asaccharolytica* or *Eubacterium brachy* bacteria, or a cluster comprising any one or more of the foregoing bacteria, that is lower than a bacteria reference level. Alternatively or additionally, the intestinal microbiota sample from the subject has a level of *Enterococcus faecium* bacteria that is greater than a bacteria reference level.

In certain non-limiting embodiments, the composition for use in reducing the risk of cancer relapse and/or increasing likelihood of survival from a cancer relapse in a subject, further comprises assaying an intestinal microbiota sample from a subject and determining the level of one or more of a *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica* or *Eubacterium brachy* bacteria, or a cluster comprising any one or more of the foregoing bacteria present in the intestinal microbiota sample, and administering a therapeutically effective amount of the composition to the subject if the level of the one or more bacteria in the sample is lower than a bacteria reference level.

In certain non-limiting embodiments, the composition for use in reducing the risk of cancer relapse and/or increasing likelihood of survival from a cancer relapse in a subject, further comprises assaying an intestinal microbiota sample from a subject and determining the level of *Enterococcus faecium* bacteria present in the intestinal microbiota sample, and administering a therapeutically effective amount of the composition to the subject if the level of *Enterococcus faecium* bacteria in the sample is greater than a bacteria reference level.

In certain non-limiting embodiments, the present disclosure provides for a composition for use in cancer therapy in a subject diagnosed as having an increased risk of cancer relapse, wherein an intestinal microbiota sample from the subject has a level of one or more of a *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica* or *Eubacterium brachy* bacteria, or a cluster comprising any one or more of the foregoing bacteria, that is lower than a bacteria reference level. Additionally, or alternatively, an intestinal microbiota sample from the subject has a level of *Enterococcus faecium* bacteria that is greater than a bacteria reference level. The cancer therapy can include surgery, radiation therapy, chemotherapy, immunotherapy, stem cell therapy, and/or cellular therapy, or can involve administering to the subject probiotic bacteria and/or yeast, a prebiotic, a postbiotic, or an antibiotic.

4. BRIEF DESCRIPTION OF THE FIGURES

FIG. 1 shows quantification of bacterial diversity over a 1 year period using the inverse Simpson index after composition analysis of stool samples from 309 patients performed by 16S gene sequencing.

FIG. 2 shows associations of bacterial genera with relapse, or with relapse risk, over a one year observation period. Associations of bacteria were quantified by Cox univariate regression. Position along the vertical axis indicates statistical significance.

FIG. 3 shows the association between bacterial abundance and relapse after multivariate adjustments for risk factors. The Cox regression model was adjusted for conditioning intensity, graft source (cord vs. unmodified/T-cell replete adult), and Disease Risk Index.

FIGS. 4A-B shows (A) that *Parvimonas micra* abundance is associated with lower risk of relapse, and (B) scatter plots by Mann-Whitney survival by log-rank, indicating that *Parvimonas micra* is a candidate biomarker for protection from relapse.

Figures 12A, 12B:
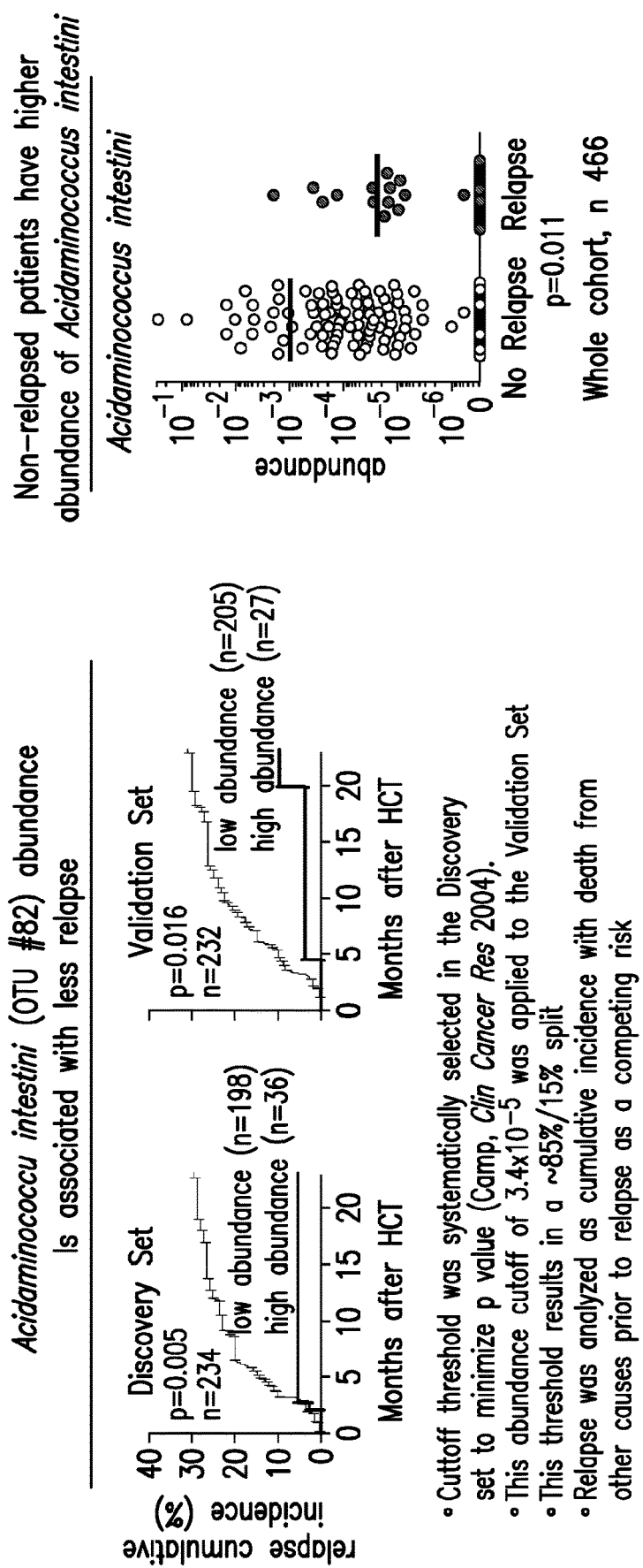

FIGS. 12A-B show the association between *Acidaminococcus intestini* abundance and relapse in both the Discovery and Validation subsets of the 466 patient cohort, wherein the cutoff threshold for bacterial abundance was $3.4\times10^{-5}$ in the regression model. This cutoff resulted in about 85% having low abundance of the bacteria (which was correlated with relapse) and 15% high abundance (which was correlated with a lack of relapse).

FIG. 13 shows that the association between *Acidaminococcus intestini* abundance and relapse after multivariate adjustment.

Figure 14A:
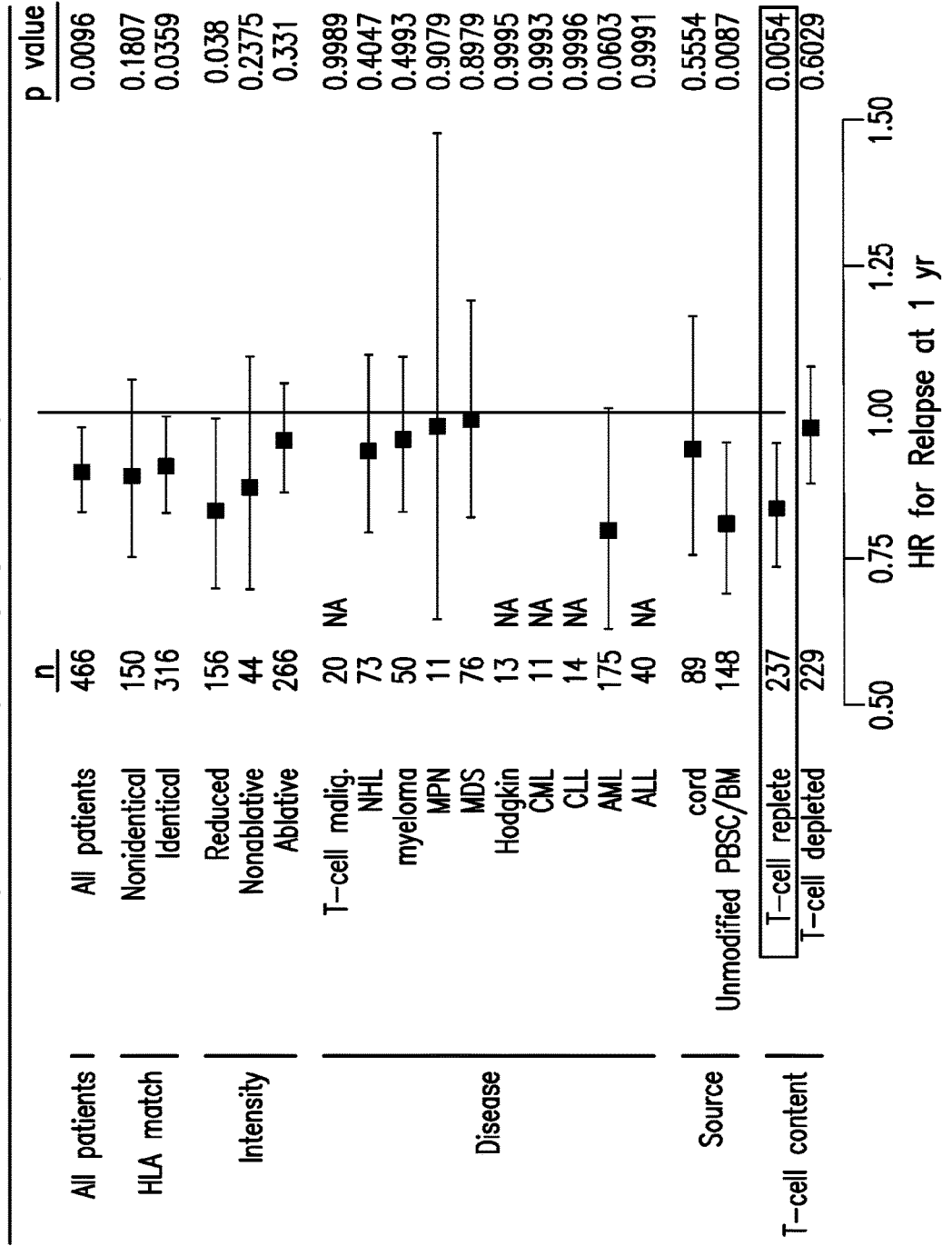
Figure 14:
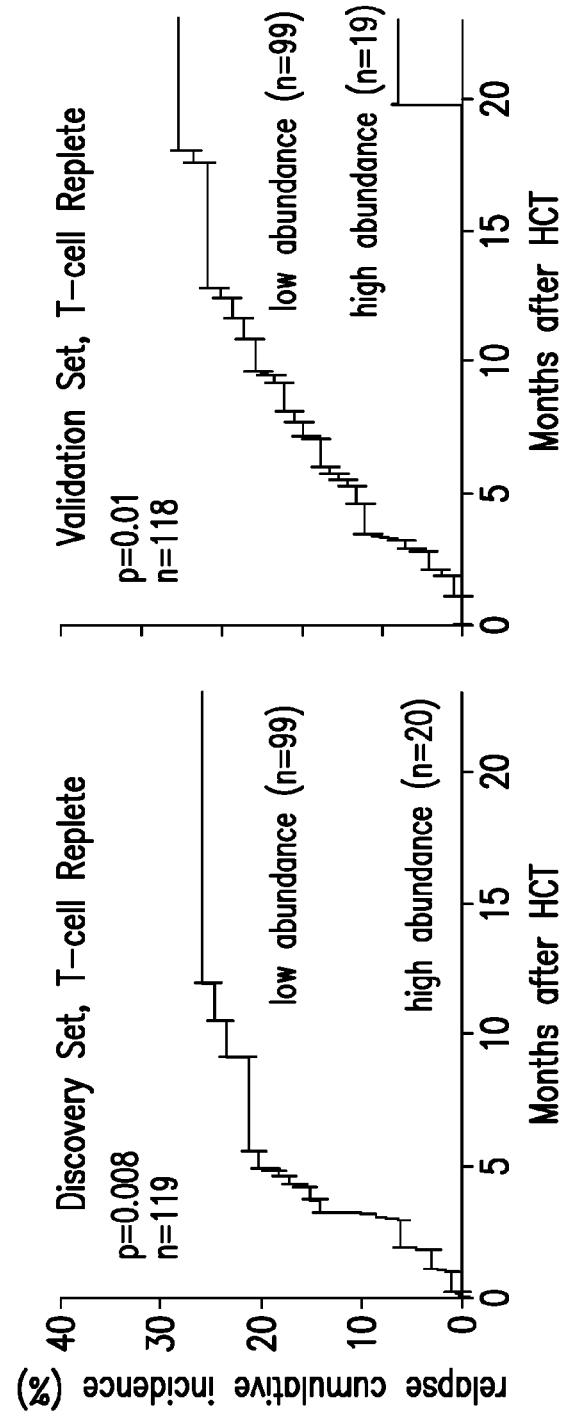

FIGS. 14A-B show the association between *Acidaminococcus intestini* abundance and relapse in patients that received T-cell replete transplants, where FIG. 14A shows the association with respect to several factors and FIG. 14B shows an inverse association between *Acidaminococcus intestini* abundance and relapse.

Figure 15A:
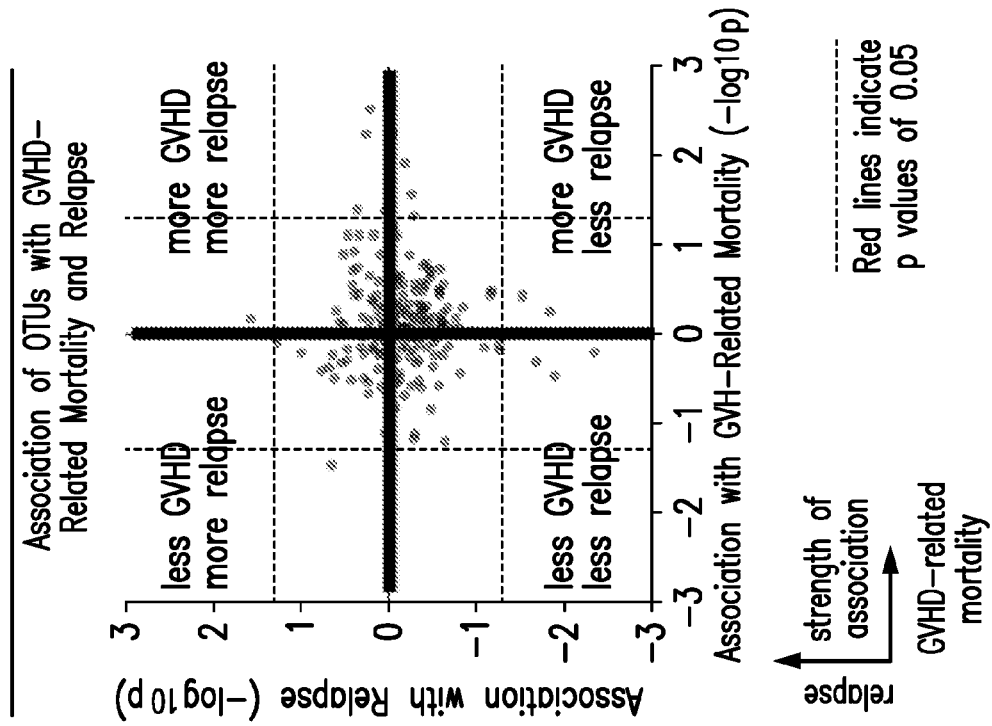
Figure 15B:
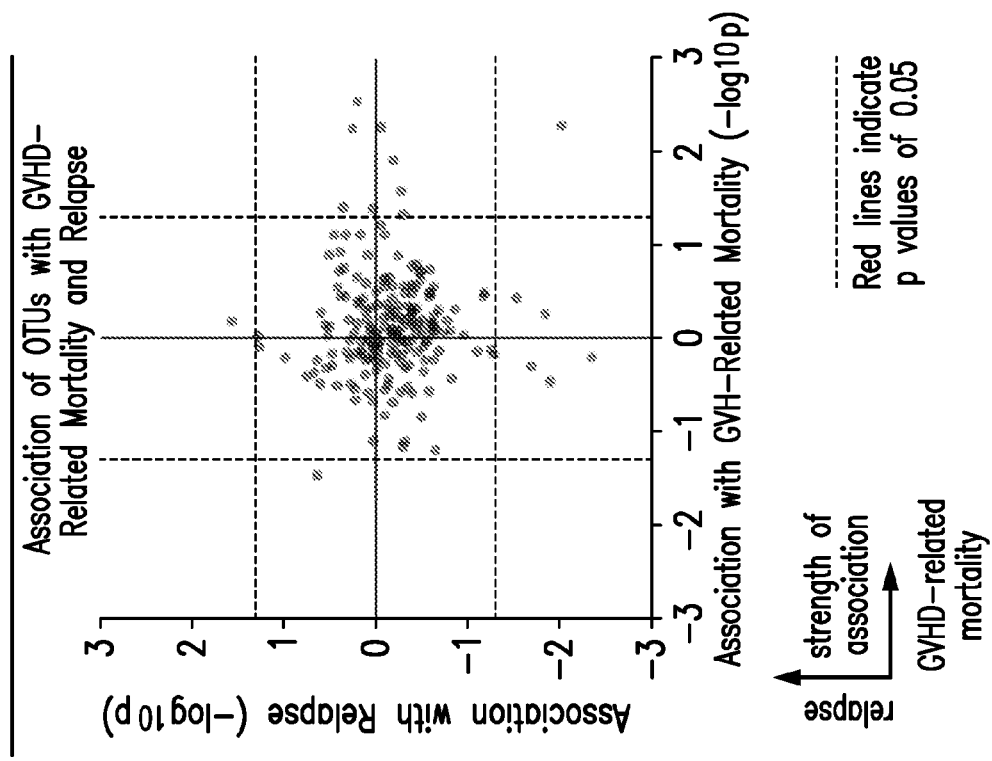

FIGS. 15A-B show scatterplots of various intestinal microbiota and their associations with relapse and GVHD-related mortality.

Figure 16:
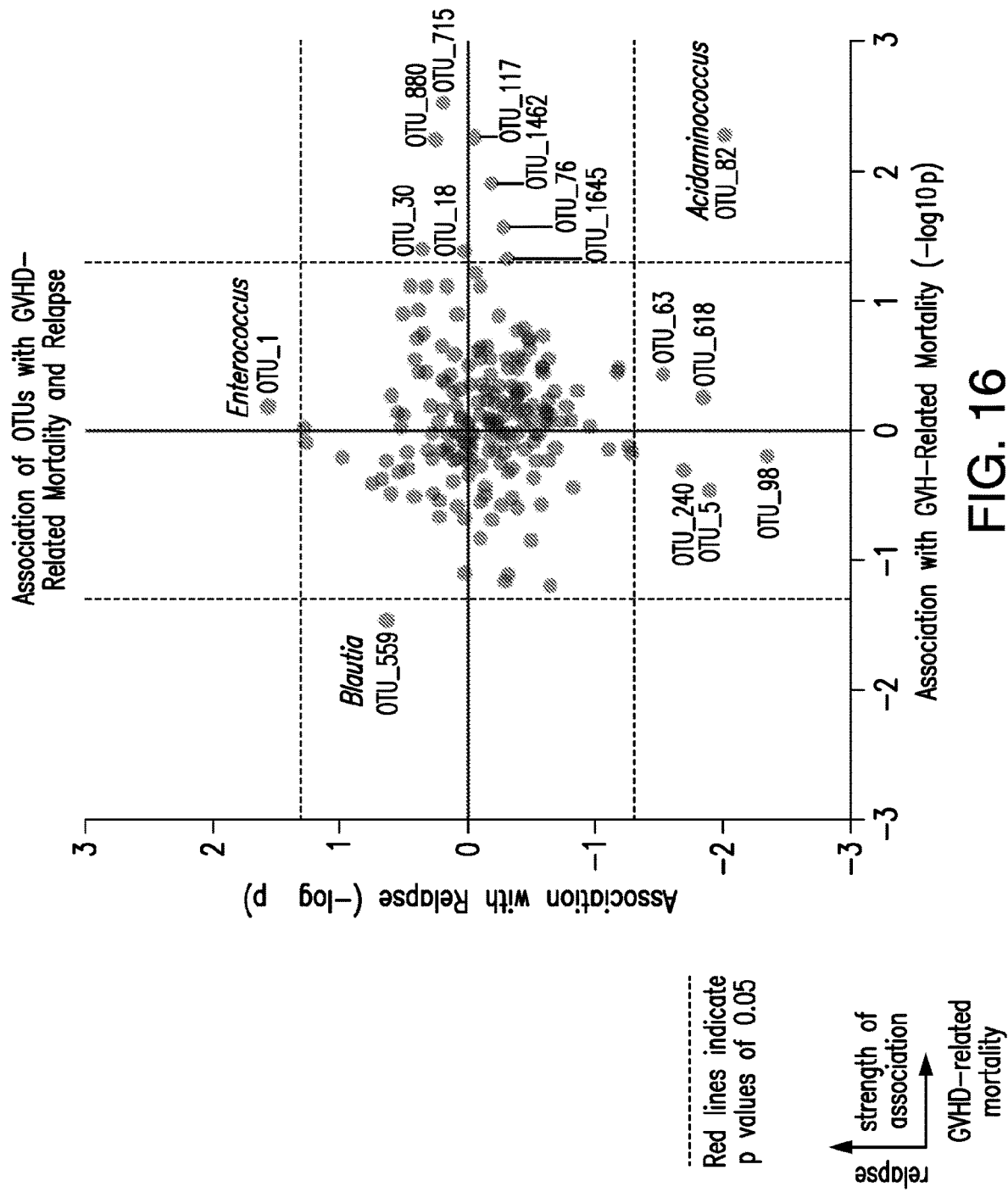

FIG. 16 shows the associations of various intestinal microbiota, including *Enterococcus, Acidaminococcus,* and *Blautia,* with relapse and lack of GVHD-related mortality.

Figure 17:
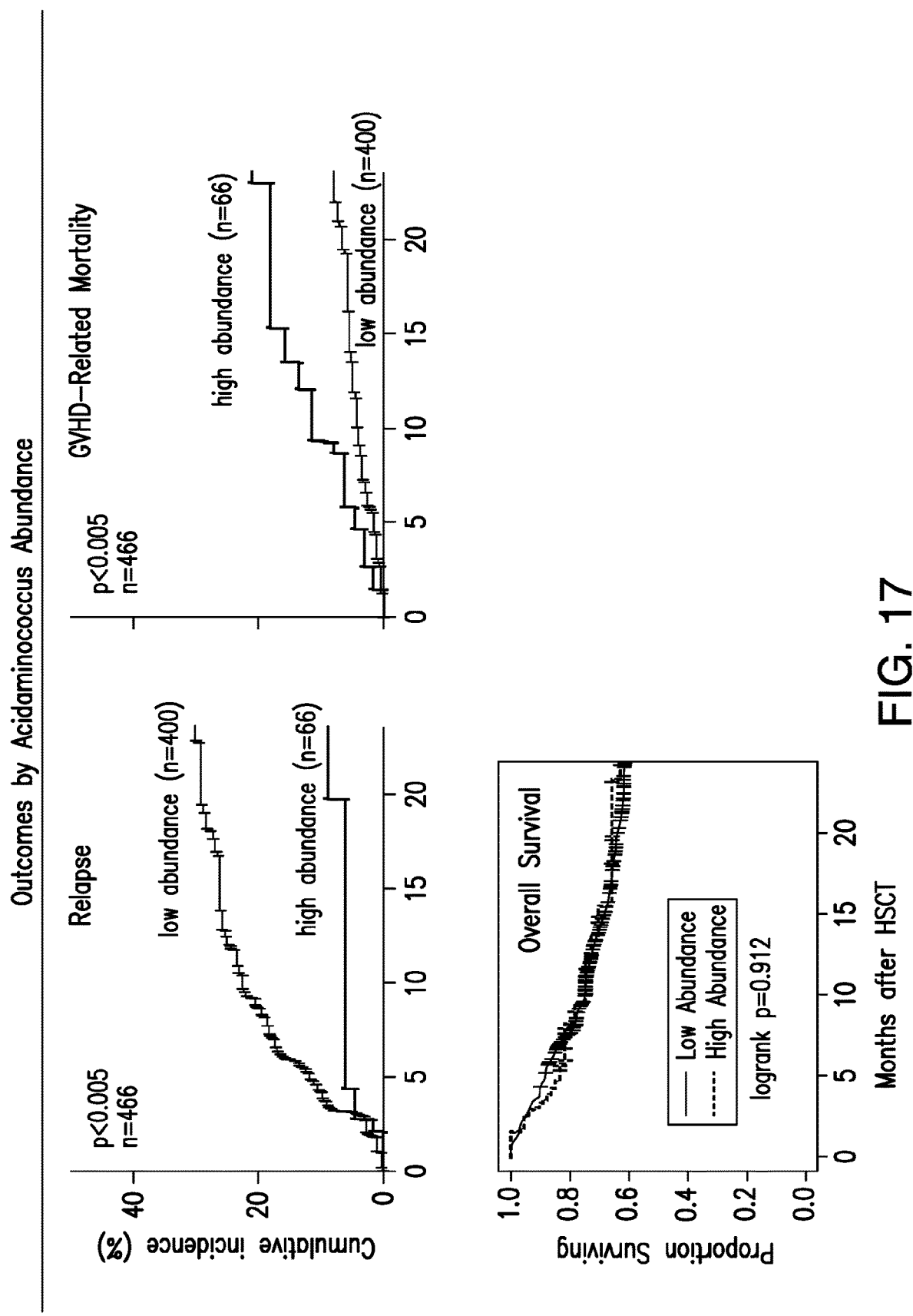

FIG. 17 shows the association between *Acidaminococcus* abundance and overall survival, GVHD-related mortality and a lack of relapse.

Figure 18A:
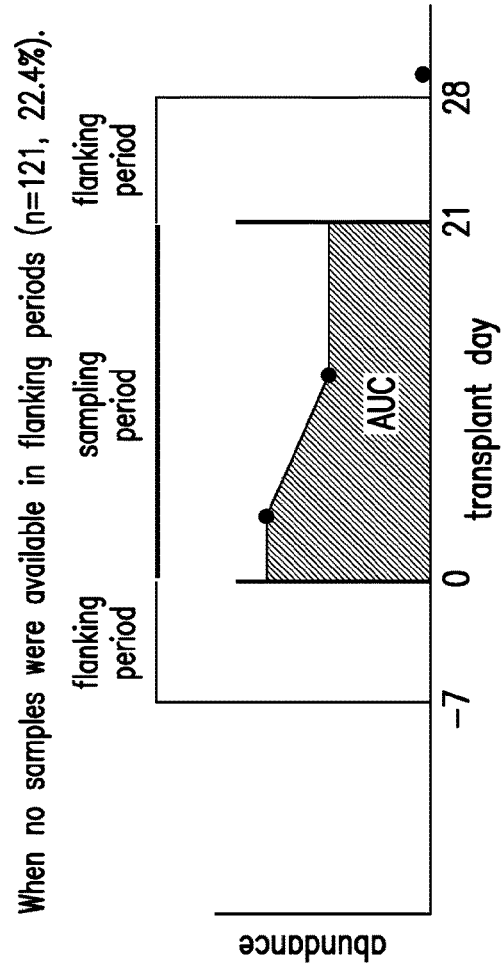
Figure 18B:
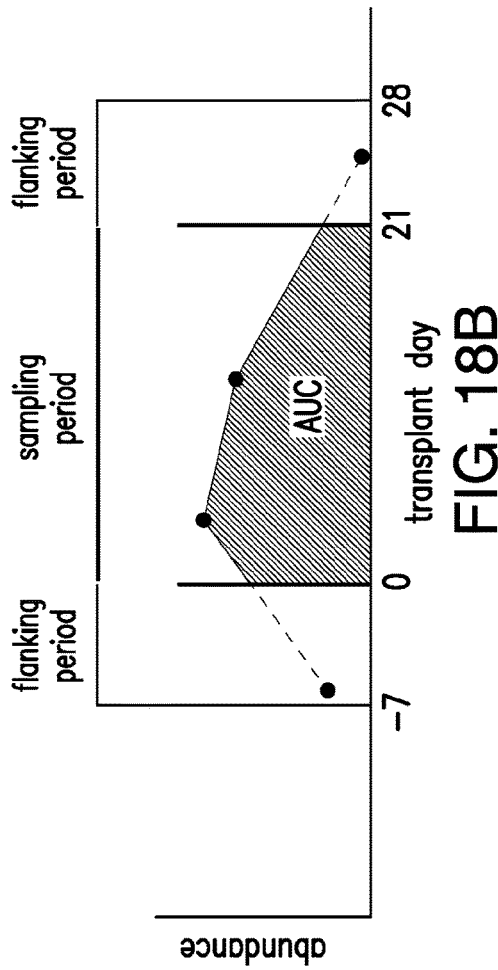

FIGS. 18A-B are schematics of calculations of time-weighted average abundances, where FIG. 18A is for patients where no sample was available from the week preceding and/or the week following the sampling period and FIG. 18B is for patients where at least one additional sample was available from the week preceding and/or the week following the sampling period.

Figure 19:
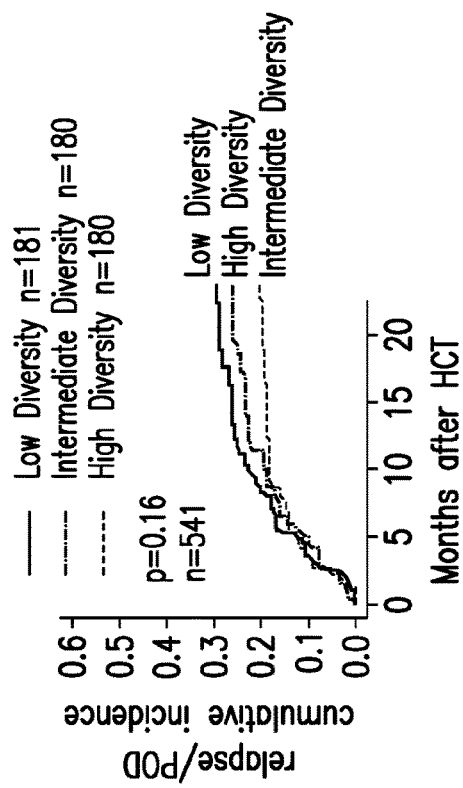

FIG. 19 shows the association between intestinal microbial diversity and time to relapse/POD in the cohort of Example 3.

Figure 20A:
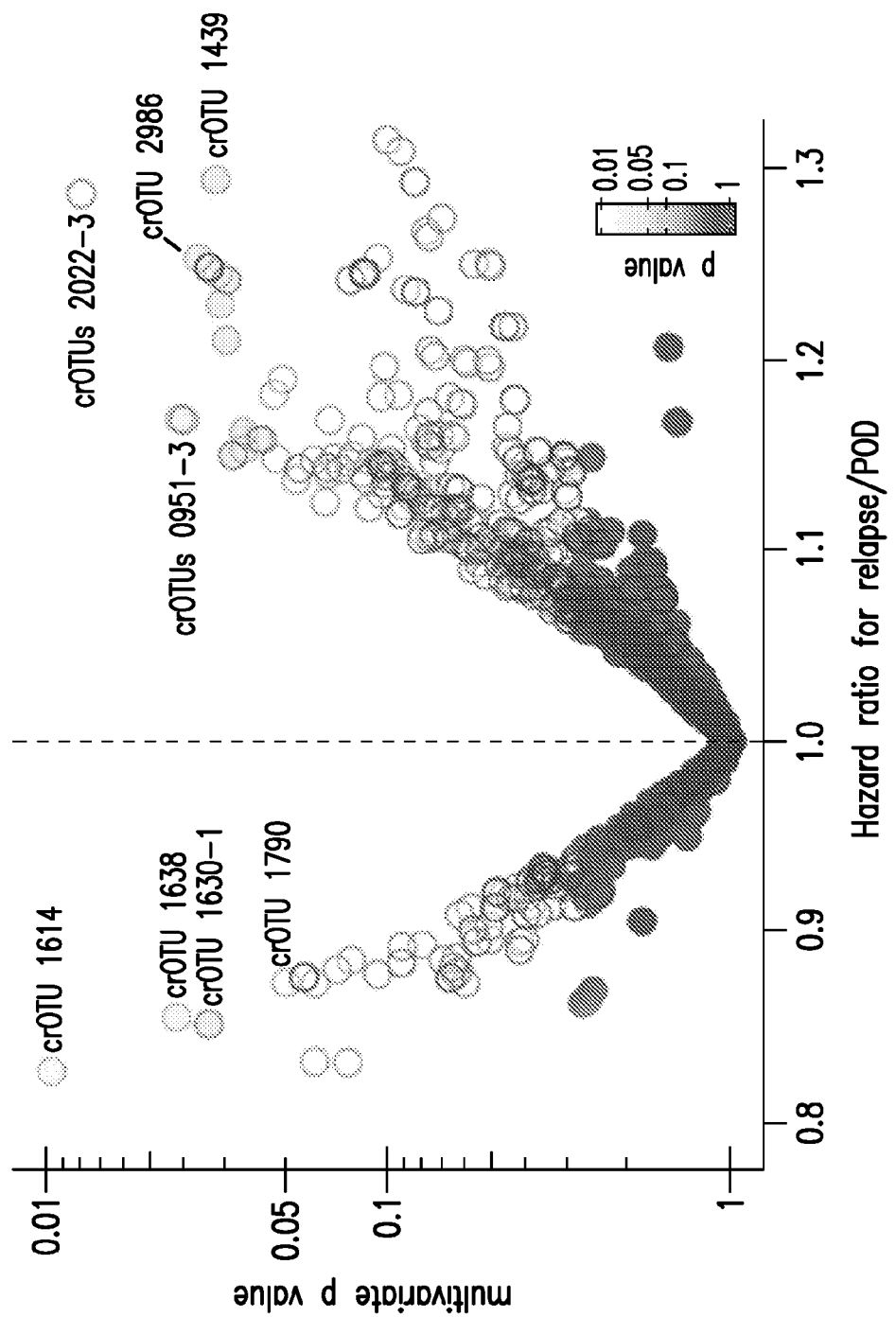
Figure 20B:
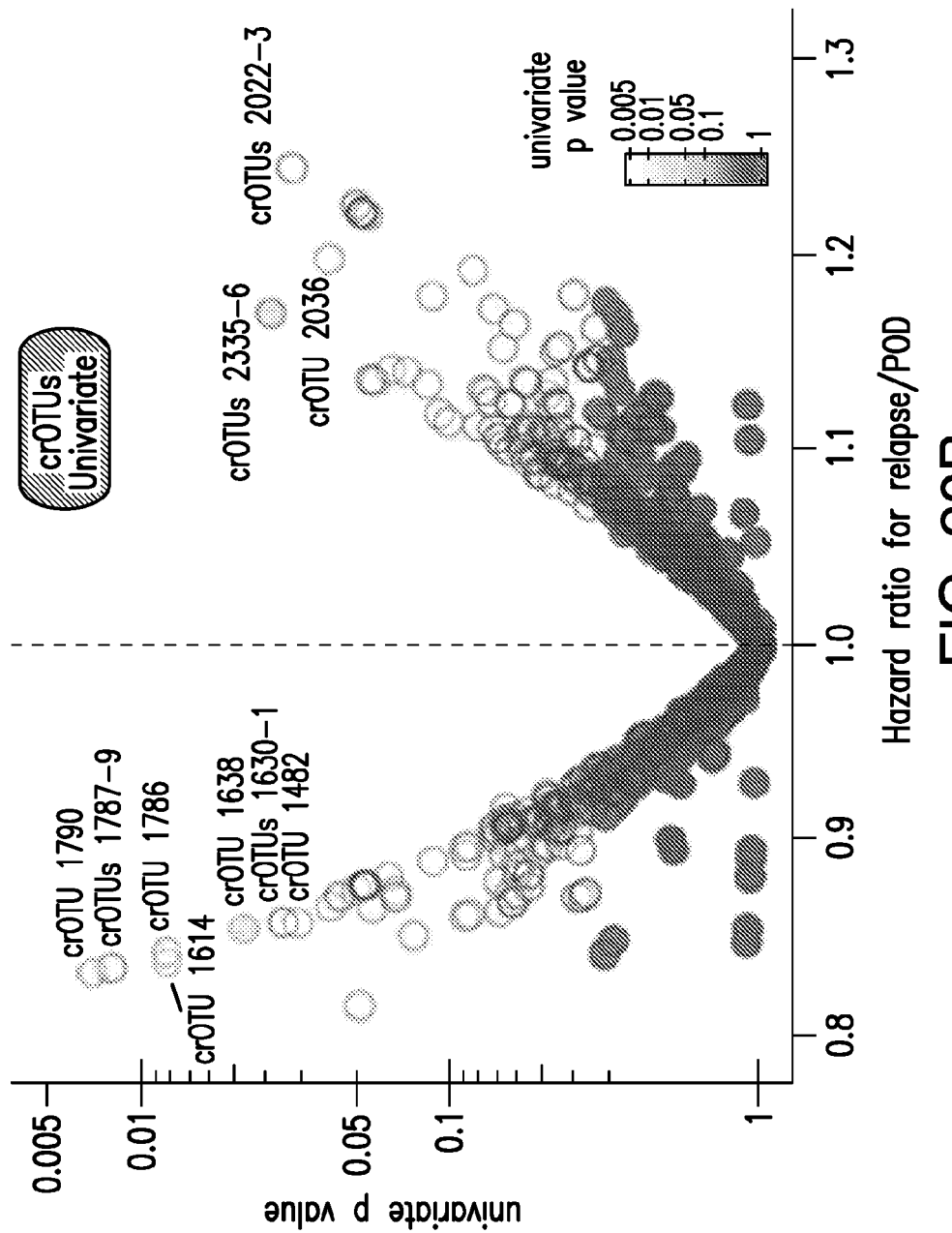
Figure 20C:
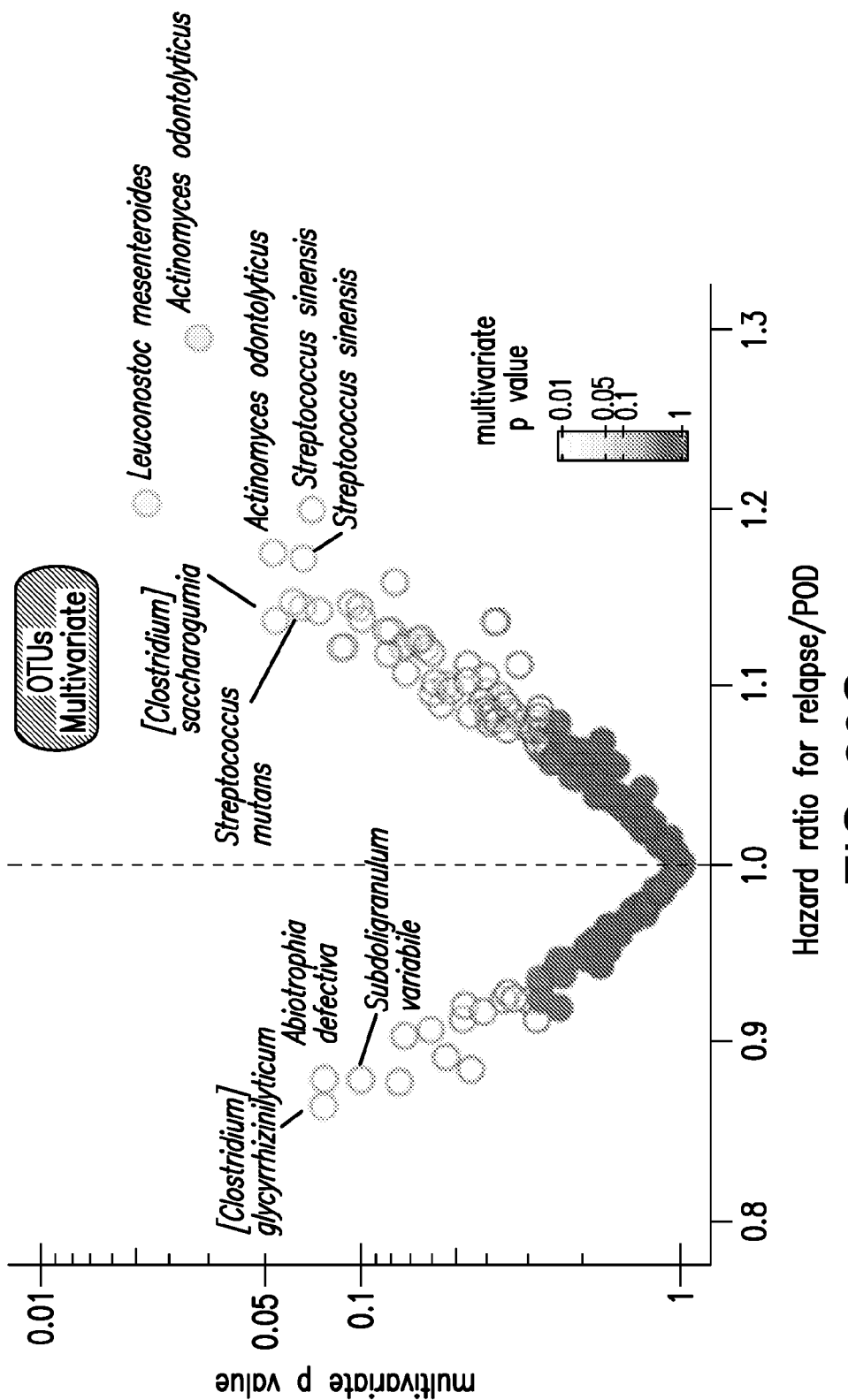
Figure 20D:
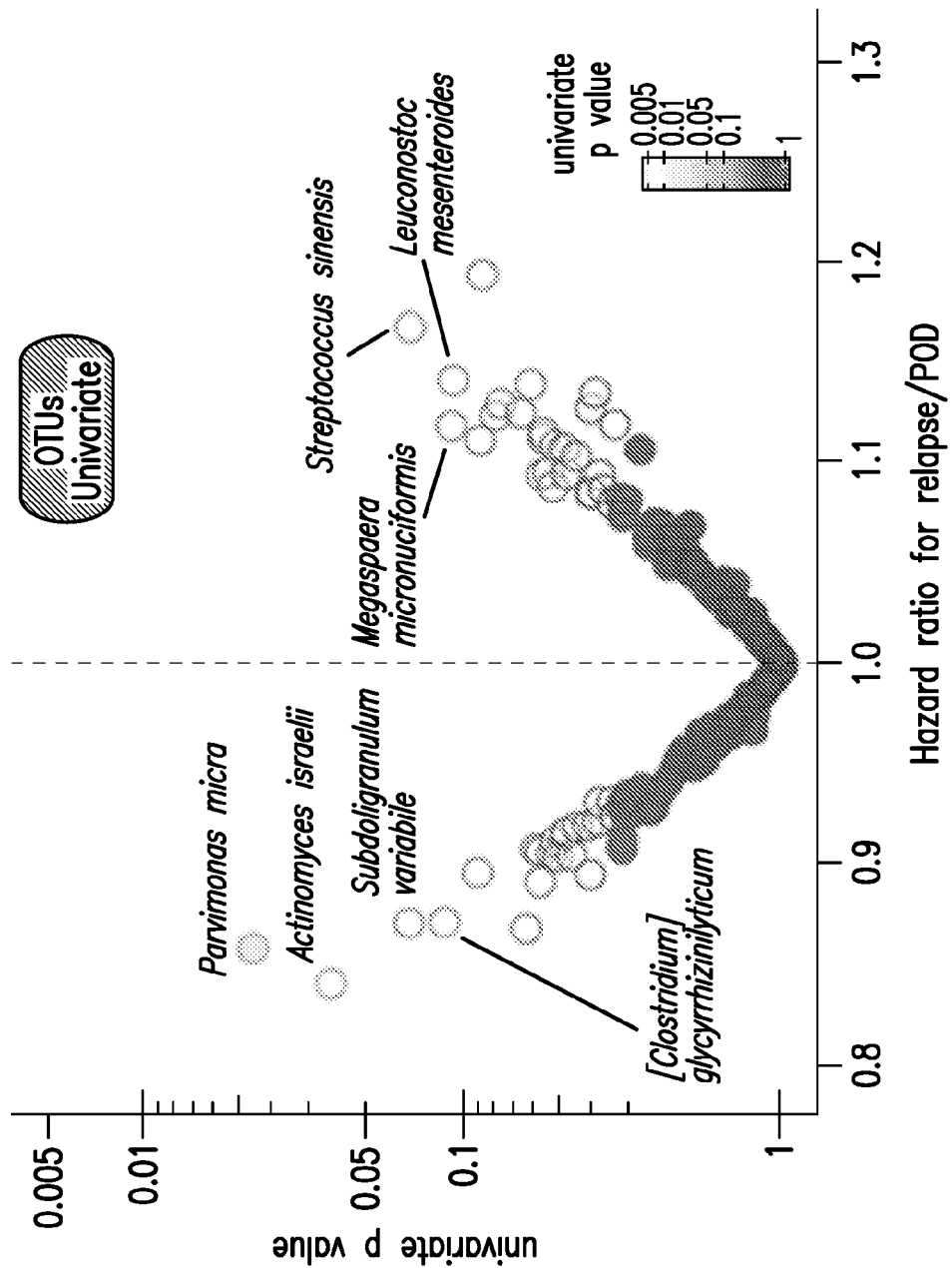

FIGS. 20A-D show volcano plots of multivariate p values of crOTUs against the hazard ratios for relapse/POD (FIG. 20A). FIG. 20B shows crOTU univariate p values plotted against hazard ratios for relapse/POD. FIG. 20C provides volcano plots of multivariate p values of OTUs against the hazard ratios for relapse/POD. FIG. 20D shows OTU univariate p values plotted against hazard ratios for relapse/POD.

FIG. 21 provides the association of the abundance of microbiota features with relapse/POD by Cox models in the Discovery Set (n=271).

FIGS. 22A-C provide univariate and multivariate association of crOTU 1614 with the risk of relapse/POD following allo-HCT using cause-specific Cox proportional hazard regression in the whole cohort (FIG. 22A, n=541), in the discovery cohort (FIG. 22B, n=271), and in the validation cohort (FIG. 22C, n=270). crOTU 1614 is considered either as log-transformed continuous variable (Multivariate I), as a binary variable of present vs. absent (Multivariate II), or as an ordered categorical variable of abundance bins (Multivariate III).

Figure 23:
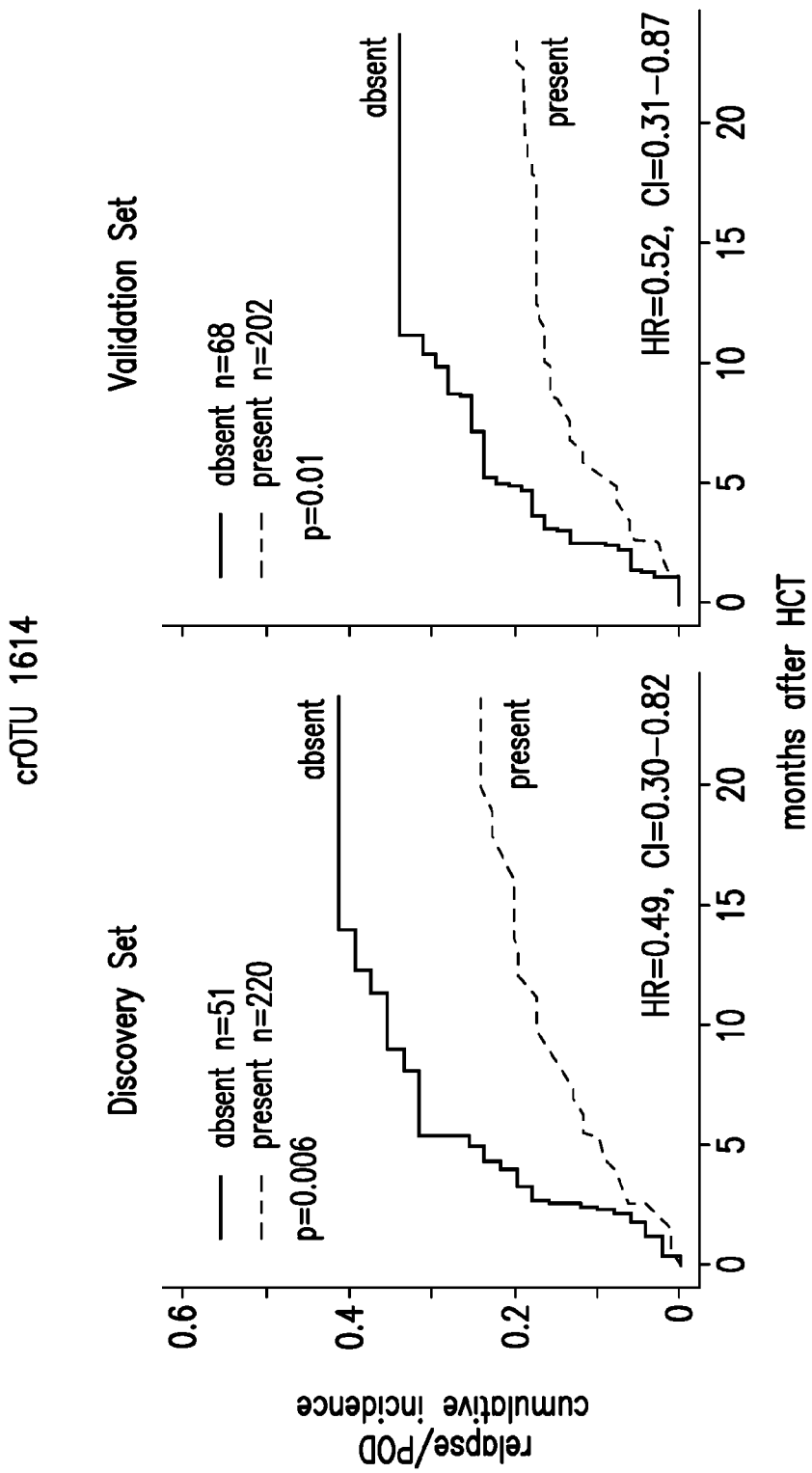

FIG. 23 shows that the cumulative incidence of relapse/POD in the discovery and validation sets is greater in the absence of crOTU 1614.

Figure 24:
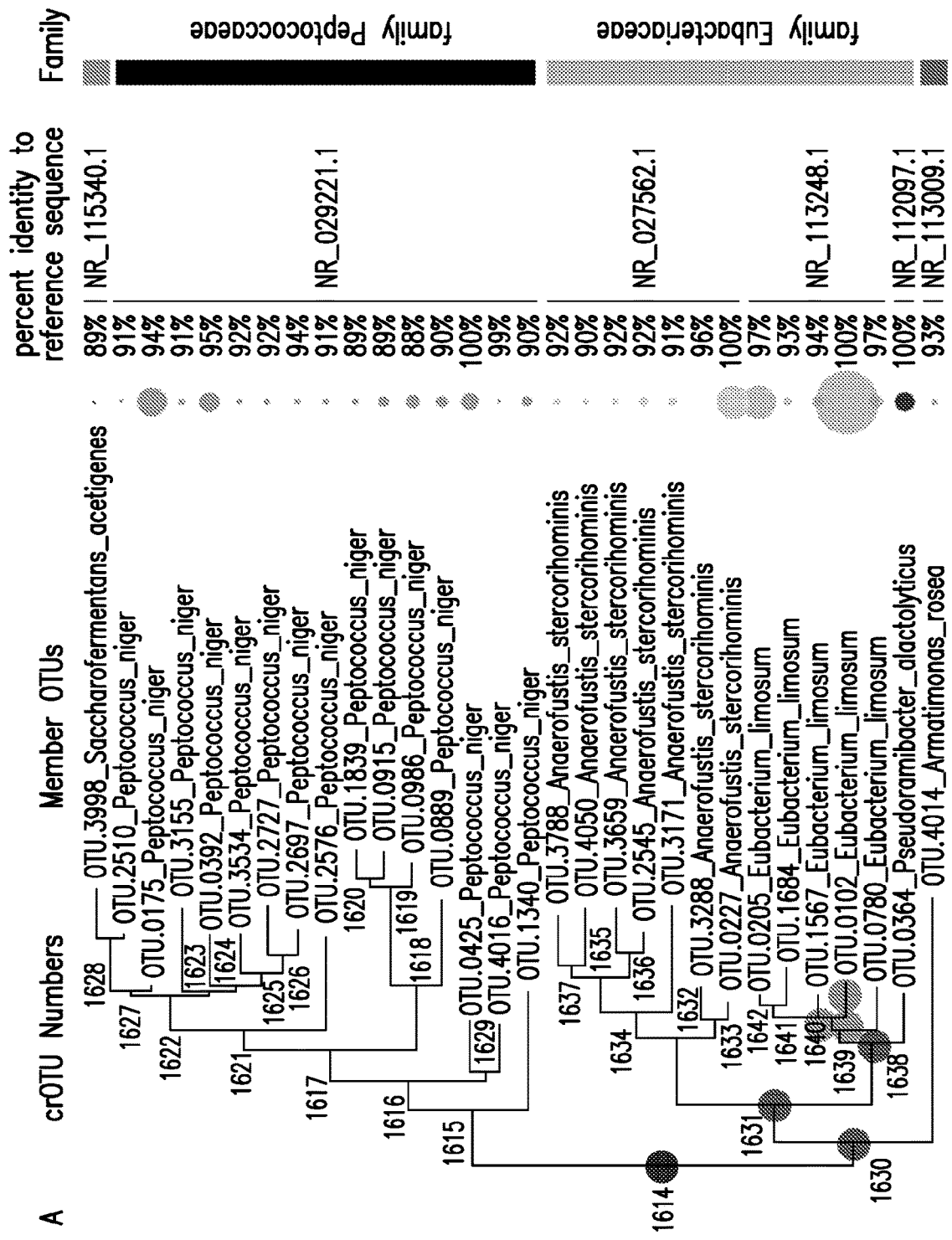
Figure 24:
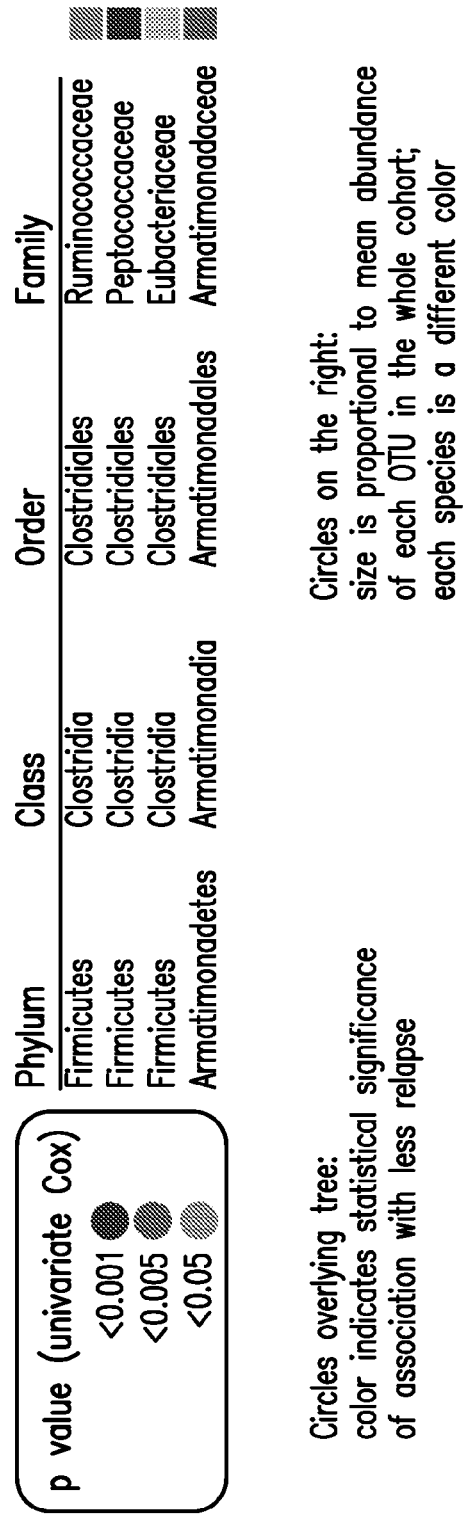

FIG. 24 provides a cladogram of crOTU 1614 depicting crOTUs (blue numbers) and OTUs. The percent identity to the NCBI 16S reference sequence and its accession number are listed. Bars on the right indicate taxonomic family membership. The small table at the bottom lists the taxonomic classification of the four main species in crOTU 1614.

FIG. 25 provides a pie chart of the relative contribution (mean abundance) of the four main species to the overall abundance of crOTU 1614 across all patients.

FIGS. 26A-B show that in the patient cohort of Example 3, when stratified by crOTU 1614 abundance, crOTU was associated with less cumulative risk of relapse/POD (FIG. 26A). FIG. 26B provides the mean abundance of crOTU 1614 (top) and cumulative incidence of relapse/POD at 2 years (bottom) in the four strata.

Figure 27:
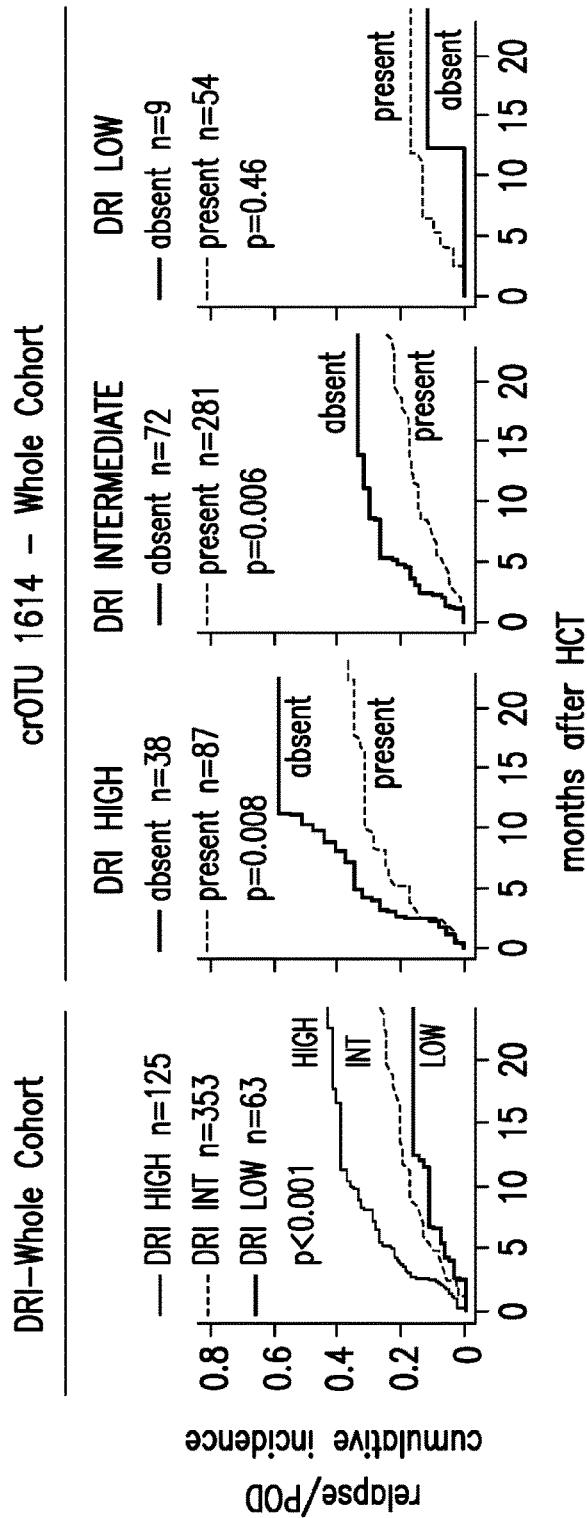

FIG. 27 shows that RDRI stratifies the relapse/POD risk of the patients in the cohort of Example 3.

Figure 28:
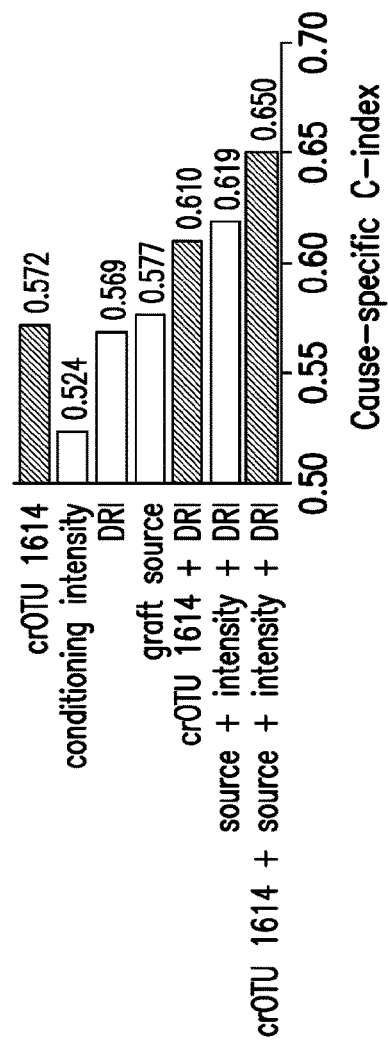

FIG. 28 provides cause-specific Concordance indices in the presence of competing risks for combinations of intestinal presence of crOTU 1614 with clinical risk factors for relapse/POD (i.e., RDRI, graft source, and conditioning intensity).

Figure 29:
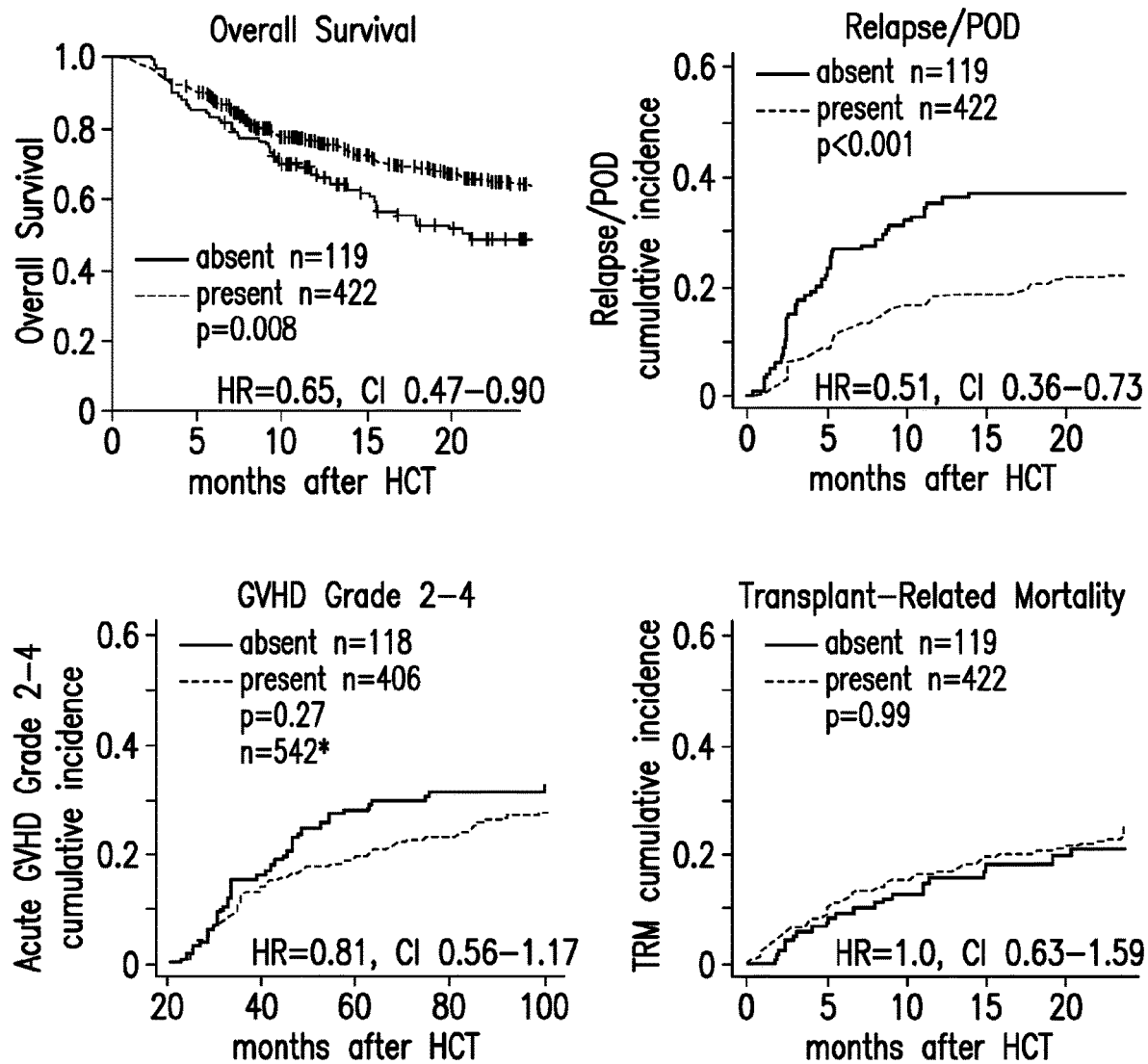

FIG. 29 shows the associations between the presence of crOTU 1614 in stool samples three weeks after allo-HCT and overall survival, cumulative incidence of relapse/POD, cumulative incidence of acute GVHD grade 2-4, and transplant-related mortality (TRM). Seventeen patients had developed GVHD Grade 2-4 prior to landmark day 21 and were excluded from this panel.

Figure 30:
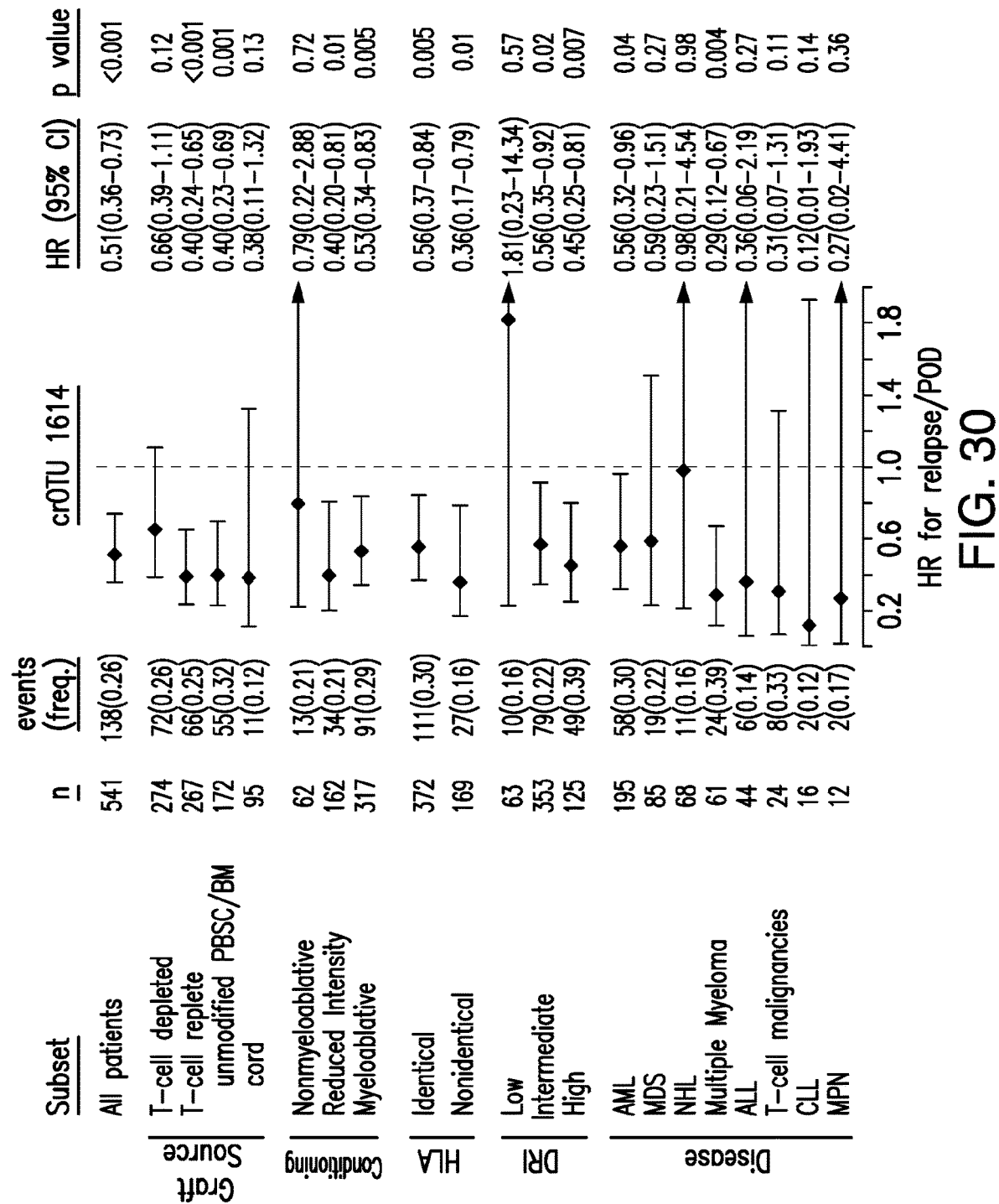

FIG. 30 depicts the association of crOTU 1614 presence with relapse/POD in patient subsets according to graft source, conditioning intensity, degree of HLA match, RDRI, and disease type, where the size of the grey box is proportional to number of patients in the subgroup.

Figure 31A:
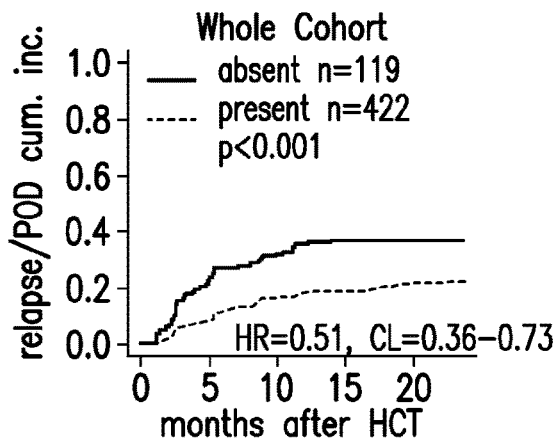
Figure 31B:
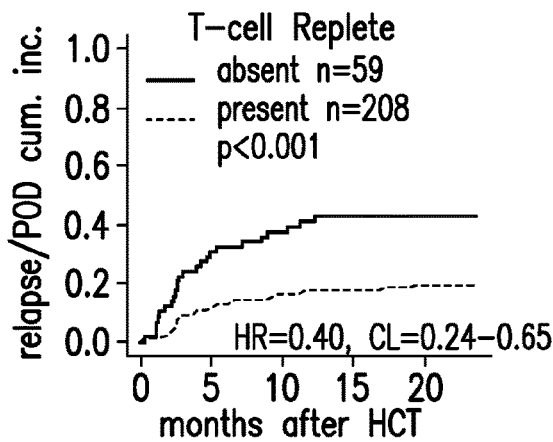
Figure 31C:
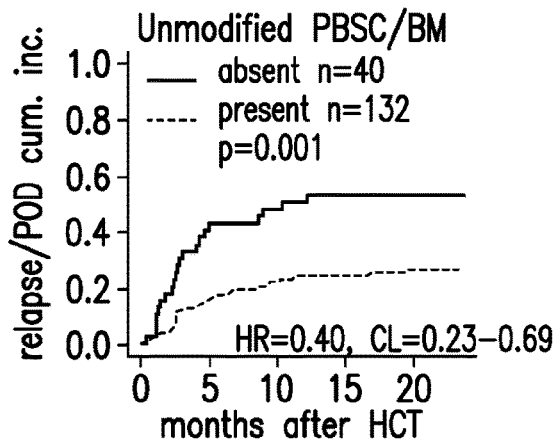
Figure 31D:
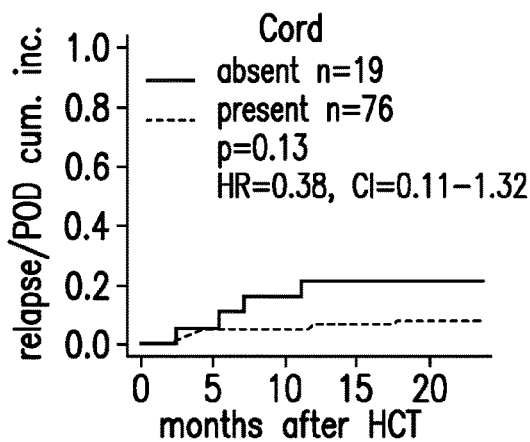
Figure 31E:
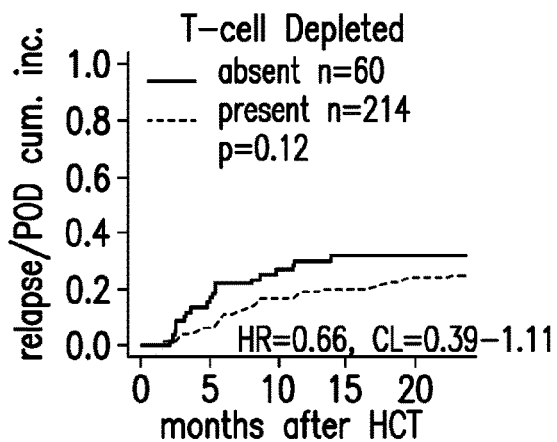

FIGS. 31A-E depict the cumulative incidence of relapse/POD according to presence of crOTU 1614 and graft source, where FIG. 31A is for the whole cohort, FIG. 31B is for T-cell replete grafts, FIG. 31C is for unmodified PBSC/BM (T-cell replete) grafts, FIG. 31D is for cord (T-cell replete) grafts, and FIG. 31E is for T-cell depleted grafts.

Figure 32:
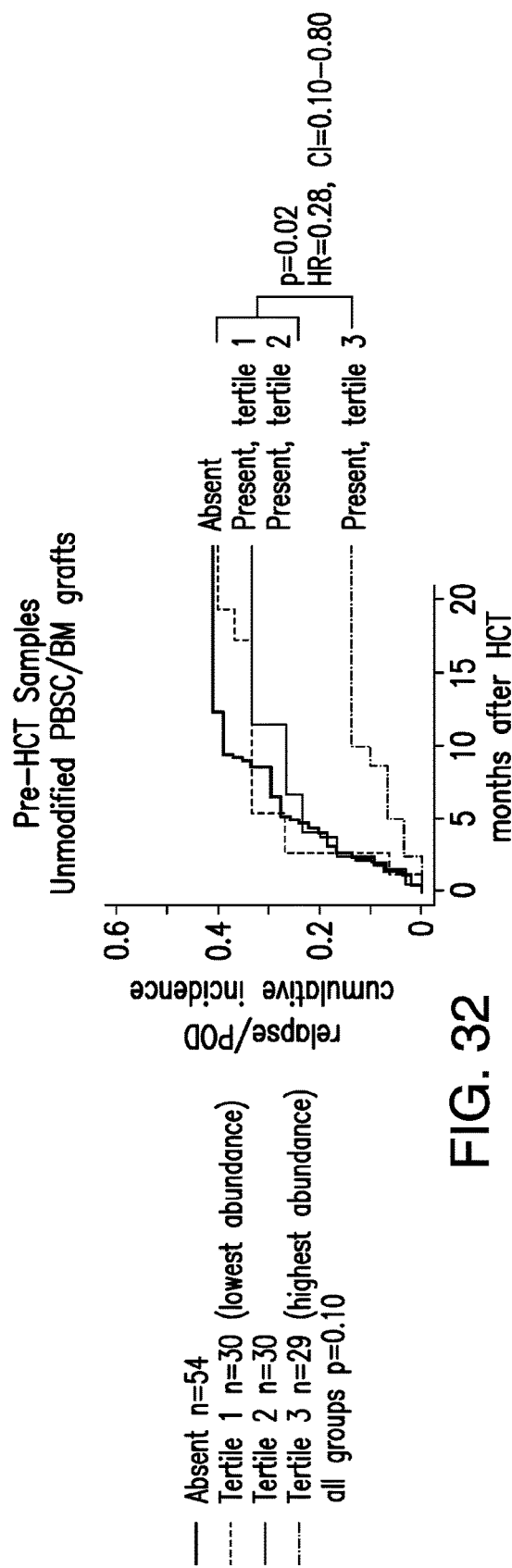

FIG. 32 shows the association between abundance of crOTU and relapse/POD for recipients of unmodified PBSC/BM grafts (n=143) based on a single sample collected per patient prior to allo-HCT (Pre-HCT).

Figure 33:
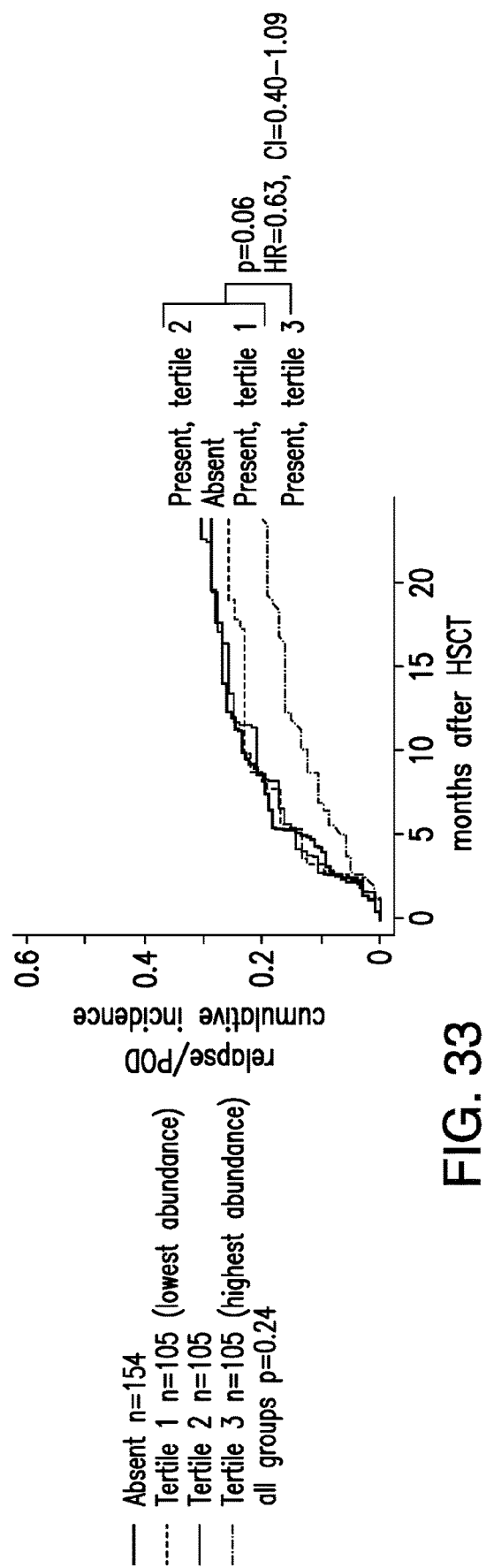

FIG. 33 shows the association between abundance of crOTU and relapse/POD for recipients of all graft sources (n=469) based on a single sample collected per patient before allo-HCT (Pre-HCT).

FIG. 34 shows the category boundaries for abundance bins used throughout the study, as depicted by FIGS. 26B, 26C, 32 and 33.

5. DETAILED DESCRIPTION OF THE INVENTION

The present invention relates to methods for determining the risk that a subject with cancer will experience a cancer relapse following treatment, for example, after allo-HSCT, and also to methods and compositions for reducing the risk of a cancer relapse, as well as to compositions and methods for increasing the likelihood that a subject will survive a cancer relapse. For clarity of description, and not by way of limitation, this section is divided into the following subsections:

(i) Methods of determining cancer relapse risk;
(ii) Therapeutic bacteria;
(iii) Recombinant cells;
(iv) Pharmaceutical compositions;
(v) Methods of treatment; and
(vi) Kits.

The following are terms relevant to the present invention:

An "individual" or "subject" or "patient" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

An "effective amount" of a substance as that term is used herein is that amount sufficient to effect beneficial or desired results, including clinical results, and, as such, an "effective amount" depends upon the context in which it is being applied. In the context of administering a composition to reduce the risk of cancer relapse, and/or administering a composition to reduce at least one sign or symptom of a cancer relapse, an effective amount of a composition described herein is an amount sufficient to treat and/or ameliorate a cancer relapse, as well as decrease the symptoms and/or reduce the likelihood of a cancer relapse. The decrease can be a 10%, 20%, 30%, 40%, 50%, 60%, 70%, 80%, 90%, 95%, 98% or 99% decrease in severity of symptoms of cancer relapse, or likelihood of cancer relapse. An effective amount is administered in one or more administrations.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more signs or symptoms, diminishment of extent of disease, stabilized (i.e., not worsening) state of disease, prevention of disease, delay or slowing of disease progression, remission of the disease (e.g., cancer remission) and/or amelioration or palliation of the disease state. The decrease can be a 10%, 20%, 30%, 40%, 50%, 60%, 70%, 80%, 90%, 95%, 98% or 99% decrease in severity of complications, signs or symptoms. "Treatment" can also mean prolonging survival as compared to expected survival if not receiving treatment. Treatment" can also refer to decreasing the likelihood of cancer relapse.

The term "expression vector" is used to denote a nucleic acid molecule that is either linear or circular, into which another nucleic acid sequence fragment of appropriate size can be integrated. Such nucleic acid fragment(s) can include additional segments that provide for transcription of a gene encoded by the nucleic acid sequence fragment. The additional segments can include and are not limited to: promoters, transcription terminators, enhancers, internal ribosome entry sites, untranslated regions, polyadenylation signals, selectable markers, origins of replication and such, as known in the art. Expression vectors are often derived from plasmids, cosmids, viral vectors and yeast artificial chromosomes; vectors are often recombinant molecules containing nucleic acid sequences from several sources.

The term "operably linked," when applied to nucleic acid sequences, for example in an expression vector, indicates that the sequences are arranged so that they function cooperatively in order to achieve their intended purposes, i.e., a promoter sequence allows for initiation of transcription that proceeds through a linked coding sequence as far as the termination signal.

A "nucleic acid molecule" is a single or double stranded covalently-linked sequence of nucleotides in which the 3' and 5' ends on each nucleotide are joined by phosphodiester bonds. The polynucleotide can be made up of deoxyribonucleotide bases or ribonucleotide bases. Polynucleotides include DNA and RNA, and can be manufactured synthetically in vitro or isolated from natural sources.

The term "promoter" as used herein denotes a region within a gene to which transcription factors and/or RNA polymerase can bind so as to control expression of an associated coding sequence. Promoters are commonly, but not always, located in the 5' non-coding regions of genes, upstream of the translation initiation codon. The promoter region of a gene can include one or more consensus sequences that act as recognizable binding sites for sequence specific nucleic acid binding domains of nucleic acid binding proteins. Nevertheless, such binding sites can also be located in regions outside of the promoter, for example in enhancer regions located in introns or downstream of the coding sequence.

A "regulatory gene" is a gene involved in controlling the expression of one or more other genes.

A "cluster," or "cluster of related bacteria" can include two or more bacterial species or strains that are related by rRNA sequences, for example 16S rRNA (e.g., a variable region of the 16S rDNA sequence, such as V1, V2, V3, V4 or V5), similarity, and/or evolutionary distance. For example, in a phylogenetic tree in which the nodes (branch points) are defined as the clusters, the OTUs at the tips of the tree subsidiary to a given node defines the members of such a cluster. Such clusters can alternatively be termed "clusters of related operational taxonomic units" or "crOTUs." In certain non-limiting embodiments, the bacterial species in a crOTU exhibit less than or equal to 70%, 75%, 80%, 85%, 90%, 95%, 97%, 99%, or 100% 16S rRNA identity. In certain non-limiting embodiments, the bacterial species in a crOTU exhibit at least 70%, 75%, 80%, 85%, 90%, 95%, 97%, 99%, or 100% 16S rRNA identity.

In certain non-limiting embodiments, the bacterial species in a crOTU comprise an identity to one or more nucleic acid sequences described by any one of SEQ ID NOS:1-12 or SEQ ID NOS: 1-17 wherein the level of identity is between about 80 and 100%, 85 and 100%, 90 and 100%, 95 and 100%, 97 and 100%, 80 and 97%, 80 and 95%, 80 and 90%, 80 and 85%, and values in between, for example, about 80, 81, 82, 83, 84, 85, 86, 87, 88, 89, 90, 91, 92, 93, 94, 95, 96, 97, 98, 99 or 100%. In some embodiments, the level of identity is between (inclusive) 80 and 100%, 85 and 100%, 90 and 100%, 95 and 100%, 97 and 100%, 80 and 97%, 80 and 95%, 80 and 90%, 80 and 85%, and values in between, for example, 80, 81, 82, 83, 84, 85, 86, 87, 88, 89, 90, 91, 92, 93, 94, 95, 96, 97, 98, 99 or 100%. In certain non-limiting embodiments, the percent identity corresponds to the V4-V5 variable region of any one of SEQ ID NOS:1-12 or SEQ ID NOS: 1-17.

In certain non-limiting embodiments, the bacterial species in a crOTU are determined by relatedness of OTU sequences based on minimum-evolution subtree-pruning-regrafting (SPRs) and maximum-likelihood nearest-neighbor interchanges (NNIs), as described by Price et al., PLoS One. 2010; 5(3): e9490, which is incorporated by reference in its entirety herein.

A "probiotic" is a microorganism or group of microorganisms that provides health benefits, or that is non-pathogenic, to a subject when consumed, ingested, or otherwise administered to a subject, for example, a reduction in the likelihood of relapse following cancer treatment. As used herein, the term probiotic can be used to describe, for example, probiotic bacteria and/or a probiotic yeast, and can include the bacteria described herein as well as other bacteria.

A "prebiotic" is a substance that promotes the growth, proliferation and/or survival of one or more bacteria or yeast. As used herein, the term prebiotic can be used to describe, for example, a nutritional supplement including plant fiber, or one or more of poorly-absorbed complex carbohydrates, oligosaccharides, inulin-type fructans or arabinoxylans.

A "postbiotic" is a substance derived from a probiotic organism. As used herein, the term postbiotic can be used to describe, for example, a protein expressed by one or more bacteria or yeast, a metabolic product of one or more bacteria or yeast, or media from a culture of one or more strains of bacteria or yeast.

As used herein, the term "cancer relapse" refers to a return or recurrence of cancer, or the signs and symptoms of cancer, after a period of improvement, for example, after a period of reduction in the presence of cancer, or the signs and symptoms thereof, following treatment. In certain non-limiting embodiments, "cancer relapse" refers to a return or recurrence of cancer, or the signs and symptoms thereof, after a period of improvement of at least 1, 2, 3, 4, 5, 6, 7, 8, 9, 10 or more weeks, or at least 1, 2, 3, 4, 5, 6, 7, 8, 9, 10, 12, 12 months or more, or at least 1, 2, 3, 4, 5, 6, 7, 8, 9, 10 years or more. In certain embodiments, the period of improvement is between about 3 weeks and 2 years.

In certain non-limiting embodiments, cancer relapse is determined by measuring time to relapse or progression of disease (POD) by disease-specific criteria. Detection of minimal residual disease is scored as a relapse/POD event when flow cytometry, radiographic, or molecular results are acted upon clinically by initiation of therapy, infusion of donor lymphocytes, or withdrawal of immunosuppression.

5.1 Methods of Determining Cancer Relapse Risk

In certain non-limiting embodiments, the present invention provides for methods of determining whether a subject diagnosed with cancer is at greater or reduced risk for having a cancer relapse following a cancer treatment.

In certain non-limiting embodiments, a subject determined to be at a greater risk for cancer relapse is monitored more frequently and for an extended period of time for relapse following treatment, and can be administered therapeutic regimens in addition to, or as an alternative to, a hematopoietic stem cell transplantation, as described further herein.

Non-limiting examples of cancer include, but are not limited to, acute leukemia, chronic leukemia, lymphoid malignancies, plasma cell disorders, and myeloproliferative neoplasms.

In certain non-limiting embodiments, the cancer treatment comprises hematopoietic stem cell transplantation (HSCT). In certain non-limiting embodiments, the hematopoietic stem cell transplant comprises allogeneic stem cells from a donor that is different than the treated patient (allo-HSCT). In certain non-limiting embodiments, the hematopoietic stem cell transplant comprises autologous stem cells from the patient being treated.

In certain non-limiting embodiments, the cancer treatment comprises an allogenic cord blood transplant, or allogenic cord stem cell transplant.

In certain non-limiting embodiments, the cancer treatment comprises a T-cell replete transplant or a T-cell depleted transplant.

In certain non-limiting embodiments, the cancer treatment comprises a bone marrow transplant.

In certain non-limiting embodiments, the methods comprise determining the abundance of a species of bacteria, OTU, or cluster (also referred to herein as "bacterium") in an intestinal microbiota sample of the subject that is indicative of a reduced risk of cancer relapse. In certain non-limiting embodiments, the bacteria is selected from the group consisting of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria.

In certain non-limiting embodiments, the bacteria detected is *Eubacterium limosum, Peptococcus niger, Anaerofustis stercorihominis, Pseudoramibacter alactolyticus, Saccharofermentans acetigenes, Armatimonas rosea*, a combination thereof, or a cluster comprising any one or more of the foregoing bacteria.

In certain non-limiting embodiments, the bacteria detected is *Eubacterium limosum*, or a cluster comprising *Eubacterium limosum*.

In certain non-limiting embodiments, the bacteria detected is *Parvimonas micra, Finegoldia magna, Levyella massiliensis, Gallicola barnesae, Murdochiella asaccharolytica, Eubacterium brachy*, a combination thereof, or a cluster comprising any one or more of the foregoing bacteria.

In certain non-limiting embodiments, the bacteria are detected prior to treating the subject, for example, prior to a HSCT.

In certain non-limiting embodiments, the bacteria are detected after treating the subject, for example, after a HSCT. In certain non-limiting embodiments, when the bacteria are detected post-treatment, detection of any level of one or more of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, is indicative of a reduced risk of cancer relapse In certain non-limiting embodiments, detecting an abundance of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, in the subject that is greater than the abundance of said bacteria in an intestinal microbiota sample of a second subject that has had a cancer relapse following cancer therapy is indicative of a reduced risk of cancer relapse.

In certain non-limiting embodiments, detecting an abundance of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, in the subject that is greater than the abundance of said bacteria in an intestinal microbiota sample of a second subject that has not had a cancer relapse following cancer therapy is indicative of a reduced risk of cancer relapse.

In certain non-limiting embodiments, detecting an abundance of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, in the subject that is lower than the abundance of said bacteria in an intestinal microbiota sample of a second subject that has had a cancer relapse following cancer therapy is indicative of greater risk of cancer relapse.

In certain non-limiting embodiments, detecting an abundance of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, in the subject that is lower than the abundance of said bacteria in an intestinal microbiota sample of a second subject that has not had a cancer relapse following cancer therapy is indicative of greater risk of cancer relapse.

In certain non-limiting embodiments, the methods of the present invention comprise determining the abundance of one more bacteria present in an intestinal microbiota sample of a subject, for example, *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, wherein the subject is diagnosed or identified as having a reduced risk of a cancer relapse, when the abundance or amount of the one or more bacteria in the subject's microbiota is greater than a bacteria reference level. In some non-limiting embodiments, a bacteria reference level is an abundance of bacteria, for example, *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, present in intestinal microbiota, a level above which is indicative of reduced risk of cancer relapse, as determined by a medical doctor or person of skill in the art.

In one non-limiting example, such a reference level is the abundance of said bacteria in the microbiota of a subject with cancer who has not had, or has a reduced risk for, a cancer relapse.

In certain non-limiting embodiments, such a reference level is the abundance of said bacteria in the microbiota of a healthy subject who has not been diagnosed with cancer, or has a reduced risk for having cancer.

In certain non-limiting embodiments, such a reference level is the percent of the total abundance of bacteria in a subject's intestinal microbiota sample comprising the one more bacteria described herein, or cluster comprising said one or more bacteria. In certain non-limiting embodiments, the reference bacterial level is between about 0.10 and 50%, between about 0.15 and 45%, between about 0.5 and 40%, between about 1 and 35%, between about 1.5 and 30%, between about 2 and 30%, between about 2.5 and 25%, between about 3 and 20%, between about 3.5 and 15%, between about 4 and 10%, between about 4.5 and 8%, between about 5 and 6%, and values in between.

In certain non-limiting embodiments, the methods of the present invention comprise determining the abundance of one more bacteria present in an intestinal microbiota sample of a subject, for example, *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, wherein the subject is diagnosed or identified as having a greater risk of a cancer relapse, when the abundance or amount of the one or more bacteria in the subject's microbiota is lower than a bacteria reference level. In some non-limiting embodiments, a bacteria reference level is an abundance of bacteria, for example, *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, present in intestinal microbiota, a level below which is indicative of greater risk of cancer relapse, as determined by a medical doctor or person of skill in the art.

In one non-limiting example, such a reference level can be the abundance of said bacteria in the microbiota of a subject with cancer who has had, or has a greater risk for, a cancer relapse.

In certain non-limiting embodiments, the methods of the present invention comprise determining the abundance of bacteria in an intestinal microbiota sample of a subject that is indicative of an increased risk of cancer relapse. In certain non-limiting embodiments, the bacteria is *Enterococcus faecium*.

In certain non-limiting embodiments, detecting an abundance of *Enterococcus faecium* in the subject that is greater than the abundance of said bacteria in an intestinal microbiota sample of a second subject that has had a cancer relapse following cancer therapy is indicative of an increased risk of cancer relapse.

In certain non-limiting embodiments, detecting an abundance of *Enterococcus faecium* in the subject that is greater than the abundance of said bacteria in an intestinal microbiota sample of a second subject that has not had a cancer relapse following cancer therapy is indicative of an increased risk of cancer relapse.

In certain non-limiting embodiments, detecting an abundance of *Enterococcus faecium* in the subject that is lower than the abundance of said bacteria in an intestinal microbiota sample of a second subject that has had a cancer relapse following cancer therapy is indicative of a reduced risk of cancer relapse.

In certain non-limiting embodiments, detecting an abundance of *Enterococcus faecium* in the subject that is lower than the abundance of said bacteria in an intestinal microbiota sample of a second subject that has not had a cancer relapse following cancer therapy is indicative of a reduced risk of cancer relapse.

In certain non-limiting embodiments, the methods of the present invention comprise determining the abundance of *Enterococcus faecium* bacteria present in an intestinal microbiota sample of a subject, wherein the subject is diagnosed or identified as having an increased risk of a cancer relapse, when the abundance or amount of the *Enterococcus faecium* in the subject's microbiota is greater than a bacteria reference level. In some non-limiting embodiments, a bacteria reference level is an abundance of *Enterococcus faecium* bacteria, present in intestinal microbiota, a level above which is indicative of being at greater risk of cancer relapse, as determined by a medical doctor or person of skill in the art.

In one non-limiting example, such a reference level can be the abundance of said bacteria in the microbiota of a subject with cancer who has had, or has an increased risk for, a cancer relapse.

In certain non-limiting embodiments, the methods of the present invention comprise determining the abundance of *Enterococcus faecium* bacteria present in an intestinal microbiota sample of a subject, wherein the subject is diagnosed or identified as having a reduced risk of a cancer relapse, when the abundance or amount of the *Enterococcus faecium* in the subject's microbiota is less than a bacteria reference level. In some non-limiting embodiments, a bacteria reference level is an abundance of *Enterococcus faecium* bacteria, present in intestinal microbiota, a level below which is indicative of being at a reduced risk of cancer relapse, as determined by a medical doctor or person of skill in the art.

In one non-limiting example, such a reference level can be the abundance of said bacteria in the microbiota of a subject with cancer who has not had, or has reduced risk for, a cancer relapse.

In one non-limiting example, such a reference level can be the abundance of said bacteria in the microbiota of a healthy subject who has not been diagnosed with cancer, or has a reduced risk for having cancer.

In certain non-limiting embodiments, the bacteria is a cluster of bacteria comprising *Eubacterium limosum*. Such a cluster of bacteria can comprise species from the Eubacteriaceae and Peptococcaceae families, including, but not limited to *Anaerofustis stercorihominis*, *Pseudoramibacter alactolyticus*, and *Peptococcus niger*. In certain non-limiting embodiments, the cluster can further include *Armatimonas rosea* and/or *Saccharofermentans acetigenes*. In certain non-limiting embodiments, the cluster can comprise greater than about 40%, greater than about 50%, greater than about 60%, or greater than about 65% *Eubacterium limosum*. In certain non-limiting embodiments, the cluster can include from about 10% to about 20% of each of *Anaerofustis stercorihominis* and *Peptococcus niger*.

In certain non-limiting embodiments, the methods of the present invention comprise determining the abundance of a cluster of bacteria comprising *Eubacterium limosum* present in an intestinal microbiota sample of a subject, wherein the subject is diagnosed or identified as having a decreased risk of a cancer relapse, when the abundance or amount of the cluster of bacteria comprising *Eubacterium limosum* in the subject's microbiota is greater than a bacteria reference level. In some non-limiting embodiments, a bacteria reference level is an abundance of cluster of bacteria comprising *Eubacterium limosum*, present in intestinal microbiota, a level above which is indicative of being at lesser risk of cancer relapse, as determined by a medical doctor or person of skill in the art. In one non-limiting example, such a reference level can be the abundance of said bacteria in the microbiota of a subject with cancer who has had, or has a decreased risk for, a cancer relapse.

In certain non-limiting embodiments, the methods of the present invention comprise determining the abundance of a cluster of bacteria comprising *Eubacterium limosum* present in an intestinal microbiota sample of a subject, wherein the subject is diagnosed or identified as having an increased risk of a cancer relapse, when the abundance or amount of the cluster of bacteria comprising *Eubacterium limosum* in the subject's microbiota is less than a bacteria reference level. In some non-limiting embodiments, a bacteria reference level is an abundance of cluster of bacteria comprising *Eubacterium limosum*, present in intestinal microbiota, a level below which is indicative of being at an increased risk of cancer relapse, as determined by a medical doctor or person of skill in the art.

In certain non-limiting embodiments, the microbiota sample is a fecal sample or an intestinal content sample, for example, a rectal swab.

In certain non-limiting embodiments, the abundance or amount of bacteria present in a sample is determined by measuring the abundance or amount of bacterial nucleic acid present in the sample, for example, 16S rRNA.

In certain non-limiting embodiments, the abundance or amount of bacteria present in a sample is determined by shotgun sequencing of bacterial DNA, PCR amplification of specific genes carried by the bacteria, quantitative PCR of transcripts expressed specifically by the bacteria, antibody based methods of bacterial detection, metabolomic detection of bacterial metabolites, proteomic detection of bacterial proteins, and/or by methods of culturing the microbiota sample.

In certain non-limiting embodiments, the microbiota sample is collected from the subject up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days after the subject has received cancer treatment, for example, allo-HSCT. In certain non-limiting embodiments, the microbiota sample is collected from the subject up to 1, 2, 3, 4 or more weeks, or up to 1, 2, 3, 4, 5, 6, 7, 8, 9, 10, 11, 12 or more months, after the subject has received a cancer treatment. In certain non-limiting embodiments, the microbiota sample is collected from the subject up to 1, 2, 3, 4, 5, 6, 7 or more days, or up to 1, 2, 3, 4 or more weeks, or up to 1, 2, 3, 4, 5, 6, 7, 8, 9, 10, 11, 12 or more months, before the subject receives a cancer treatment.

5.2 Therapeutic Bacteria

In certain non-limiting embodiments, the compositions described herein comprise one or more therapeutic bacteria, or spores thereof, for example, a *Streptococcus anginosus* (e.g., 33397), *Parvimonas micra* (e.g., ATCC 33270), *Acidaminococcus intestini* (e.g., DSM 21505), *Eubacterium limosum* (e.g., ATCC 8486), *Clostridium glycyrrhizinilyticum* (e.g., JCM 13369), *Desulfosporosinus lacus* (e.g., DSM 15449), *Eubacterium biforme* (e.g., DSM 3989), *Anaerofustis stercorihominis* (e.g., DSM 17244), *Pseudoramibacter alactolyticus* (e.g., ATCC 23263), *Peptococcus niger* (e.g., DSM 20475), *Armatimonas rosea* (e.g., DSM 23562), *Saccharofermentans acetigenes* (e.g., JCM 14006), *Finegoldia magna* (e.g., ATCC 29328), *Levyella massiliensis*, *Gallicola barnesae* (e.g., ATCC 49795), *Murdochiella asaccharolytica* (e.g., ATCC BAA-1631), *Eubacterium brachy* (e.g., ATCC 33089), a combination thereof, or a cluster comprising any one or more of the foregoing bacteria.

In certain non-limiting embodiments, the one or more therapeutic bacteria comprise *Streptococcus anginosus*, for example, having ATCC (American Type Culture Collection) No. 33397, or bacteria having at least 90%, at least 95%, at least 97%, or at least 99% identity with one or more 16S rDNA sequences, for example, as described by GenBank Accession number NR_118289.1 (SEQ ID NO:13), or a variable region of one or more 16S rDNA sequences such as the V4 region, from said *Streptococcus anginosus*.

In certain non-limiting embodiments, the one or more therapeutic bacteria comprise *Parvimonas micra*, for example, having the ATCC No. 33270, or bacteria having at least 90%, at least 95%, at least 97%, or at least 99% identity with one or more 16S rDNA sequences, for example, as described by GenBank Accession number NR_114338.1 (SEQ ID NO:12), or a variable region of one or more 16S rDNA sequences such as the V4 region, from said *Parvimonas micra*.

In certain non-limiting embodiments, the one or more therapeutic bacteria comprise *Eubacterium limosum*, for example, having the ATCC No. 8486, 51976, or 10825, or bacteria having at least 90%, at least 95%, at least 97%, or at least 99% identity with one or more 16S rDNA sequences, for example, as described by GenBank Accession number NR_113248.1 (SEQ ID NO:1), or a variable region of one or more 16S rDNA sequences such as the V4 region, from said *Eubacterium limosum*.

In certain non-limiting embodiments, the one or more therapeutic bacteria comprise *Eubacterium biforme*, for example, having the ATCC No. 27806, or bacteria having at least 90%, at least 95%, at least 97%, or at least 99% identity with one or more 16S rDNA sequences, for example, as described by GenBank Accession number NR_044731.2 (SEQ ID NO:14), or a variable region of one or more 16S rDNA sequences such as the V4 region, from said *Eubacterium biforme*.

In certain non-limiting embodiments, the one or more therapeutic bacteria comprise *Acidaminococcus intestini*, for example, having DSMZ (Leibniz-Institut DSMZ—Deutsche Sammlung von Mikroorganismen und Zellkulturen GmbH) deposit number DSM No. 21505, or bacteria having at least 90%, at least 95%, at least 97%, or at least 99% identity with one or more 16S rDNA sequences, for example, as described by GenBank Accession number NR_041894.1 (SEQ ID NO:15), or a variable region of one or more 16S rDNA sequences such as the V4 region, from said *Acidaminococcus intestini*.

In certain non-limiting embodiments, the one or more therapeutic bacteria comprise *Clostridium glycyrrhizinilyticum*, for example, having DSMZ deposit number DSM No. 17593, or bacteria having at least 90%, at least 95%, at least 97%, or at least 99% identity with one or more 16S rDNA sequences, for example, as described by GenBank Accession number NR_112553.1 (SEQ ID NO:16), or a variable region of one or more 16S rDNA sequences such as the V4 region, from said *Clostridium glycyrrhizinilyticum*.

In certain non-limiting embodiments, the one or more therapeutic bacteria comprise *Desulfosporosinus lacus*, for example, having DSMZ deposit number DSM No. 15449, or bacteria having at least 90%, at least 95%, at least 97%, or at least 99% identity with one or more 16S rDNA sequences, for example, as described by GenBank Accession number NR_042202.1 (SEQ ID NO:17), or a variable region of one or more 16S rDNA sequences such as the V4 region, from said *Desulfosporosinus lacus*.

In certain non-limiting embodiments, the one or more therapeutic bacteria comprise *Anaerofustis stercorihominis*, for example, having DSMZ deposit number DSM No. 17244, or bacteria having at least 90%, at least 95%, at least 97%, or at least 99% identity with one or more 16S rDNA sequences, for example, as described by GenBank Accession number NR_027562.1 (SEQ ID NO:3), or a variable region of one or more 16S rDNA sequences such as the V4 region, from said *Anaerofustis stercorihominis*.

In certain non-limiting embodiments, the one or more therapeutic bacteria comprise *Pseudoramibacter alactolyticus*, for example, having ATCC No. 23263, or bacteria having at least 90%, at least 95%, at least 97%, or at least 99% identity with one or more 16S rDNA sequences, for example, as described by GenBank Accession number NR_112097.1 (SEQ ID NO:6), or a variable region of one or more 16S rDNA sequences such as the V4 region, from said *Pseudoramibacter alactolyticus*.

In certain non-limiting embodiments, the one or more therapeutic bacteria comprise *Peptococcus niger*, for example, having DSMZ deposit number DSM No. 20475, or bacteria having at least 90%, at least 95%, at least 97%, or at least 99% identity with one or more 16S rDNA sequences, for example, as described by GenBank Accession number NR_029221.1 (SEQ ID NO:2), or a variable region of one or more 16S rDNA sequences such as the V4 region, from said *Peptococcus niger*.

In certain non-limiting embodiments, the one or more therapeutic bacteria comprise *Armatimonas rosea*, for example, having DSMZ deposit number DSM No. 23562, or bacteria having at least 90%, at least 95%, at least 97%, or at least 99% identity with one or more 16S rDNA sequences, for example, as described by GenBank Accession number NR_113009.1 (SEQ ID NO:5), or a variable region of one or more 16S rDNA sequences such as the V4 region, from said *Armatimonas rosea*.

In certain non-limiting embodiments, the one or more therapeutic bacteria comprise *Saccharofermentans acetigenes*, for example, having Japan Collection of Microorganisms (JCM) No. 14006, or bacteria having at least 90%, at least 95%, at least 97%, or at least 99% identity with one or more 16S rDNA sequences, for example, as described by GenBank Accession number NR_115340.1 (SEQ ID NO:4), or a variable region of one or more 16S rDNA sequences such as the V4 region, from said *Saccharofermentans acetigenes*.

In certain non-limiting embodiments, the one or more therapeutic bacteria comprise *Finegoldia magna*, for example, having ATCC No. 29328, or bacteria having at least 90%, at least 95%, at least 97%, or at least 99% identity with one or more 16S rDNA sequences, for example, as described by GenBank Accession number NR_113383.1 (SEQ ID NO:7), or a variable region of one or more 16S rDNA sequences such as the V4 region, from said *Finegoldia magna*.

In certain non-limiting embodiments, the one or more therapeutic bacteria comprise *Levyella massiliensis*, or bacteria having at least 90%, at least 95%, at least 97%, or at least 99% identity with one or more 16S rDNA sequences, for example, as described by GenBank Accession number NR_133039.1 (SEQ ID NO:9), or a variable region of one or more 16S rDNA sequences such as the V4 region, from said *Levyella massiliensis*.

In certain non-limiting embodiments, the one or more therapeutic bacteria comprise *Gallicola barnesae*, for example, having ATCC No. 49795, or bacteria having at least 90%, at least 95%, at least 97%, or at least 99% identity with one or more 16S rDNA sequences, for example, as described by GenBank Accession number NR_040843.1 (SEQ ID NO:10), or a variable region of one or more 16S rDNA sequences such as the V4 region, from said *Gallicola barnesae*.

In certain non-limiting embodiments, the one or more therapeutic bacteria comprise *Murdochiella asaccharolytica*, for example, having ATCC No. BAA-1631, or bacteria having at least 90%, at least 95%, at least 97%, or at least 99% identity with one or more 16S rDNA sequences, for example, as described by GenBank Accession number NR_116331.1 (SEQ ID NO:8), or a variable region of one or more 16S rDNA sequences such as the V4 region, from said *Murdochiella asaccharolytica*.

In certain non-limiting embodiments, the one or more therapeutic bacteria comprise *Eubacterium brachy*, for example, having ATCC No. ATCC 33089, or bacteria having at least 90%, at least 95%, at least 97%, or at least 99% identity with one or more 16S rDNA sequences, for example, as described by GenBank Accession number NR_118779.1 (SEQ ID NO:11), or a variable region of one or more 16S rDNA sequences such as the V4 region, from said *Eubacterium brachy*.

In various non-limiting embodiments of the invention, bacteria may be administered in the vegetative or dormant state, or as spores, or a mixture thereof.

In certain non-limiting embodiments, the therapeutic bacteria described herein can be modified, for example, by introducing one or more exogenous nucleic acids into the bacteria, thereby producing recombinant bacteria. Such nucleic acids can comprise, for example, an antibiotic resistance gene and/or an antibiotic susceptibility gene. Such recombinant bacteria can be prepared as described herein.

In certain non-limiting embodiments, *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, may be administered in the form of purified bacteria or spores or other progenitors thereof, or alternatively may be administered as a constituent in a mixture of types of bacteria, optionally including one or more species or cluster of additional bacteria, for example, probiotic bacteria, a probiotic yeast, prebiotic, postbiotic and/or antibiotic.

In non-limiting embodiments, the present invention provides for pharmaceutical compositions, and therapeutic uses thereof, as described herein, comprising such forms of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, and optionally including one or more species or cluster of additional bacteria, for example, probiotic bacteria, a probiotic yeast, prebiotic, postbiotic and/or antibiotic. Bacteria may be administered in the form of a liquid, a suspension, a dried (e.g., lyophilized) powder, a tablet, a capsule, or a suppository, and may be administered orally, nasogastrically, or rectally. In certain non-limiting embodiments, the bacteria is administered in a food product, for example, a yogurt food product. In certain non-limiting embodiments, a "food product" means a product or composition that is intended for consumption by a human or a non-human animal. Such food products include any food, feed, snack, food supplement, liquid, beverage, treat, toy (chewable and/or consumable toys), meal substitute or meal replacement.

In certain non-limiting embodiments, the present invention provides for a composition comprising an isolated *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria. In some non-limiting embodiments, the bacteria is in a formulation for administration to a subject.

In other non-limiting embodiments, the composition comprises one, two, three, four, five, six, seven, eight, nine, ten, eleven, twelve, thirteen, fourteen, fifteen, or sixteen bacteria selected from the group consisting of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica* and *Eubacterium brachy*.

In certain non-limiting embodiments, the present invention provides for a composition comprising an isolated *Streptococcus anginosus* bacteria, an isolated *Parvimonas micra* bacteria, an isolated *Acidaminococcus intestini* bacteria, an isolated *Eubacterium limosum* bacteria, an isolated *Clostridium glycyrrhizinilyticum* bacteria, an isolated *Desulfosporosinus lacus* bacteria, an isolated *Eubacterium biforme* bacteria, an isolated *Anaerofustis stercorihominis* bacteria, an isolated *Pseudoramibacter alactolyticus* bacteria, an isolated *Peptococcus niger* bacteria, an isolated *Armatimonas rosea* bacteria, an isolated *Saccharofermentans acetigenes* bacteria, an isolated *Finegoldia magna* bacteria, an isolated *Levyella massiliensis* bacteria, an isolated *Gallicola barnesae* bacteria, an isolated *Murdochiella asaccharolytica* bacteria, and/or an isolated *Eubacterium brachy* bacteria.

In some non-limiting embodiments, said bacteria is one or more of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica*, and *Eubacterium brachy*, but alternate or additional bacteria may be comprised in the compositions described herein, for example, bacteria which may be naturally occurring, bacteria that are in a cluster comprising any one or more of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica*, or *Eubacterium brachy*, or bacteria engineered to express *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica*, and/or *Eubacterium brachy* proteins.

5.3 Recombinant Cells

The present invention provides for therapeutic compositions, and therapeutic uses thereof, as described herein, which reduce the risk of cancer relapse, and/or increase the likelihood of survival from a cancer relapse in a subject. Such therapeutic compositions can comprise, for example, therapeutic bacteria, small molecules, polypeptides, or nucleic acid molecules.

In certain non-limiting embodiments, the therapeutic compositions reduce the amount of *Enterococcus faecium* toxin, and/or inhibit proliferation and/or growth of *Enterococcus faecium* in a subject.

In some non-limiting embodiment, the therapeutic composition comprises a recombinant *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica*, or *Eubacterium brachy* bacteria, a combination thereof, or a cluster comprising any one or more of the foregoing bacteria, or progeny thereof.

In certain non-limiting embodiments, the therapeutic composition comprises a recombinant cell, or progeny thereof, for example, a recombinant cell expressing one or more proteins endogenously expressed by a *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica*, or *Eubacterium brachy* bacteria, a combination thereof, or a cluster comprising any one or more of the foregoing bacteria.

In certain non-limiting embodiments, expression of an antibiotic resistance gene by the recombinant cell, or progeny thereof, reduces the inhibition in growth or survival of the recombinant cell caused by exposure to said antibiotic such as, but not limited to, an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic. In other non-limiting embodiments, the recombinant cell is resistant to an antibiotic other than the foregoing antibiotics.

In certain non-limiting embodiments, expression of an antibiotic susceptibility gene by the recombinant cell increases the inhibition in growth or survival of the recombinant cell caused by exposure to said antibiotic. In certain non-limiting embodiments, such antibiotics can include, but are not limited to, an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic. In other non-limiting embodiments, the recombinant cell is susceptible to an antibiotic other than the foregoing antibiotics.

In certain non-limiting embodiments, the recombinant cells described herein express one or more recombinant genes that increase the synthesis and secretion of a metabolite that modulates a subject's risk of relapse, for example, a *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica*, or *Eubacterium brachy* protein that reduces the subject's risk for cancer relapse.

Delivery of nucleic acid into a subject or cell, e.g., bacterial cells of the intestinal microbiota, can be either direct, in which case the subject or cell, e.g., bacterial cells of a subject's intestinal microbiota, is directly exposed to the nucleic acid or nucleic acid-carrying vectors, or indirect, in which case, cells, e.g., a host cell, such as isolated bacterial cells of the intestinal microbiota, are first transformed with the nucleic acids in vitro, then transplanted into the subject. These two approaches are known, respectively, as in situ or ex vivo gene therapy.

For general reviews of the methods of gene therapy, see Kron and Kreppel, Curr Gene Ther 12(5):362-73 (2012); Yi et al. Curr Gene Ther 11(3):218-28 (2011); Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); Morgan and Anderson, Ann. Rev. Biochem. 62:191-217 (1993); and May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In certain non-limiting embodiments, the nucleic acid can be introduced into cells, e.g., bacterial host cells, prior to administration in vivo of the resulting recombinant cell by any method known in the art, including but not limited to transfection, electroporation, microinjection, lipofection, calcium phosphate mediated transfection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985)), and can be used in accordance with the present disclosure, provided that the necessary developmental and physiological functions of the recipient cells are not disrupted. Usually, the method of transfer includes the transfer of a selectable marker to the host cells. The cells are then placed under selection to isolate those host cells that have taken up and are expressing the transferred gene. Those host cells are then delivered to a patient.

The resulting recombinant cells, or progeny thereof, can be delivered to a patient by various methods known in the art. The amount of cells envisioned for use depends on the desired effect, patient state, etc., and can be determined by one skilled in the art.

In certain non-limiting embodiments, the terms "vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc. A "therapeutic vector" as used herein refers to a vector which is acceptable for administration to an animal, and particularly to a human.

Vectors typically include the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can accept additional (foreign) DNA and which can be introduced into a suitable host cell. A plasmid vector can contain coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA can be from the same gene or from different genes, and can be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET plasmids (Invitrogen, San Diego, Calif.), pCDNA3 plasmids (Invitrogen), pREP plasmids (Invitrogen), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

Suitable vectors include, for example, bacteriophages, cosmids, plasmids, naked DNA, DNA lipid complexes, and other recombination vehicles typically used in the art which have been described for expression in a variety of eukaryotic and prokaryotic hosts, and can be used for gene therapy as well as for simple protein expression.

5.4 Pharmaceutical Compositions

In certain non-limiting embodiments, the present disclosure provides for pharmaceutical compositions, and therapeutic uses thereof as described herein, which include a therapeutic composition, as described herein, such as, for example, a therapeutic bacteria, as described herein. Such pharmaceutical compositions can further include at least one other agent, such as a stabilizing compound or additional therapeutic agent, for example, a probiotic, prebiotic, postbiotic, and/or antibiotic, and can be administered in any sterile, biocompatible pharmaceutical carrier, including, but not limited to, saline, buffered saline, dextrose, glycerol, polyethylene glycol, and water. The composition can be in a liquid or lyophilized or freeze-dried form. In some non-limiting embodiments, a formulation includes a diluent (for example, a buffer such as Tris, citrate, acetate or phosphate buffers) having suitable pH values and ionic strengths, solubilizer such as polysorbate (e.g., Tween®), carriers such as human serum albumin or gelatin. In some cases, a preservative may be included that does not affect viability of the organisms in the composition. Examples of preservatives include thimerosal, parabens, benzylalconium chloride or benzyl alcohol, antioxidants such as ascorbic acid or sodium metabisulfite, and other components such as lysine or glycine. Selection of a particular composition will depend upon a number of factors, including the condition being treated, the route of administration and the pharmacokinetic parameters desired. A more extensive survey of components suitable for pharmaceutical compositions is found in Remington's Pharmaceutical Sciences, 18th ed. A. R. Gennaro, ed. Mack, Easton, Pa. (1980).

In certain non-limiting embodiments, the methods and compositions of the present disclosure find use in reducing the risk of cancer relapse in a subject, and/or increasing the chance of survival in a subject having a cancer relapse. Such therapeutic bacteria are administered to the patient in a pharmaceutically acceptable carrier. The route of administration eventually chosen will depend upon a number of factors and can be ascertained by one skilled in the art.

In certain non-limiting embodiments, the pharmaceutical compositions of the present disclosure can be formulated using pharmaceutically acceptable carriers well known in the art in dosages suitable for oral, nasogastric, or rectal administration. Such carriers enable the pharmaceutical compositions to be formulated as tablets, pills, capsules, liquids, gels, syrups, slurries, suspensions and the like, for oral, rectal or nasal ingestion by a patient to be treated. In some non-limiting embodiments, the formulation comprises a capsule or tablet formulated for gastrointestinal delivery, e.g., an enteric coated capsule or pill.

Pharmaceutical compositions suitable for use in the present disclosure include, in certain non-limiting embodiments, compositions where the active ingredients are contained in an effective amount to achieve the intended purpose. The amount will vary from one individual to another and will depend upon a number of factors, including the overall physical condition of the patient, e.g., severity and degree of cancer relapse, cancer cell growth and/or tumor growth.

In certain non-limiting embodiments, the compositions of the present disclosure can be administered for prophylactic and/or therapeutic treatments. For example, in alternative non-limiting embodiments, pharmaceutical compositions of the present disclosure are administered in an amount sufficient to treat, prevent and/or ameliorate cancer relapse, for example, cancer cell growth and/or cancer cell presence and/or tumor growth and/or tumor presence and/or tumor volume. As is well known in the medical arts, dosages for any one patient depends upon many factors, including stage of the disease or condition, the severity of the disease or condition, the patient's size, body surface area, age, the particular compound to be administered, sex, time and route of administration, general health, and interaction with other drugs being concurrently administered.

Accordingly, in certain non-limiting embodiments, a therapeutic bacteria can be administered to a patient alone, or in combination with one or more other drugs, nucleotide sequences, lifestyle changes, etc. used in the treatment or prevention of cancer relapse, or symptoms thereof, or in pharmaceutical compositions where it is mixed with excipient(s) or other pharmaceutically acceptable carriers.

Single or multiple administrations of formulations can be given depending on the dosage and frequency as required and tolerated by the patient. In certain non-limiting embodiments, the formulations should provide a sufficient quantity of active agent to effectively treat, prevent or ameliorate the cancer relapse, or symptoms or complications thereof as described herein.

5.5 Methods of Treatment

In certain non-limiting embodiments, the present invention provides for a method of reducing the risk of cancer relapse, and/or decreasing the amount of *Enterococcus faecium* toxin, and/or inhibit proliferation and/or growth of

*Enterococcus faecium* in a subject, comprising administering, to a subject in need of such treatment, an effective amount of a composition described herein, for example, a recombinant cell and/or a composition comprising one or more therapeutic bacteria, for example, *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria.

Subjects in need of such treatment or compositions include subjects who have had a cancer relapse, and/or cancer patients who have been determined to be at greater risk of cancer relapse, as described herein.

Subjects at greater risk of cancer relapse include individuals who have received a hematopoietic stem cell transplantation (HSCT) (for example, an allogeneic or autologous HSCT), a bone marrow transplant, and/or a cord blood or cord stem cell transplant. In certain non-limiting embodiments the transplant is T-cell replete. In certain non-limiting embodiments the transplant is T-cell depleted.

In certain non-limiting embodiments, the present invention provides for a method for reducing the risk of cancer relapse and/or improving the likelihood of survival from a cancer relapse, comprising administering, to a subject in need of such treatment, an effective amount of a composition or a therapeutic bacteria described herein, for example, *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria.

In certain non-limiting embodiments, an effective amount of a composition or a therapeutic bacteria described herein is an amount which reduces the amount of *Enterococcus faecium* toxin, and/or inhibits proliferation and/or growth of *Enterococcus faecium* in a subject.

Increasing the likelihood of survival from a cancer relapse refers to a decrease in cancer cell growth, and/or cancer cell proliferation, and/or tumor growth, and/or tumor volume, and/or tumor presence, and/or detectable amount of minimal residual disease. A reduction in the severity of cancer relapse, or an increase in the likelihood of survival from a cancer relapse, can result in an amelioration in symptoms or signs of cancer, for example, but not limited to, weight loss, fever, fatigue, and/or pain.

In certain non-limiting embodiments, the present invention provides for a method of reducing the risk of cancer relapse, and/or increasing the chance of survival from a cancer relapse, and/or decreasing the amount of *Enterococcus faecium* toxin, and/or inhibit proliferation and/or growth of *Enterococcus faecium* in a subject, comprising administering, to a subject in need of such treatment, an effective amount of a probiotic. In certain non-limiting embodiments, the probiotic comprises a *Streptococcus anginosus, Parvimonas micra, Acidaminococcus intestini, Eubacterium limosum, Clostridium glycyrrhizinilyticum, Desulfosporosinus lacus, Eubacterium biforme Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica*, or *Eubacterium brachy* bacteria, a combination thereof, or a cluster comprising any one or more of the foregoing bacteria. In certain non-limiting embodiments, the probiotic comprises endogenous flora (for example, an autologous fecal microbiota transplant) that are re-introduced into the subject.

In certain non-limiting embodiments, the present invention provides for a method of reducing the risk of cancer relapse, and/or increasing the chance of survival from a cancer relapse, and/or decreasing the amount of *Enterococcus faecium* toxin, and/or inhibit proliferation and/or growth of *Enterococcus faecium* in a subject, comprising administering, to a subject in need of such treatment, an effective amount of a prebiotic. In certain non-limiting embodiments, the prebiotic promotes the growth, proliferation and/or survival of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, in the subject.

In certain non-limiting embodiments the therapy comprises administering a prebiotic to the subject, wherein the prebiotic comprises one or more agents, for example, a nutritional supplement, that increases growth and survival of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria. In certain non-limiting embodiments, the prebiotic comprises one or more of poorly-absorbed complex carbohydrates, oligosaccharides, inulin-type fructans or arabinoxylans.

In certain non-limiting embodiments, the present invention provides for a method of reducing the risk of cancer relapse, and/or increasing the chance of survival from a cancer relapse, and/or decreasing the amount of *Enterococcus faecium* toxin, and/or inhibit proliferation and/or growth of *Enterococcus faecium* in a subject, comprising administering, to a subject in need of such treatment, an effective amount of a postbiotic. In certain non-limiting embodiments, the postbiotic comprises one or more agents, such as a protein, expressed by *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria. In certain non-limiting embodiments, the postbiotic comprises bacterial metabolites, for example, metabolites that promote anti-inflammatory effects. In certain non-limiting embodiments, the postbiotic comprises media from a culture of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria. In certain non-limiting embodiments, the postbiotic comprises a short-chain fatty acid such as butyrate or similar acids, or secondary bile acids.

In certain non-limiting embodiments, the present invention provides for a method of reducing the risk of cancer relapse, and/or increasing the chance of survival from a cancer relapse, and/or decreasing the amount of *Enterococcus faecium* toxin, and/or inhibit proliferation and/or growth of *Enterococcus faecium* in a subject, comprising administering, to a subject in need of such treatment, an effective amount of an antibiotic. In certain embodiments, the antibiotic is selective for *Enterococcus faecium*. In certain non-limiting embodiments, the antibiotic does not target *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria. For example, in certain non-limiting embodiments, the methods of the present invention comprise administering an antibiotic to the subject along with recombinant *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, wherein the recombinant cells express antibiotic resistance gene such that the cells are resistant to the antibiotic administered with the recombinant cells. In certain non-limiting embodiments, the antibiotic comprises a penicillin, vancomycin, and/or linezolid antibiotic.

In certain non-limiting embodiments, the present invention provides for a method of reducing the risk of cancer relapse, and/or increasing the chance of survival from a cancer relapse, and/or decreasing the amount of *Enterococcus faecium* toxin, and/or inhibit proliferation and/or growth of *Enterococcus faecium* in a subject, comprising administering, to a subject in need of such treatment, an effective amount of a cancer therapy, for example surgery to remove cancerous cells or tissue, radiation therapy, chemotherapy, immunotherapy (for example, but not limited to, antibodies directed to CTLA-4, PD-1, CD52, and/or CD20; and cytokines such as interferons and interleukins), stem cell therapy and/or cellular therapies (for example, but not limited to, CAR-modified T cells and other antigen-specific T cells).

In certain non-limiting embodiments, such methods comprise determining the abundance of one more bacteria present in an intestinal microbiota sample of a subject diagnosed with cancer, for example, *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica*, or *Eubacterium brachy*, bacteria, a combination thereof, or a cluster comprising any one or more of the foregoing bacteria, wherein the subject is diagnosed or identified as being at greater risk of a cancer relapse, when the abundance or amount of the one or more bacteria in the subject's microbiota is lower than a bacteria reference level. In some non-limiting embodiments, a bacteria reference level is an abundance of bacteria, for example, *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria, present in intestinal microbiota, a level below which is indicative of being at greater risk of cancer relapse, as determined by a medical doctor or person of skill in the art.

In certain non-limiting embodiments, such methods comprise determining the abundance of *Enterococcus faecium* bacteria present in an intestinal microbiota sample of a subject diagnosed with cancer, wherein the subject is diagnosed or identified as being at greater risk of a cancer relapse, when the abundance or amount of the bacteria in the subject's microbiota is greater than a bacteria reference level. In some non-limiting embodiments, a bacteria reference level is an abundance of a bacteria, for example, *Enterococcus faecium*, present in intestinal microbiota, a level above which is indicative of being at greater risk of cancer relapse, as determined by a medical doctor or person of skill in the art.

In certain non-limiting embodiments, a subject determined to be at a greater risk for cancer relapse can be monitored more frequently and/or for an extended period of time for relapse following treatment, and can be administered therapeutic regimens in addition to, or as an alternative to, a hematopoietic stem cell transplantation, for example, but not limited to, surgery to remove cancerous cells or tissue, radiation therapy, chemotherapy, immunotherapy (for example, but not limited to, antibodies directed to CTLA-4, PD-1, CD52, and/or CD20; and cytokines such as interferons and interleukins), stem cell therapy and/or cellular therapies (for example, but not limited to, CAR-modified T cells and other antigen-specific T cells).

5.6 Kits

The presently disclosed subject matter provides for kits for diagnosing a subject as being at greater or reduced risk of cancer relapse, wherein the kit comprises one or more agent for detecting the presence of *Streptococcus anginosus, Parvimonas micra, Acidaminococcus intestini, Eubacterium limosum, Clostridium glycyrrhizinilyticum, Desulfosporosinus lacus, Eubacterium biforme, Enterococcus faecium, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria. In certain non-limiting embodiments, the agent comprises nucleic acid primers specific for said bacteria. In certain non-limiting embodiments, the nucleic acid primers are specific for 16S rRNA sequencing.

The presently disclosed subject matter provides for kits for treating a subject at greater risk of cancer relapse, or a subject who has cancer relapse. In certain non-limiting embodiments, the kit comprises one or more therapeutic composition or cells described herein, for example, therapeutic bacteria selected from the group consisting of *Streptococcus anginosus, Parvimonas micra, Acidaminococcus intestini, Eubacterium limosum, Clostridium glycyrrhizinilyticum, Desulfosporosinus lacus, Eubacterium biforme, Anaerofustis stercorihominis, Pseudoramibacter alactolyticus, Peptococcus niger, Armatimonas rosea, Saccharofermentans acetigenes, Finegoldia magna, Levyella massiliensis, Gallicola barnesae, Murdochiella asaccharolytica, Eubacterium brachy*, a combination thereof, or a cluster comprising any one or more of the foregoing bacteria.

In certain non-limiting embodiments, the kit comprises instructions for administering the therapeutic composition or cells. The instructions can comprise information about the use of the composition or cells for reducing the risk of cancer relapse, or for increasing the likelihood of surviving a cancer relapse. In certain non-limiting embodiments, the instructions comprise at least one of the following: description of the therapeutic composition or cells; dosage schedule and administration; precautions; warnings; indications; counter-indications; over dosage information; adverse reactions; animal pharmacology; clinical studies; and/or references. The instructions can be printed directly on a container (when present) comprising the cells, or as a label applied to the container, or as a separate sheet, pamphlet, card, or folder supplied in or with the container.

6. EXAMPLES

The presently disclosed subject matter will be better understood by reference to the following Examples, which are provided as exemplary of the invention, and not by way of limitation. Examples 1-3 describe the identification of intestinal flora that are associated with a reduced risk of cancer relapse in overlapping populations of cancer patients.

Example 1

Certain Intestinal Flora are Associated with Risk of Cancer Relapse in Cancer Patients Methods In the present example, a biomarker-discovery approach was applied and a retrospective observational analysis of 160 adults who received an unmodified (T-cell-replete) allograft was performed. Patients were prospectively enrolled in a fecal biospecimen-collection protocol. For this analysis, we selected patients who had provided at least one specimen during the first 3 weeks following allo-HSCT. The primary diseases in this cohort were AML (37%), Non-Hodgkin's Lymphoma (33%), ALL (8%), MDS (7%), CLL (6%), Hodgkin's Lymphoma (6%), CML (2%), and myeloproliferative neoplasm (2%). The mean age of the patients was 52 years (range 21-75). They were conditioned with ablative (17%), reduced-intensity (64%), and nonmyeloablative (19%) regimens. They received grafts from cord blood (46%), unrelated adults (33%), or related adults (22%). Among adult grafts, 92% were from peripheral blood and 8% were from bone marrow. This group of patients is the "patient flora cohort."

A second group of 309 adult patients was also analyzed. Table 1 describes the primary diseases of this cohort, as well as allograft type received, and conditioning regimen.

TABLE 1

| Cancer and treatment status of the 309 adult patient population | | |
|---|---|---|
| AML | 112 | 36% |
| MDS | 49 | 16% |
| NHL | 39 | 13% |
| myeloma | 36 | 12% |
| ALL | 25 | 8% |
| T-NHL | 14 | 5% |
| CLL/SLL | 10 | 3% |
| MPN | 9 | 3% |
| Hodgkin's | 9 | 3% |
| CML | 6 | 2% |
| Ablative | 174 | 56% |
| Reduced Intensity | 105 | 34% |
| Nonablative Graft | 30 | 10% |
| TCD | 149 | 48% |
| Unmodified PBSC/BM | 87 | 28% |
| Cord | 73 | 24% |
| Age mean (range) | 53.4 | (21-75) |

A census of the bacterial species in each stool sample was generated by qPCR of 16S rRNA deep-sequencing as previously described (Jenq et al., *Biol Bone Marrow Transplant* 21:1373-1383 2015). Briefly, for each stool specimen, DNA was purified using a phenol-chloroform extraction technique with mechanical disruption (bead-beating) based on a previously described protocol. Samples from the patient flora cohort were analyzed using the 454 GS FLX Titanium platform (454 Life Sciences, Branford, Conn.) to sequence the V1-V3 region of the bacterial 16S rRNA gene.

Sequence data were compiled and processed using mothur version 1.34, screened and filtered for quality, and then classified to the species level using a modified form of the Greengenes reference database. Microbial diversity was quantified using the inverse Simpson index and the Shannon diversity index of operational taxonomic units with 97% similarity. Taxonomic abundance comparisons were performed to identify biomarkers of cancer relapse following allogeneic hematopoietic stem cell transplantation using linear discriminant analysis effect size analysis, using a logarithmic linear discriminant analysis cutoff of 2.0 as described in the original article by the developers.

The area under the curve of bacterial abundance over time was used as a measure of each patient's cumulative exposure to each bacterial taxon. Bacterial taxa of each patient present at a frequency>1% were evaluated for association with the outcome of relapse or progression of disease within the first year after allo-HSCT using linear discriminant analysis of effect size (LEfSe; e.g. Segata et al., *Genome Biology*, 2011).

Results

Figure 2:
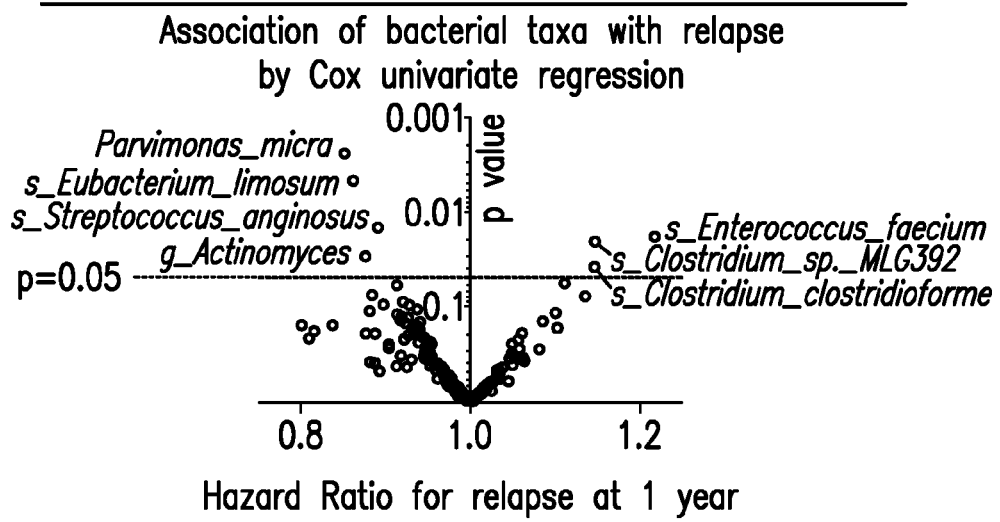
Figure 5:
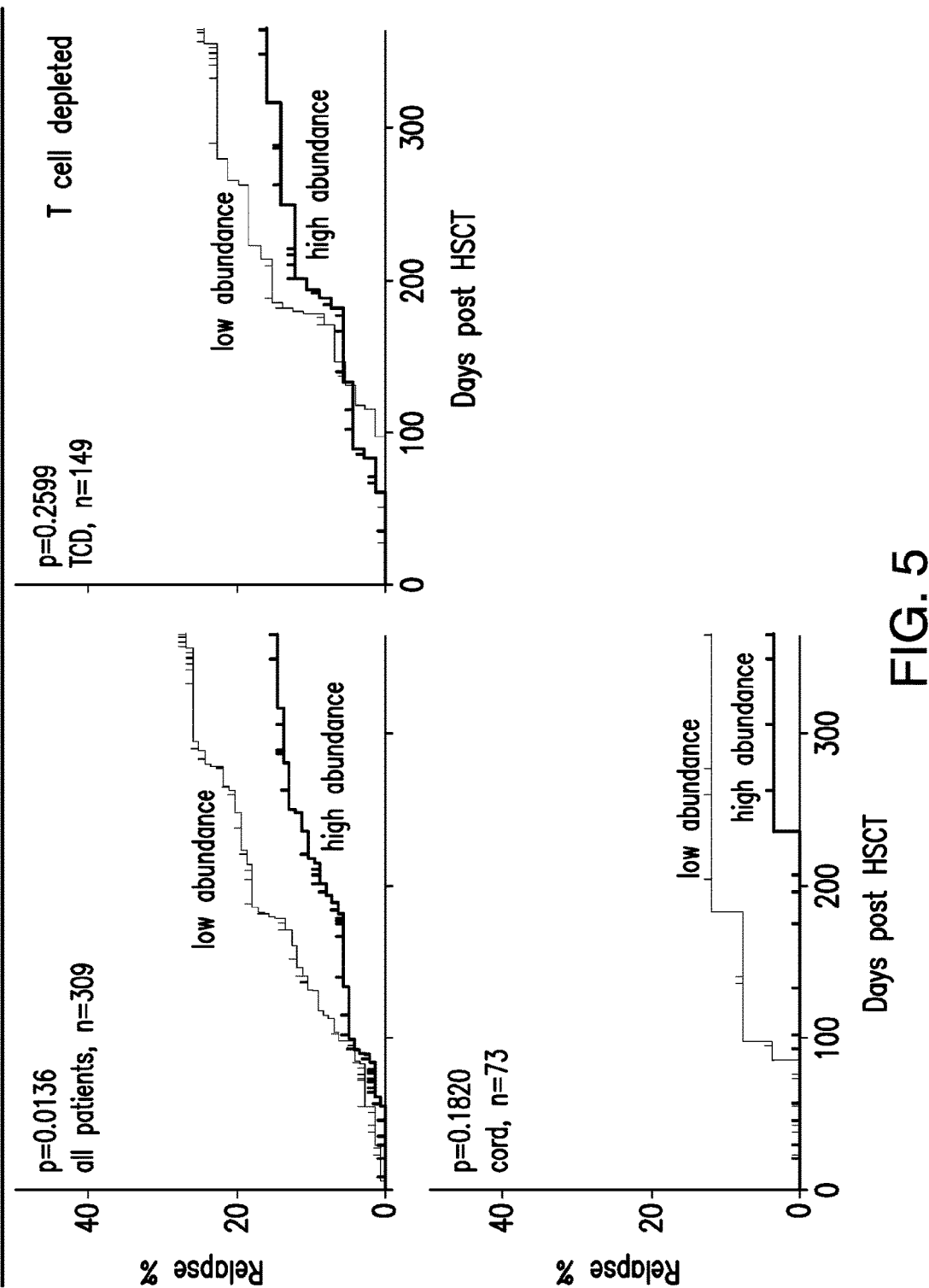
FIG. 5 shows the association between abundance of *Parvimonas micra* and relapse, indicating that the best discriminating ability of *Parvimonas* is after conventional (T cell replete), non-cord grafts.
Figure 6:
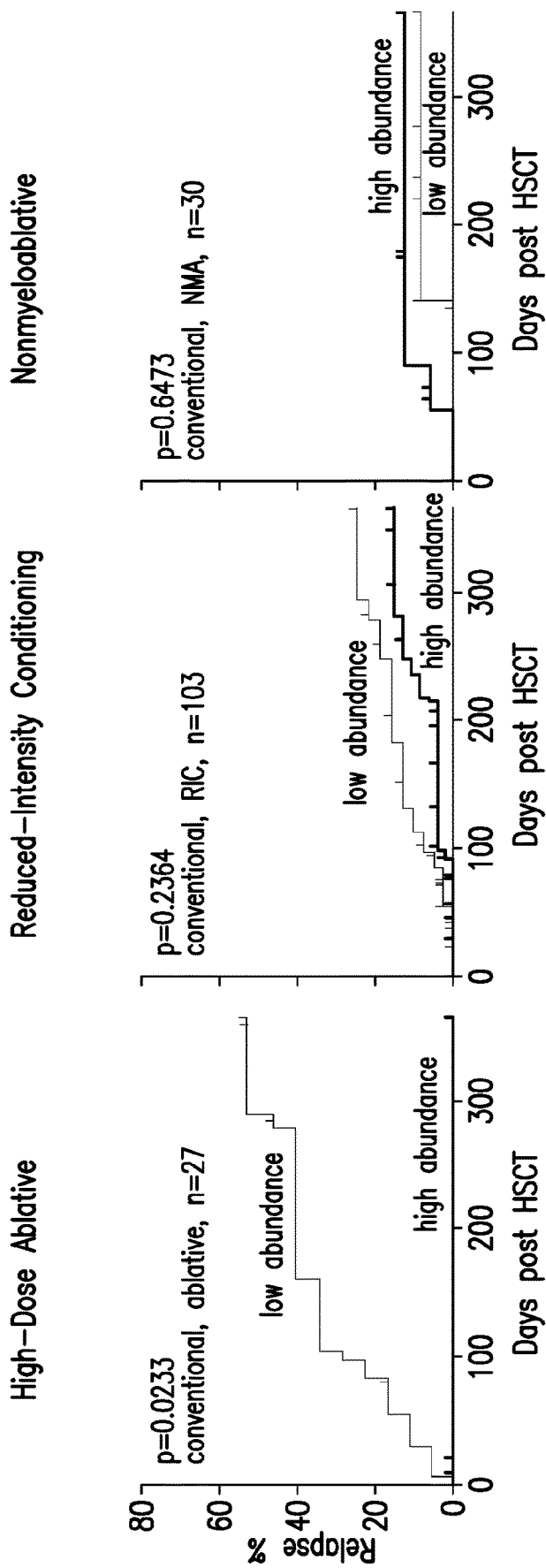
FIG. 6 shows the association between abundance of *Parvimonas micra* and relapse, indicating that the best discriminating ability of *Parvimonas* is after high-intensity conditioning regimens.
Figure 7:
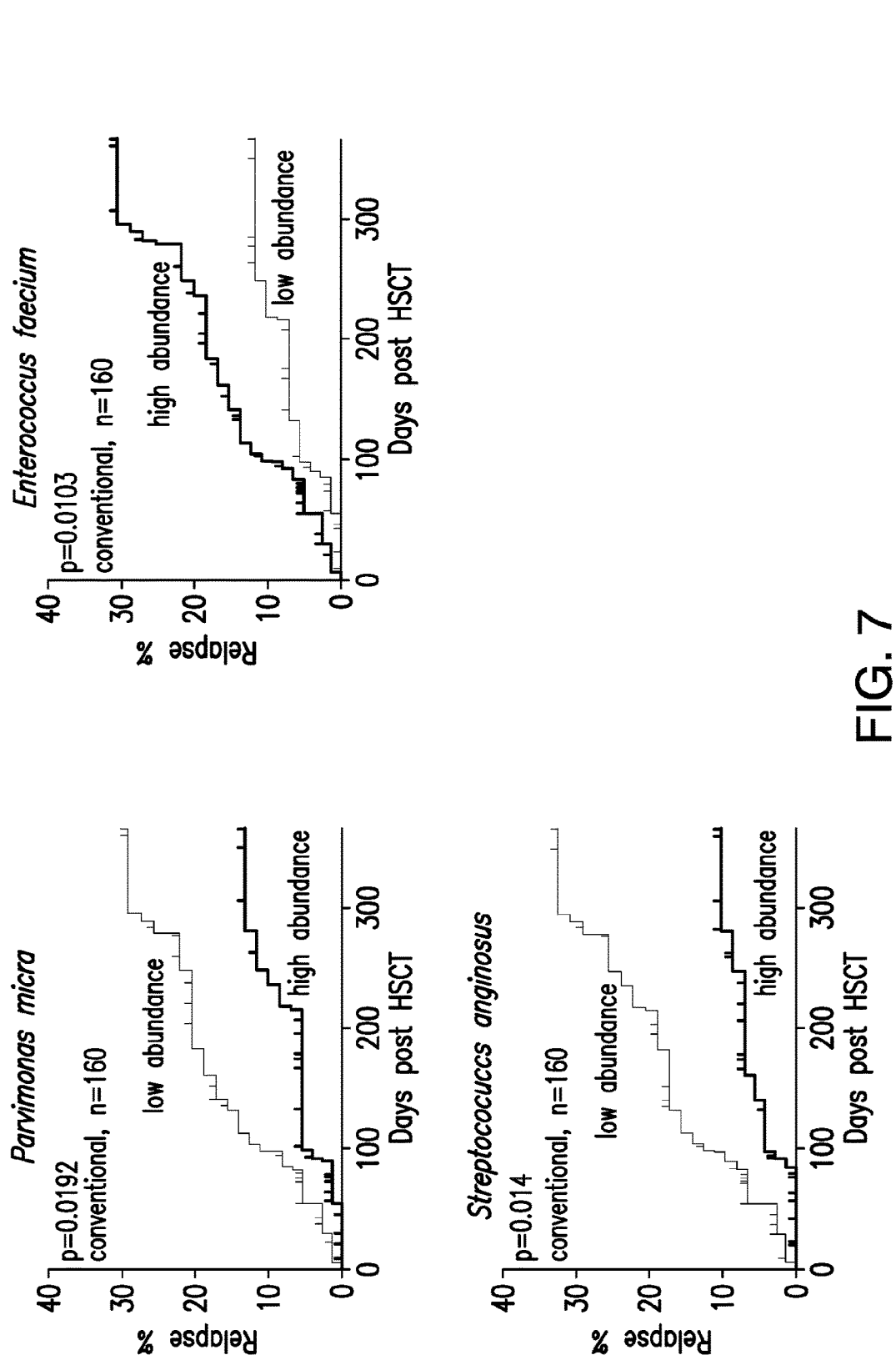
FIG. 7 shows the association between abundance of *Parvimonas micra, Strepticoccus anginosus,* and *Enterococcus faecium* and relapse.
Figures 8, 9:
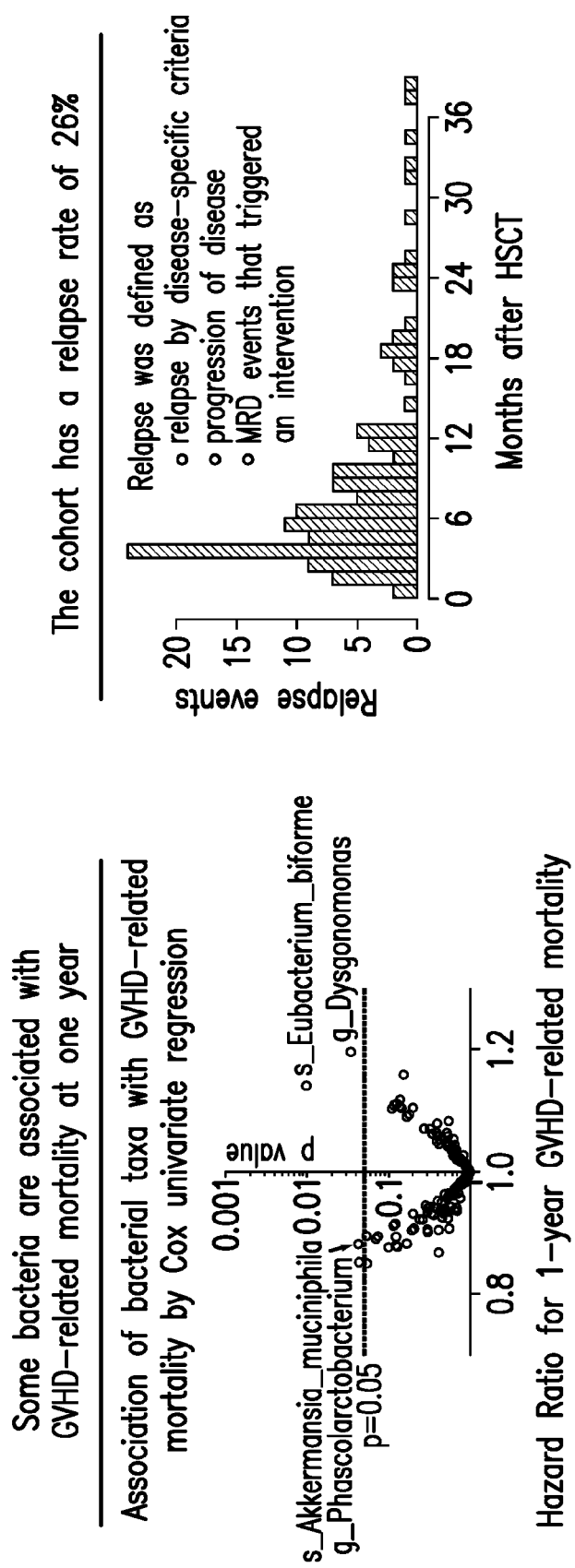
FIG. 8 shows associations between bacterial taxa and GVHD-related mortality at one year. Association of bacterial taxa with GVHD-related mortality was determined by Cox univariate regression.
FIG. 9 shows the relapse rate of the cohort of 466 subjects described by Example 2 over 36 months after allo-HSCT.

Associations of bacteria with relapse risk were quantified by Cox univariate regression. Among the taxons most significantly associated with relapse risk were members of the human oral flora including *Streptococcus anginosus, Parvimonas micra, Eubacterium limosum*, and *Actinomyces* (FIG. 2). After stratifying the patients by median abundance, we found that those with higher abundance of this bacterium had less relapse after transplantation (p=0.0014). Patients with higher abundance of the bacterium *Parvimonas micra* also had less relapse after transplantation (FIGS. 2, 4A, 4B and 7). *Parvimonas micra* is a gram-positive anaerobic coccus, "*peptostreptococci*", a commonly found oral species in dental plaque and can stimulate macrophage production of TNF-α, IL-6 and IL8 and stimulates NOD2 receptors that are upstream of NF-kB (Marchesan, *Molecular Oral Microbiology* 2015 Volume 31, Issue 3, June 2016, Pages 243-258). *Parvimonas micra* also makes an Fc-binding protein. *Parvimonas micra* had the best correlation with lack of relapse in patients who received T-cell replete, non-cord grafts (FIGS. 5 and 7), and after myeloablative conditioning (FIG. 6). In addition, patients with higher abundance of the bacterium *Acidaminociccus intestini* and *Strepticoccus anginosus*, respectively (FIG. 7) also had lower rates of relapse. We also identified bacteria associated with increased risk of relapse, such as *Enterococcus faecium* (p=0.0103) (FIGS. 2 and 7). Additionally, certain bacteria were associated with a reduced risk of GVHD-related mortality, for example, *Akkermansia muciniphila* and *Phascolarctobacterium*, or increased risk of GVHD-related mortality, for example, *Eubacterium biforme* and *Dysgonomonas*, as determined by Cox univariate regression (FIG. 8).

Figure 3:
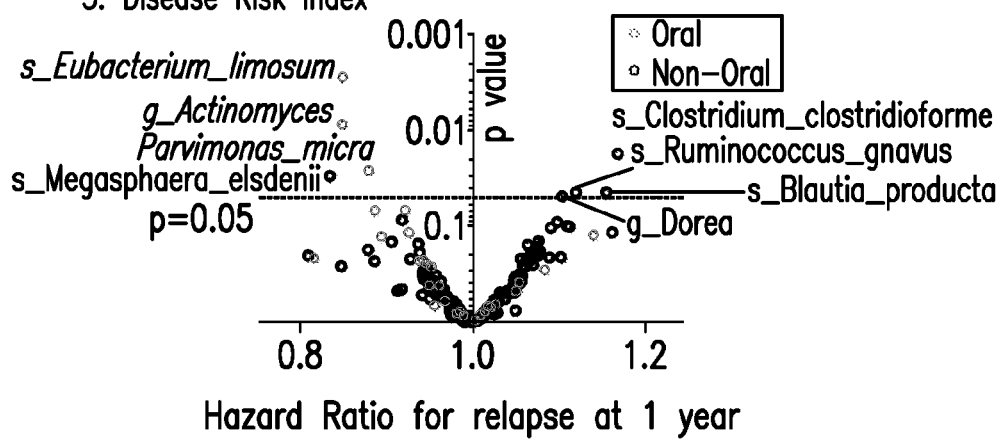
Figure 4:
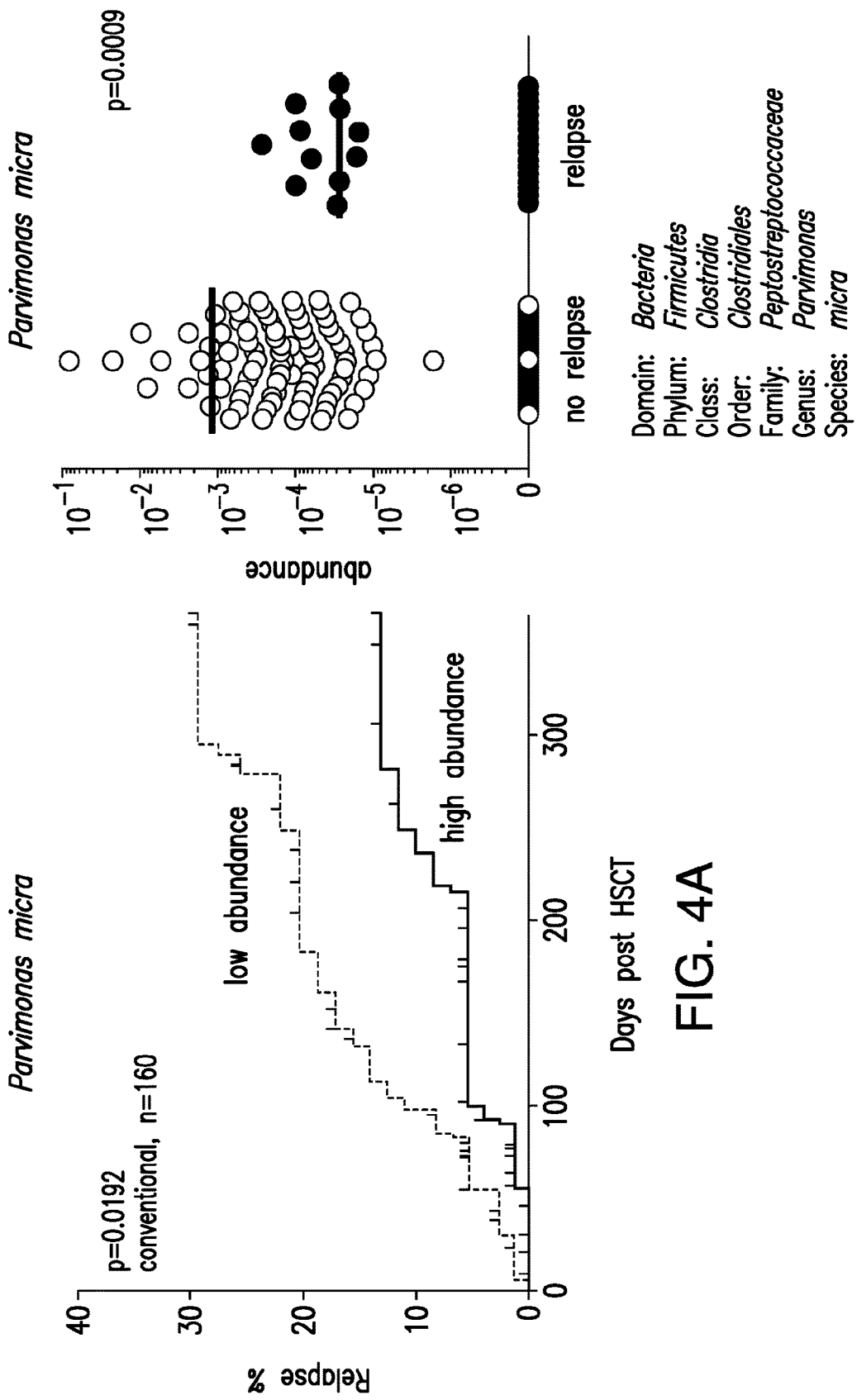

These bacteria were evaluated as biomarkers in multivariate Cox models adjusted for three factors that were associated with relapse in this cohort: Refined Disease Risk Index (RDRI or DRI, Armand et al., Blood. 2014 Jun. 5; 123(23): 3664-71), conditioning intensity, and graft source (cord blood vs. adult donor), and FIG. 3 shows that bacterial abundance predicts relapse after these adjustments are made.

*Streptococcus anginosus* predicted relapse in a multivariate model adjusted for all three factors (HR 0.39, 95% CI 0.16-0.96, p=0.041). *Enterococcus faecium* predicted relapse in a model adjusted for RDRI and conditioning intensity but failed to do so in a model additionally adjusted for graft source.

Figure 1:
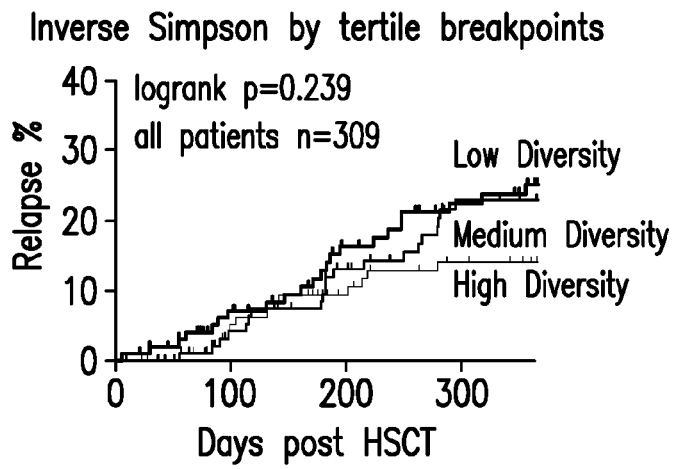

Applicants previously reported that low bacterial diversity is associated with decreased overall survival after allo-HSCT (Taur et al., Blood. 2014 Aug. 14; 124(7):1174-82). Bacterial diversity was quantified using the reciprocal Simpson diversity index (p>0.1) after composition analysis of stool samples from 309 patients performed by 16S gene sequencing, as described above. Surprisingly, in the present studies, Applicants did not find an association between bacterial diversity and cancer relapse. (FIG. 1).

Thus, the results of this retrospective analysis have identified an association between relapse after allo-HSCT and the abundance of certain bacterial species or OTUs in the intestinal flora. Accordingly, these data demonstrate that detection of such species or OTUs can be used to evaluate whether a patient who has been treated for cancer, e.g., with HSCT, is at increased risk of cancer relapse.

Example 2

*Acidaminococcus Intestini* Abundance in the Intestinal Flora of a Cancer Patient is Associated with a Reduced Risk of Cancer Relapse Methods 2,391 weekly fecal samples of 613 adult cancer patients who received allogeneic hematopoietic stem cell transplantation (allo-HSCT) were collected over three weeks and analyzed as described by Example 1 to determine the levels of bacteria present in the samples. In this example, the V4-V5 region of the bacterial 16S rRNA gene was sequenced. Samples were collected from day 0-21 after allo-HSCT. 147 patients were excluded from the study such that a final cohort of 466 patients were analyzed. The characteristics of the 466 patient cohort are provided in Table 2. The cohort exhibited a cancer relapse rate of 26% within 36 months after allo-HSCT (FIG. 9).

TABLE 2

| Cancer and treatment status of the 466 adult patient population | | |
|---|---|---|
| Disease | | |
| AML | 175 | 38% |
| MDS | 75 | 16% |
| NHL | 53 | 11% |
| myeloma | 50 | 11% |
| ALL | 40 | 9% |
| T-NHL | 20 | 4% |
| CLL/SLL | 14 | 3% |
| Hodgkin's | 13 | 3% |
| CML | 11 | 2% |
| MPN | 10 | 2% |
| Other | 5 | 1% |
| Follow-up Duration | | |
| median | 436 days (14.5 months) | |
| range: | 9-2, 132 days | |
| Conditioning | | |
| Ablative | 266 | 57% |
| Reduced Intensity | 156 | 34% |
| Nonablative | 44 | 9% |
| Graft | | |
| T-cell Depleted | 229 | 49% |
| Unmodified PBSC/BM | 148 | 32% |
| Cord | 89 | 19% |
| Age mean (range) | 54 | (22-75) |
| Disease Risk Index | | |
| Low | 55 | 12% |
| Intermediate | 299 | 64% |
| High | 112 | 24% |

Results

Figures 10, 11:
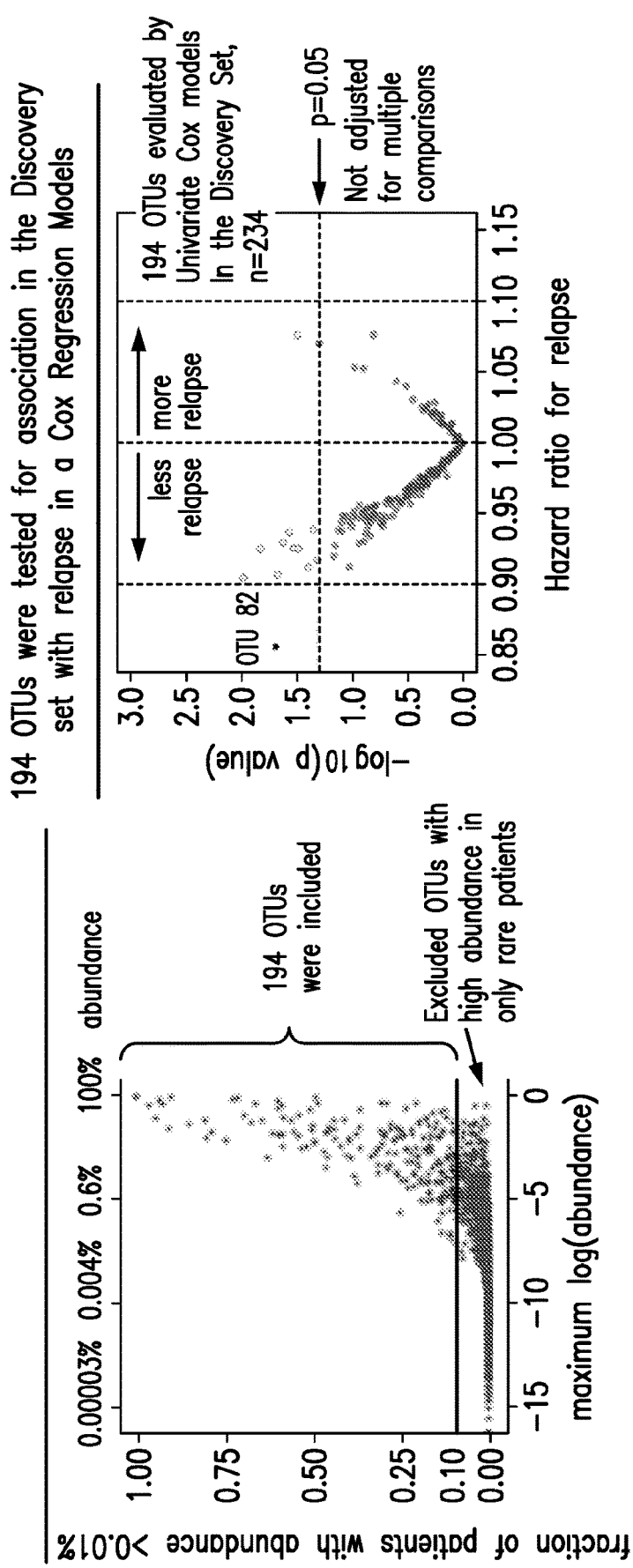
FIG. 10 shows the abundance thresholds of >0.01% in >10% for OTUs that were considered for analysis of their association with relapse or lack of relapse as described in Example 2. The total number of OTUs considered was 194.
FIG. 11 shows the associations between the 194 OTUs considered and levels of relapse using Cox regression modeling in a 234 patient Discovery subset of the 466 patient cohort.

The data from these experiments further support the discovery that although intestinal flora diversity predicts overall survival after allo-HSCT, it does not predict relapse. The area under the curve of bacterial abundance over time was used as a measure of each patient's cumulative exposure to each bacterial taxon. 2,018 Operational Taxonomic Units (OTUs) were identified across all samples. Only OTUs present at >0.01% abundance in >10% of the patients were considered (FIG. 10). Patients were partitioned into Discovery and Validation sets (n=232 and n=234) with equal distribution of relapse events. Abundance-AUCs for 194 OTUs were evaluated for associations with relapse in the Discovery Set using Cox regression models (FIG. 11). A cutoff threshold of $3.4 \times 10^{-5}$ was systematically selected in the Discovery set to minimize p value (Camp, Clin Cancer Res 2004), which was then applied to the Validation set. This cutoff resulted in about 85% having low abundance of the bacteria (which was correlated with relapse) and 15% high abundance (which was correlated with a lack of relapse). *Acidaminococcus intestini* abundance was identified as being associated with less relapse in both the Discovery and Validation sets (FIGS. 12A and 12B).

*Acidaminococcus intestini* was evaluated as a biomarker in multivariate Cox models adjusted for three factors that were associated with relapse in this cohort: Refined Disease Risk Index (RDRI, Armand et al., *Blood* 2014), conditioning intensity, and graft source. *Acidaminococcus* intestini predicted relapse in a multivariate model adjusted for RDRI (FIG. 13). Furthermore, the association of *Acidaminococcus intestini* with less relapse was primarily associated with T-cell replete transplants (FIGS. 14A and 14B). Accordingly, the presence of *Acidaminococcus intestini* can be used in the selection of an appropriate treatment for a patient. For example, patients having a high level of *Acidaminococcus intestini* present in their intestinal flora have a reduced risk of relapse when treated with a T-cell replete transplant. As such, patients with increased levels of *Acidaminococcus intestini* present in their intestinal flora are candidates for treatment with a T-cell replete transplant (as opposed to other forms of transplant, such as a T-cell depleted transplant).

Additionally, various intestinal microbiota were also associated with relapse and GVHD-related mortality (FIGS. 15A and 15B). In particular, *Enterococcus* was associated with GVHD-related mortality and relapse (FIG. 16), *Acidaminococcus* was associated with GVHD-related mortality and a lack of relapse (FIGS. 16 and 17), and *Blautia* was associated with relapse and lack of GVHD-related mortality (FIG. 16).

Example 3

Abundance of a Cluster of Bacteria Including *Eubacterium Limosum* in the Intestinal Flora of Cancer Patients is Associated with a Reduced Progression of Disease and Risk of Cancer Relapse Methods Fecal samples of 541 adult cancer patients who received allogeneic hematopoietic stem cell transplantation (allo-HSCT) were collected and sequenced using 16S ribosomal sequencing. Patients were prospectively enrolled in a fecal biospecimen-collection protocol. Each patient had a sequenced sample collected within the first 21 days following allo-HSCT. The characteristics of the 541 patient cohort are described in Table 3. There were 138 relapse/POD events (incidence 25.5%) during the two-year period of analysis.

Patients who had previously received autologous stem-cell transplantation were included. Patients with non-malignant indications and those with rare diseases not classifiable by the refined disease risk index (Armand et al., Blood 2014; 123:3664-71) were excluded. Excluded patients are detailed in Table 4. Conditioning regimens were categorized by intensity of myeloablation (Bacigalupo et al., Biol Blood Marrow Transplant 2009; 15:1628-33).

TABLE 3

Cancer and treatment status of the 541 adult patient population

| | N = 541 |
|---|---|
| Disease - no. (%) | |
| AML | 195 (36.0) |
| MDS | 85 (15.7) |
| NHL | 68 (12.6) |
| Multiple myeloma | 61 (11.3) |
| ALL | 44 (8.1) |

TABLE 3-continued

Cancer and treatment status of the 541 adult patient population

| | N = 541 |
|---|---|
| T cell malignancies | 24 (4.4) |
| CLL | 16 (3.0) |
| Hodgkin | 15 (2.8) |
| CML | 12 (2.2) |
| MPN | 12 (2.2) |
| CMML | 8 (1.5) |
| MDS/MPN | 1 (0.2) |
| Conditioning Intensity - no. (%) | |
| Myeloablative | 317 (58.6) |
| Reduced intensity | 162 (29.9) |
| Nonmyeloablative | 62 (11.5) |
| Graft Source - no. (%) | |
| Unmodified PBSC/BM | 172 (31.8) |
| Cord | 95 (17.6) |
| T-cell depleted | 274 (50.6) |
| RDRI no. (%) | |
| Low | 63 (11.6) |
| Intermediate | 353 (65.2) |
| High | 125 (23.1) |
| Age - yr. | |
| Mean (SD) | 53.8 (12.1) |
| Range | 19-75 |
| Male sex - no. (%) | 323 (59.7) |
| Mean Follow-up-mo. (SD) | 21.5 (16.6) |

TABLE 4

Participant flow.

| N | |
|---|---|
| 877 | adult patients admitted to the transplant center for a first allo-HCT during study period (Aug. 29, 2009-May 14, 2015) |
| 562 | patients with evaluable samples that were collected during the sampling period (3 weeks post-HCT) were assessed for eligibility |
| Excluded | |
| −4 | non-malignant indications |
| −11 | other rare malignant indications (5 acute biphenotypic leukemia, 6 blastic plasmaytoid dendritic cell neoplasms |
| −1 | patient with two concurrent malignant indications for transplantation (CLL and MDS) |
| −1 | patient in whom the primary outcome of time to relapse/POD not evaluable as the patient was not in remission at time of HCT and died of persistent disease within 30 days of HCT |
| −4 | relapse or death from any cause prior to landmark day 21 |
| 541 | Analysis Cohort |

The first stool sample was collected on Aug. 29, 2009. Consecutive patients with evaluable samples collected up to May 14, 2015 were considered for this study. Clinical data were obtained from an institutional clinical research database. The primary outcome was analyzed between June 2015 and October 2015 by manual review of electronic medical records. For patients who had transferred their care outside of the transplant center within two years of follow-up, outcomes were assessed by telephone interviews with the patients' treating physicians. There were no missing data for the variables reported herein.

During the study period, 877 adults were admitted to the transplant center for a first allo-HCT. Of these, 562 patients (64.1%) had evaluable stool microbiota samples that were collected during sampling period, which was defined as the three weeks following allo-HCT. Post-transplant samples were the focus of this Example because it was believed that the time period during which the grafts were exposed to the microbiota would facilitate the detection of factors associated with GVT. The duration of the sampling period was selected because of a relative uniformity of available samples up to three weeks after transplantation. These 562 patients were assessed for eligibility. As detailed in Table 4, 21 patients were excluded. Accordingly, the analysis cohort consisted of 541 patients.

Stool samples were stored frozen without additives. DNA was extracted from 2,303 stool samples from the 541 patients (mean 4.3 per patient). The genomic 16S ribosomal-RNA V4-V5 variable region was amplified and sequenced on the Illumina MiSeq platform as previously described. (Jenq et al., Biol Blood Marrow Transplant 2015; 21:1373-83; Taur et al., Blood 2014; 124:1174-82). Of the 2,303 stool samples, 1,186 samples were collected during the three-week sampling period immediately following allo-HCT, and an additional 648 samples were collected during the week preceding or the week following the sampling period ("flanking" periods). Sequence data from these 1,834 samples (mean 3.4 per patient) were used to calculate time-weighted average bacterial abundance (FIGS. 18A and 18B). The numbers of samples collected during each time period are detailed in Table 5.

TABLE 5

Number of samples collected in each time period

| | Transplant Day | No. Samples | Patients with ≥1 sample in period No. (%) | Mean samples per patient |
|---|---|---|---|---|
| Sampling period | | | | |
| Three-week sampling period | ≤0 and ≤21 | 1186 | 541 (100%) | 2.2 |
| One-week flanking periods | ≤−7 and <0, or >21 and ≤ 28 | 648 | 420 (77.6%) | 1.5 |
| Sampling + Flanking periods | <−7 and ≤28 | 1834 | 541 (100%) | 3.4 |
| Pre-transplant, single sample | ≤−21 and ≤0 | 469 | 469 (86.7%) | 1.0 |
| Total Samples | ≤−21 and ≤28 | 2303 | 541 (100%) | 4.3 |

Quality-filtered sequences with >97% identity were clustered into OTUs (see Edgar, Nature Methods 2013; 10:996-8) which were classified to the species level against the NCBI 16S ribosomal RNA sequence database (Release version Dec. 4, 2015). (See Tatusova et al., About Prokaryotic Genome Processing and Tools. The NCBI Handbook [Internet]. 2nd ed: National Center for Biotechnology Information (US); 2014). The time-weighted average abundances of OTUs for each patient were calculated using the trapezoidal method (FIG. 18A), using metrics similar to those previously described (Falcão et al., Gynecol Oncol 2005; 97:529-34; Oudard et al., J Clin Oncol 2004; 22:9579). For 420 (77.6%) of the patients, at least one additional sample was available from the week preceding and/or the week following the sampling period (i.e., 647 flanking samples). For these patients, flanking samples were used to interpolate abundance vectors to the bounds of the sampling period (FIG. 18B). In the pre-transplant analysis of single-samples, when more than one sample was available per patient, the sample collected closest to day −10 was selected for analysis. Throughout the study, abundance refers to log-transformed time-weighted averages over the three-week post-transplantation sampling period, except as indicated in the analysis of single pre-transplant samples. Presence or absence of microbiota features was analyzed as a binary variable, with a cutoff of any abundance>0.

A phylogenetic tree was constructed to derive clusters of related OTUs (crOTUs). The phylogenetic tree was constructed using the FastTree algorithm (see Price et al., Mol Biol Evol 2009; 26:1641-50) in the Quantitiative Insights Into Microbial Ecology (QIIME) software package (see Caporaso et al., Nat Methods 2010; 7:335-6) from a sequence alignment of the 3,952 (96.4% of total 4,100) OTUs in the dataset that were successfully aligned. Members of the same phyla were grouped together, indicating that the tree was broadly concordant with standard taxonomy.

The resulting tree contained 3,951 nodes, each of which represents a cluster of related OTUs (i.e., a crOTU). The abundance of each crOTU was calculated as the sum of the abundances of its member OTUs. Potential advantages of this approach over standard taxonomy can include: (1) improved classification of bacteria, as 16S rRNA sequence similarity may be a better measure of evolutionary proximity than phenotypic traits; and (2) finer resolution of bacterial groupings than standard taxonomic levels such as order, family, and genus.

Statistical Analysis

The primary outcome studied was time to relapse or progression of disease (POD) by disease-specific criteria. Detection of minimal residual disease was scored as a relapse/POD event when flow cytometry, radiographic, or molecular results were acted upon clinically by initiation of therapy, infusion of donor lymphocytes, or withdrawal of immunosuppression.

Cause of death after allo-HCT was assigned according to uniform criteria. (See Copelan et al. Biol Blood Marrow Transplant 2007; 13:1469-76). Throughout the study, landmark analysis was applied to consider time to event starting from the end of the microbiota sampling period; patients with an outcome prior to landmark day 21 were excluded from the analysis of that outcome. Statistical analyses were performed using R software. (See R Core Team, R: A Language and Environment for Statistical Computing. Vienna, Australia: R Foundation for Statistical Computing; 2015).

The 541 patient cohort was temporally partitioned into discovery (n=271) and validation (n=270) sets chronologically at the median date of transplantation, Feb. 13, 2013. Temporal validation has been viewed as the most stringent way to partition a single-center dataset for biomarker analysis. (See Altman et al., BMJ 2009; 338:b605). In the discovery set there were 85 relapse/POD events (31.3%), and in the validation set there were 63 relapse/POD events (incidence 23.3%). Microbiota features that met an abundance filtering criteria of >0.01% in >10% of patients were evaluated in the discovery set for association with relapse/POD using cause-specific Cox proportional hazards multivariate regression models. Multivariate models were adjusted for RDRI, conditioning intensity, and graft source. Cause-specific Cox proportional hazards multivariate regression models were used to assess associations between microbiota and outcomes.

The cause specific concordance probability was calculated in the presence of competing risks using the R package "pec". (See Wolbers et al., *Biostatistics* (Oxford, England) 2014; 15:526-39). The cumulative incidents of relapse/POD, transplant-related mortality, and GVHD were determined using the competing-risks method. The competing risk considered for relapse/POD was death without relapse/POD. The competing risk for transplant-related mortality was relapse. The competing risks for GVHD were relapse and death without GVHD. Patients alive after two years of follow-up were censored. Time-to-event curves were drawn using competing-risks cumulative-incidence functions. Statistical significance was assessed using cause-specific proportional hazards except when indicated otherwise. No adjustments for multiple testing were made. Three tests were performed in the validation set (top crOTU, next best crOTU, and top individual OTU).

Results

Empirically defined groups of related bacteria (crOTUs) had stronger associations with clinical outcomes than did operational taxonomic units (OTUs) representing individual species. The presence of a crOTU comprised mostly of *Eubacterium limosum* was associated with less relapse in a multivariate model (HR 0.54, CI 0.38-0.78, p=0.001). This association was most clear among recipients of T-cell-replete allografts.

These data indicate that the presence of a crOTU can be used to evaluate the risk of cancer relapse in a subject receiving HSCT, wherein presence of high levels of crOTU 1614 and/or 1790 in an intestinal microbiota sample from the subject indicates that the subject has a reduced risk of relapse. Furthermore, the information can be used as part of a method for selecting an appropriate HSCT therapy for a subject. For example, the presence of *E. limosum* or a crOTU comprising *E. limosum* (e.g., crOTU 1614) indicates that the patient receiving or expected to receive a HSCT would have a lower risk of cancer relapse if they receive a T-cell-replete allograft.

Microbiota Features

Intestinal microbial diversity, as assessed by the inverse Simpson Index, was not associated with time to relapse/POD (p=0.16) (see FIG. 19), in keeping with prior observations. (See Taur et al., *Blood* 2014; 124:1174-82).

To assess whether particular bacterial subsets could be associated with time to relapse/POD, crOTUs were defined to evaluate for associations with clinical outcomes. To group OTUs by evolutionary distances, a phylogenetic tree was empirically constructed from a sequence alignment of all OTUs identified in the whole cohort, as described above. The analysis was limited to taxa that exceeded an abundance threshold of ≥0.01% in ≥10% of patients.

Association of Microbiota with Time to Relapse/POD in the Discovery Set

Associations between abundance and time to relapse/POD in the discovery set were evaluated for the 208 OTUs and 1,343 crOTUs. FIG. 21 provides the 10 crOTUs having the lowest multivariate p-values. For each crOTU, the most abundant species are listed, as well as rare species that differentiate a crOTU from a neighboring crOTU. The bracketed numerals indicate the number of OTUs in the named species associated with a particular crOTU. The multivariate models were then adjusted for RDRI, conditioning intensity, and graft source. A criterion of p≤0.01 in either univariate (FIGS. 20A and 20C) or multivariate (FIGS. 20B and 20D) Cox models was used to identify strong candidates associated with time to relapse/POD. The candidate most closely associated with relapse/POD risk in the discovery set was crOTU 1614 (multivariate HR 0.84, CI 0.73-0.96, p=0.01), a cluster comprised mostly of *Eubacterium limosum* as well as other related species (FIG. 21).

Accordingly, in some non-limiting embodiments, one or more members of crOTU 1614, e.g., *E. limosum*, are evaluated.

Validation

The top candidate crOTU identified in the discovery set was evaluated for the reproducibility of its association with the outcome in the validation set. The abundance of crOTU 1614 was significantly associated with a reduced risk of relapse/POD in the validation set (HR=0.82, CI 0.71-0.95, p=0.009, FIG. 22C). This association remained significant after multivariate adjustment for conditioning intensity, graft source, and RDRI (HR=0.82, CI=0.70-0.96, p=0.01, FIG. 22C).

The patients in the discovery and validation sets were stratified according to presence or absence of crOTU 1614. Presence was defined as any detectable amount (i.e., any abundance>0). Intestinal presence of crOTU 1614 was associated with reduced risk of relapse/POD in both discovery (HR=0.49, CI=0.30-0.82, p=0.006) and validation sets (HR=0.52, CI=0.31-0.87, p=0.01) (FIG. 23). The two-year cumulative incidence of relapse/progression among patients with and without this group of bacteria was 33.8% and 19.8%, respectively. This association remained significant after adjustment for RDRI, graft source, and conditioning intensity in both the discovery set (HR=0.46, CI=0.27-0.78, p=0.004, FIG. 22B) and in the validation set (HR=0.54, CI=0.31-0.92, p=0, FIG. 22C).

The composition of crOTU 1614 (FIG. 24) includes 30 OTUs (each amplicon comprising about 250 bp), of which 5, 7, and 1 were respectively identified as *Eubacterium limosum, Anaerofustis stercorihominis*, and *Pseudoramibacter alactolyticus*, all of which are members of the family Eubacteriaceae. An additional 15 OTUs were identified as *Peptococcus niger*, a member of the related family Peptococcaceae. In the whole cohort, the majority (67%) of the abundance of crOTU 1614 was attributable to *Eubacterium limosum*, with lesser contributions from *Anaerofustis stercorihominis* and *Peptococcus niger* (15% each) (FIG. 25). Thus, a cluster of species that is predominantly comprised of *Eubacterium limosum* and other related bacteria (i.e., crOTU members) is associated with a decreased risk of relapse/POD.

Discriminatory Ability

The discovery and validation sets were combined for further exploratory analyses. crOTU 1614 was present in 422 (78%) of the 541 patients, with a mean abundance of 0.16% and a maximum abundance of 8%. A progressively lower risk of relapse/POD was observed across the cohort when it was stratified into four abundance bins (p=0.001, FIGS. 26A and 26B) and this association remained significant after multivariate adjustment (p=0.004, FIG. 22B). Abundance was associated with less relapse/POD in a dose-dependent fashion (FIG. 26A).

As shown in Table 6, examination of the clinical features of patients according to presence or absence of crOTU 1614 demonstrated no significant differences in disease type, conditioning intensity, nor graft source.

TABLE 6

Characteristics of patients based on presence of crOTU 1614

|  | Absent<br>N = 119 | Present<br>N = 422 |
|---|---|---|
| Disease - no. (%) | | |
| AML | 47 (39.5) | 148 (35.1) |
| MDS | 23 (19.3) | 62 (14.7) |
| NHL | 12 (10.1) | 56 (13.3) |
| Other | 37 (31.1) | 156 (37.0) |
| Conditioning Intensity - no. (%) | | |
| Myeloablative | 74 (62.2) | 243 (57.6) |
| Reduced intensity | 33 (27.7) | 129 (30.6) |
| Nonmyeloablative | 12 (10.1) | 50 (11.8) |
| Graft Source - no. (%) | | |
| Adult | 40 (33.6) | 132 (31.3) |
| Cord | 19 (16.0) | 76 (18.0) |
| T cell depleted | 60 (50.4) | 214 (50.7) |
| RDRI - no. (%) | | |
| Low | 9 (7.6) | 54 (12.8) |
| Intermediate | 72 (60.5) | 281 (66.6) |
| High | 38 (31.9) | 87 (20.6) |
| Mean Age - yr. (SD) | 51.6 (13.1) | 54.4 (11.8) |

There was a moderate preponderance of higher-risk RDRI scores in patients with absence of intestinal crOTU 1614 (p=0.02), and the association remained significant while adjusting for RDRI in a multivariate model (HR=0.54, CI=0.38-0.78, p<0.001, FIGS. 22A-C). Patients with presence of crOTU 1614 were slightly older (mean 54.4 years compared with 51.7 years, p=0.04). The association between crOTU 1614 and relapse/POD risk was assessed within each of the three RDRI categories. Intestinal presence of crOTU 1614 was associated with less relapse/POD risk among RDRI-high patients (HR=0.45, CI=0.25-0.81, p=0.008) and RDRI-intermediate patients (HR=0.52, CI=0.33-0.83, p=0.006) (FIG. 27). There was no association, however, among RDRI-low patients (HR=2.16, CI=0.28-16.95, p=0.46).

To evaluate the discriminatory ability of crOTU 1614 in relation to known clinical risk factors of relapse/POD, a concordance index (C-index) was used in which a value closer to 1 indicates greater accuracy (FIG. 28). (See Wolbers et al., *Biostatistics*, 2014; 15:526-39). The discriminatory ability of crOTU 1614 (C-index=0.572) was comparable to the RDRI (C-index=0.569). The combination of crOTU 1614, RDRI, graft source, and conditioning intensity produced a moderately stronger discriminatory power (C-index=0.650) than the three clinical factors alone (C-index=0.619). This degree of predictive power is comparable to established models for other outcomes after allo-HCT (see Sorror et al., *J Clin Oncol* 2014; 32:3249-56) and indicates that an intestinal microbiota biomarker can add to currently known clinical risk assessments of relapse/POD.

Transplantation Parameters and Other Outcomes

Intestinal presence of crOTU 1614 was associated with an increase in overall survival (HR=0.65, CI=0.47-0.90, p=0.008, FIG. 29) and decreased cumulative incidence of relapse/POD (FIG. 29). The crOTU was not significantly associated with acute GVHD (grade 2-4, HR=0.81, CI=0.56-1.17, p=0.27) nor transplant-related mortality (HR=1.0, CI=0.63-1.59, p=0.99, FIG. 29). In light of the heterogeneity of the population under study, the association of crOTU 1614 with relapse/POD in patient subsets according to graft source, conditioning intensity, extent of HLA match, RDRI, and disease type (FIG. 30).

With respect to disease type, the association of crOTU 1614 with a reduced risk of relapse/POD was significant among patients with AML (HR=0.56, CI=0.32-0.96, p=0.04) and multiple myeloma (HR=0.29, CI=0.12-0.67, p=0.004) and not statistically significant for other disease types. For graft source (FIGS. 29 and 30), the association of crOTU 1614 with reduced risk of relapse/POD was significant in recipients of T-cell replete transplants (HR=0.40, CI=0.24-0.65, p<0.001), particularly among recipients of unmodified PBSC/BM grafts (HR=0.40, CI=0.23-0.69, p=0.001). A significant association was neither observed in recipients of T-cell-depleted grafts (HR=0.66, CI=0.39-1.11, p=0.12) nor in recipients of cord grafts (HR=0.38, CI=0.11-1.32, p=0.13, FIG. 29).

Pre-Transplant Samples

As demonstrated supra, a biomarker of relapse risk is useful for evaluating and treating patients treated with HSCT. Such a biomarker has additional utility if it provides information on risk of relapse prior to transplantation, e.g., as part of a decision making process for what treatment regime is to be used for a patient. Among the 172 recipients of unmodified PBSC/BM (T-cell replete) grafts in whom the association of crOTU 1614 was most clear, 143 patients (83%) also had a sample collected in the three weeks prior to stem-cell infusion. These patients were stratified into four bins based upon the abundance of crOTU 1614 in a single stool sample collected during the three weeks preceding allo-HCT. If more than one sample was available from the three weeks preceding allo-HCT, the sample collected closest to day −10 was selected for analysis. The patients in the highest abundance bin had a lower risk of relapse/POD compared with the combined three lower-abundance groups (HR=0.28, CI=0.10-0.80, p=0.02, FIG. 32). A similar, though less statistically significant association between decreased risk of relapse/POD and crOTU 1614 in pre-transplant samples was also observed in the 469 recipients of all types of graft sources who had pre-transplant samples available (FIG. 33, HR=0.63, CI=0.40-1.09, p=0.06). Thus, intestinal presence of crOTU 1614 or a subset of crOTU 1614 organisms, either before or after allo-HCT, can be used as a biomarker of post-transplant relapse/POD risk. FIG. 34 shows the category boundaries for abundance bins used throughout the study, as depicted by FIGS. 26B, 26C, 32 and 33.

Discussion

In this retrospective observational single-center study, the intestinal microbiota composition was studied for the largest cohort of allo-HCT patients assembled for this type of analysis to date. A discovery-validation approach was used to identify an association (FIG. 23) between abundance of a particular subset of intestinal bacteria and a decreased risk of relapse/POD after allo-HCT.

The association of this biomarker with a lower risk of relapse/POD was strongest among recipients of grafts containing T-cells and other mature lymphocytes (FIG. 30). In these patients there may be a greater role for donor-cell-mediated GVT activity as compared with recipients of T-cell depleted grafts, which suggests that the composition of the intestinal microbiota could be modulating GVT activity.

The group of intestinal bacteria associated with GVT activity is mostly comprised of *Eubacterium limosum*, an anaerobic, non-spore-forming gram-positive rod that is a common member of the human intestinal microbiota. (See Rajilic-Stojanovic et al., *FEMS Microbiol Rev* 2014; 38:996-1047).

Moreover, consideration of cumulative microbial exposures as time-weighted averages of abundance allowed many more samples per patient to be included in order to potentially reduce biases that could have occurred by sampling only single time points. Additionally, the empirical derivation of crOTUs combined the abundances of evolutionarily related OTUs as determined by 16S sequence similarity. (Table 5). One limitation of a traditional OTU-level analysis is that the association strength of a single species is sometimes distributed among multiple OTUs. On the other hand, in an analysis of higher taxonomic levels such as genus or family, potential associations may be lost when dozens or hundreds of OTUs are grouped together. The crOTU identified in this Example contains mostly members of family Eubacteriacae (FIG. 24) with smaller contributions from other families, but it did not include any of the 15 other species of family Eubacteriaceae that were present in the dataset. In fact, when OTUs were grouped into standard taxonomic classifications, neither genus *Eubacterium* as a whole, nor family Eubacteriaceae had a significant association with relapse/POD. Of note, the main OTU representing *Eubacterium limosum* was associated with less relapse risk. This illustrates the utility of grouping OTUs into empirically derived phylogenetic groups in the study of associations between microbiota and clinical outcomes. Moreover, these data show that 16S rRNA sequence similarity can be a better measure of evolutionary proximity than phenotypic traits.

Example 4

Methods of Reducing Cancer Relapse in an Animal Model by Administering a Composition Comprising Therapeutic Bacteria An association between certain members of the intestinal microbiota with decreased risk of relapse after allogeneic hematopoietic cell transplantation (for example, when T cells are present in the graft), is described by Examples 1-3. The present example describes a method of determining that said bacteria in the intestinal flora can augment graft-vs-tumor (GVT) and graft-versus-leukemia (GVL) activity. In such a model, GVT or GVL will also be augmented by antibiotics and by reintroduction of said bacteria, for example, *Eubacterium limosum* and/or *Parvimonas micra*, into the intestinal microbiota.

Methods

1. The Effect of Antibiotic Treatment on GVT Activity in a Mouse Models

In one model of GVT, after luciferase-expressing tumor cells and T-cell-depleted mismatched bone marrow (BM) with or without T cells are injected into mice, tumor burden can be monitored serially by bioluminescent imaging. Derivatives of the mouse B cell lymphoma A20 and the mouse T cell lymphoma EL4 harboring a luciferase-expression construct will be injected into mice intravenously in limiting serial dilutions to define the dose that is lethal to 50% of animals in 2-4 weeks. Mice will then be injected with this concentration of cells along with T-cell-depleted mismatched bone marrow (BM) with or without T cells, and then treated with antibiotics according to one of two different regimens (broad-spectrum gut decontamination or a defined spectra). Following treatment with antibiotics, GVT will be assayed by in vivo bioluminescence imaging, survival analysis, and by histology. Gut flora of the mice will be manipulated in two different ways. The first is gut broad-spectrum decontamination with oral vancomycin and ampicillin. A second will be to alter the composition of the flora by employing drugs with defined spectra. Since both *Eubacterium limosum* and *Parvimonas micra* are anaerobes, the effect of aztreonam (which lacks anaerobic activity) will be compared with imipenem (which has potent anaerobic activity).

The present experiment will therefore determine whether the presence of *Eubacterium limosum* and *Parvimonas micra* can reduce tumor presence in the mouse model of GVT.

2. The Effect of Intestinal *Eubacterium Limosum* and *Parvimonas Micra* on GVT Activity One drawback to standard experimental models is that the clinical correlation of tumor cell lines is limited by key differences between them and GVT reactions in patients. As an alternative, an experimental model of graft-versus-leukemia (GVL) was developed for mixed lineage leukemia (MLL)-related acute myeloid leukemia (AML). Rearrangements involving the MLL gene are particularly relevant for transplant studies, as they are highly prevalent in therapy-related AML, carry a poor clinical prognosis, and are an indication for allogeneic transplantation. (DiMartino et al., British Journal of Haematology 106, 614-626 (1999)). Following treatment with gut-decontaminating antibiotics, AML will be induced by injection of mice with GFP expressing bone marrow cells retrovirally transfected with an MLL-AF9 fusion construct that recapitulates a common MLL translocation (Stubbs et al., Leukemia 22, 66-77 (2007); and Krivtsov et al., Nature 442, 818-822 (2006)), followed by mismatched transplant of T-cell-depleted BM with or without T cells. This model of high-risk secondary leukemia utilizes a freshly generated leukemia with a defined genetic defect and reflects clinical disease more closely than in vitro-passaged tumor cell lines. Tumor progression will be monitored by transplant outcome and GFP fluorescence indicating leukemia in peripheral blood, spleen, and marrow.

Next, C57BL/6 mice bearing cell-line-derived lymphomas (for GVT analysis) or MLL-AF9 induced AML (for GVL analysis) will be treated with oral vancomycin and ampicillin, then colonized through oral gavage with bacteria and later transplanted with MHC-disparate B10.BR bone marrow and T cells. Commercially available strains of *Eubacterium limosum* and *Parvimonas micra* will first be used. Outcomes that will be evaluated in the mice include tumor burden by bioluminescence for luciferase-expressing tumors or flow cytometry for GFP-expressing leukemia, survival, and day 14 and 21 tissue histology.

The present experiment will therefore determine whether the presence of *Eubacterium limosum* and *Parvimonas micra* can reduce tumor presence in the mouse model of GVT and GVL.

In all of the foregoing mouse studies of the present Example, experiments will include 10 mice per group and will be repeated at least twice. Kaplan-Meier methods will be used to estimate overall survival in mouse transplant studies and a permutation-based logrank test will compare survival across treatment groups. For each experiment, a total of 10 mice per group will provide 80% power to detect an odds parameter of 5.

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. All technical features can be individually combined in all possible combinations of such features. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods or steps.

Patents, patent applications publications product descriptions, and protocols are cited throughout, the disclosures of which are incorporated herein by reference in their entireties for all purposes.

We claim:

1. A method for reducing the risk of cancer relapse or increasing likelihood of survival from a cancer relapse in a subject, comprising administering, to a subject in need of such treatment, an effective amount of a pharmaceutical composition comprising one or more isolated bacteria, wherein the isolated bacteria comprise a 16S rDNA sequence that has between about 95 and 100% identity with a nucleic acid sequence described by SEQ ID NO:1, and further comprising a biocompatible pharmaceutical carrier; and wherein the subject has had a hematopoietic stem cell transplantation (HSCT).

2. The method of claim 1, wherein the pharmaceutical composition is administered in an amount effective to decrease the presence of *Enterococcus faecium* in the subject, and/or decrease the amount of *Enterococcus faecium* toxin in the subject.

3. The method of claim 1, further comprising identifying a subject at risk of cancer relapse comprising:
obtaining an intestinal microbiota sample from a subject and determining the level of one or more bacteria present in the intestinal microbiota sample;
comparing the level of the one or more bacteria in the sample with a reference bacteria level; and
administering the pharmaceutical composition to the subject when the level of the one or more bacteria in the sample is lower than the bacteria reference level.

4. The method of claim 1, further comprising identifying a subject at risk of cancer relapse comprising:
obtaining an intestinal microbiota sample from a subject and determining the level of *Enterococcus faecium* bacteria present in the intestinal microbiota sample;
comparing the level of the bacteria in the sample with a reference bacteria level; and
administering the pharmaceutical composition to the subject when the level of bacteria in the sample is greater than the bacteria reference level.

5. The method of claim 1, wherein the isolated bacteria comprise a 16S rDNA sequence having about 97% identity with SEQ ID NO:1.

6. The method of claim 1, wherein the isolated bacteria is *Eubacterium limosum*.

7. The method of claim 1, wherein the pharmaceutical composition is administered orally, nasogastrically, or rectally.

8. The method of claim 1, wherein the HSCT is an allogenic hematopoietic stem cell transplantation (allo-HSCT).

9. The method of claim 8, wherein the allo-HSCT is a T-cell replete allo-HSCT.

10. The method of claim 1, wherein the isolated bacteria comprise a 16S rDNA sequence described by SEQ ID NO:1.

11. The method of claim 1, further comprising administering to the subject a prebiotic, a postbiotic, an antibiotic, surgery, radiation therapy, chemotherapy, immunotherapy, stem cellular therapy, cellular therapy, or a combination thereof.

12. The method of claim 1, wherein the pharmaceutical composition is a liquid, suspension, dried powder, tablet, capsule, or food product.

\* \* \* \* \*

SEQUENCE LISTING

<160> NUMBER OF SEQ ID NOS: 17

<210> SEQ ID NO 1
<211> LENGTH: 1484
<212> TYPE: DNA
<213> ORGANISM: Eubacterium limosum

<400> SEQUENCE: 1

```
agagtttgat cctggctcag gacgaacgct ggcggtatgc ttaacacatg caagtcgaac      60
gagaaggttt tgatggatcc ttcgggtgac attagaactg gaaagtggcg aacgggtgag     120
taacgcgtgg gtaacctgcc ctatggaaag gaatagcctc gggaaactgg gagtaaagcc    180
ttatattatg gttttgtcgc atggcaagat catgaaaact ccggtgccat aggatggacc    240
cgcgtcccat tagctagttg gtgagataac agcccaccaa ggcgacgatg gtaaccggt     300 ctgagagggc gaacggtcac actggaactg agacacggtc cagactccta cgggaggcag    360
cagtggggaa tattgcgcaa tgggggcaac cctgacgcag caataccgcg tgagtgaaga    420
aggttttcgg atcgtaaagc tctgttattg gggaagaaga atgacggtac ccaatgagga    480
agtcccggct aactacgtgc cagcagccgc ggtaatacgt aggggacaag cgttgtccgg    540
aatgactggg cgtaaagggc gcgtaggcgg tctattaagt ctgatgtgaa aggtaccggc    600
tcaaccggtg aagtgcattg gaaactggta gacttgagta ttggagaggc aagtggaatt    660
cctagtgtag cggtgaaatg cgtagatatt aggaggaaca ccagtggcga aggcggcttg    720
ctggacaaat actgacgctg aggtgcgaaa gcgtggggag cgaacaggat tagatacct    780 ggtagtccac gccgtaaacg atgaatgcta ggtgttgggg aaactcagtg ccgcagttaa    840
cacaataagc attccgcctg gggagtacga ccgcaaggtt gaaactcaaa ggaattgacg    900
gggacccgca caagcagcgg agcatgtggt ttaattcgaa gcaacgcgaa gaaccttacc    960
aggtcttgac atcctctgac gagcctagag ataggaagtt tccttcggga acagagagac   1020
aggtggtgca tggttgtcgt cagctcgtgt cgtgagatgt tgggttaagt cccgcaacga   1080
gcgcaacccc tgcctttagt tgccagcatt aagttgggca ctctagaggg actgccgtag   1140
acaatacgga ggaaggtggg gacgacgtca atcatcatg cccttatga cctgggctac    1200 acacgtgcta caatggtctg aacagagggc gcgaagccg cgaggtgaag caaatccctt   1260
aaaacagatc ccagttcgga ttgcaggctg caactcgcct gcatgaagtt ggagttgcta   1320
gtaatcgcgg atcagaatgc cgcggtgaat gcgttccgg gtcttgtaca caccgcccgt   1380
cacaccacga gagttggcaa caccgaagc ctgtgagaga accgcaagga ctcagcagtc   1440
gaaggtgggg ctagtaattg gggtgaagtc gtaacaaggt aacc              1484
```

<210> SEQ ID NO 2
<211> LENGTH: 1393
<212> TYPE: DNA

<213> ORGANISM: Peptococcus niger

<400> SEQUENCE: 2

```
gcctaataca tgcaagtcga acggacgagg aaagagacct cttcggagtg acctttcccg      60
agttagtggc ggatgggtga gtaacgcgtg agtgacctgc ccagcagtgg ggaataacag     120
tgagaaatca ttgctaatac cgcatatctt acaagtgctt catggtacct gtaagaaaga     180
cggccttcgt gctgtcgctg ttggatggac tcgcgtctga ttagccagtt ggtgggtaa     240
cggcctacca aagcaatgat cagtagccgg cctgagaggg tgaacggcca cattgggact     300
gagacacggc ccaaactcct acgggaggca gcagtgggga tcttccgca atgggcgcaa     360
gcctgacgga gcaatgccgc gtgagtgaag aaggccttcg ggttgtaaaa ctctgtcctc     420
atccaagaga ggggaaggta gtaactgacc tttccaggac ggtagatgag gaggaagccc     480
cggctaacta tgtgccagca gccgcggtaa aacataggg gcaagcgttg tccggaatca     540
ctgggcgtaa agggcgcgca ggcggtctgt taagtcagat gtgaaaggtt agggctcaac     600
cctgaacgtg catctgatac tggcagactt gagtatggaa gaggtaagtg gaattcctag     660
tgtagcggtg aaatgcgtag atattaggag gaacaccagt ggcgaaggcg acttactggg     720
ccataactga cgctgaggcg cgaaagcgtg gggagcaaac aggattagat accctggtag     780
tccacgccgt aaacgatggg tactaggtgt cggaggtttc aagaccgtcg gtgccgcagt     840
taacacaata agtaccccgc ctggggagta cggtcgcaag actgaaactc aaaggaattg     900
acgggggccc gcacaagcgg tggagcatgt ggtttaattc gacgcaacgc gaagaacctt     960
accaagactt gacatcctgc tgccgagtga tgtaatgtca cttttccttc gggacagcag    1020
agacaggtgg tgcatggttg tcgtcagctc gtgtcgtgag atgttgggtt aagtcccgca    1080
acgagcgcaa cccttgtcgt cagttgccat cattaagttg gcactctga cgagactgcc    1140
gcagacaatg cggaggaagg tggggatgac gtcaaatcat catgcccctt atgtcttggg    1200
ctacacacgt gctacaatgg tcggtacaga gggcagcgaa ggagcgatcc ggagccaatc    1260
tcacaaagcc gatcccagtt cggattgcag gctgcaactc gcctgcatga agtcggaatg    1320
cgtagtaatc gcaggtcagc atactgcggt gaatacgttc ccgggccttg tacacaccgc    1380
ccgtcacacc acg                                                       1393
```

<210> SEQ ID NO 3
<211> LENGTH: 1462
<212> TYPE: DNA
<213> ORGANISM: Anaerofustis stercorihominis

<400> SEQUENCE: 3

```
tggcggcgtg cttaacacat gcaagtcgaa cgagaaactt ataaatgatc cttcgggtga     60
atctataagc ggacagtggc gaacgggtga gtaacgcgta ggtaaccaac ctcatgcagg    120
gggatagccc agggaaactt ggattaaacc cgcataagac cacagcaccg catggtgcag    180
gggtaaaaac tccggtggca tgagacggac ctgcgtctta ttaggtagtt ggtgaggtaa    240
cggctcacca agccaacgat gagtagccga cctgagaggg tgatcggcca cattgggact    300
gagacacggc ccagactcct acgggaggca gcagtgggga atattgcgca atgggggaaa    360
ccctgacgca gcaacgccgc gtgagcgatg aaggttttcg gatcgtaaag ctctgtcttt    420
ggggaagata atgacggtac ccaaggagga agctccggct aactacgtgc cagcagccgc    480
ggtaatacgt agggagcaag cgttgtccgg attcactggg cgtaaagagc acgtaggcgg    540
ttaattaagt caggtgtgaa agttttcggc tcaaccggaa aagtgcactt gaaactggat    600
```

```
aacttgagta tcggagaggt aagcggaatt cctagtgtag cggtgaaatg cgtagagatt    660
aggaagaaca ccggtggcga aggcggctta ctggacgata actgacgctg aggtgcgaaa    720
gcgtggggag cgaacaggat tagatacccct ggtagtccac gccgtaaacg atgaatacta   780
ggtgttgggg taactcagtg ccgcagttaa cacattaagt attccgcctg gggagtacgc    840
tcgcaagagt gaaactcaaa ggaattgacg ggggcccgca caagcagcgg agcatgtggt    900
ttaattcgaa gcaacgcgaa gaaccttacc aggtcttgac atcccttgac cgcctaagag    960
attaggcttt ccttcgggac aaggagacag gtggtgcatg gttgtcgtca gctcgtgtcg   1020
tgagatgttg ggttaagtcc cgcaacgagc gcaacccctta tgtttagtta ctaacattca   1080
gttgaggact ctagacagac tgcccttgaa agagggagga aggtggggac gacgtcaaat   1140
catcatgccc cttacgacct gggctacaca cgtgctacaa tggtctgtac agagggttgc   1200
gaagcagtga tgctaagcta atctcaaaaa gcagatctca gttcggattg caggctgcaa   1260
ctcgcctgca tgaagtcgga gttgctagta atcgcgaatc agaatgtcgc ggtgaatgcg   1320
ttcccgggcc ttgtacacac cgcccgtcac accacgagag ttggtaacac ccgaagccag   1380
tgagctaacc attaggaggc agctgtcgaa ggtgggatca gtaattgggg tgaagtcgta   1440
acaaggtagc cgtatcggaa gg                                             1462

<210> SEQ ID NO 4
<211> LENGTH: 1510
<212> TYPE: DNA
<213> ORGANISM: Saccharofermentans acetigenes

<400> SEQUENCE: 4
ttgatcctgg ctcaggatga acgctggcgg cgtgcctaac acatgcaagt cgagcggaga    60
tgagaagagt acttgtacga atttcatctt agcggcggac gggtgagtaa tgcgtgagga   120
acctgccttt cactggggaa taacatcgag aaatcggtgc taataccgca taaagtcgcg   180
agatcgcatg gttttgcgac caaaggagca atccggtgaa gatggactc acgtccgatt    240 aggtagttgg tgaggtaacg gcccaccaag cctacgatcg gtagccgaac tgagaggttg   300
atcggccaca ttgggactga gacacggccc agactcctac gggaggcagc agtggggaat   360
attgggcaat gggcgaaagc ctgacccagc aacgccgcgt gaaggaagaa ggtcttcgga   420
ttgtaaactt ctttgatcag ggacgaaaga atgacggta cctgaagaac aagccacggc    480
taactacgtg ccagcagccg cggtaatacg taggtggcaa gcgttatccg gatttactgg   540
gtgtaaaggg cgtgtaggcg gttctgcaag tcagatgtga aattcccggg cttaacccgg   600
gcgctgcatc tgaaactgca ggacttgagt actggagagg atagtggaat tcctagtgta   660
gcggtaaaat gcgtagatat taggaggaac accagtggcg aaggcggcta tctggacagt   720
aactgacgct gaggcgcgaa agcgtgggga gcaaacagga ttagataccc tggtagtcca   780
cgccgtaaac gatgaatact aggtgtaggg ggtatcgact cccctgtgc cgcagctaac   840 gcaataagta ttccacctgg ggagtacggc cgcaaggttg aaactcaaag gaattgacgg   900
gggcccgcac aagcagtgga ttatgtggtt taattcgaag caacgcgaag aaccttacca   960
ggacttgaca tcccttgacc ggcatagaga tatgccttc cttcgggaca aggagagcag   1020
gtggtgcatg gttgtcgtca gctcgtgtcg tgagatgttg ggttaagtcc cgcaacgagc   1080 gcaacccccta ttgccagttg ccatcattca gttgggaact ctggcgatac tgccgtggac   1140
aacacggagg aaggtgggga cgacgtcaaa tcatcatgcc ccttatgtcc tgggctacac   1200
```

```
acgtaataca atggcaacga cagagggcag ctactccgcg aggacaagcg aatccctaaa    1260
cgttgtctca gttcggattg caggctgcaa ctcgcctgca tgaagtcgga attgctagta    1320
atggcaggtc agcatactgc cgtgaatacg ttcccgggcc ttgtacacac cgcccgtcac    1380
accatgagag tctgcaatac ccgaagtcag tagtctaacc gcaaggggga cgctgccgaa    1440
ggtagggccg ataattgggg tgaagtcgta acaaggtagc cgtatcggaa ggtgcggctg    1500
gatcacctcc                                                           1510
```

<210> SEQ ID NO 5
<211> LENGTH: 1438
<212> TYPE: DNA
<213> ORGANISM: Armatimonas rosea

<400> SEQUENCE: 5

```
gacgaacgct gcggcgtgcc taagaaatgc aagtcgaacg acagtggct tcggttactg      60 ttagtggcga acgtcgcgt aacacgtaag aaacctgcct cgaagcgggg gacaacagtc     120
cgaaaggact gctaataccg catgtggcca gtcgggggca tccccgattg tctaaagatt    180
tatcacttcg agatggtctt gcggcctatc agctagttgg tggggtaacg gcctaccaag    240
gcgacgacgg gtagctggtc tgagaggacg atcagccgga ttgggactga gatacggccc    300
agactcctac ggggggcagc aattaggaat cttgcacaat gggcgaaagc ctgatgcagc    360
gacgccgcgt gaaggatgaa ggttctcgga tcgtaaactt ctttttaagtg ggaagaaatt    420 tgacggtacc acttgaataa gccccggcta actacgtgcc agcagccgcg gtaatacgta    480
gggggcgagc gttgtccgaa gttactgggc gtaaagcgcg cgtaggcggt ttcttaagtc    540
tggggtgaaa ggttcaacgc tcaacgtgaa cagtgccttg gatactggga acttgagtt    600 agggagaggg tagtagaatt cctggtgtag cggtgaaatg cgtagatatc aggaggaata    660
ccaatggcga aggcagctac ctggcctata actgacgctg aggtgcgaaa gcgtggggag    720
caaacgggat tagataccccc ggtagtccac gccctaaacg atgagtgcta gatgtaagag    780
gtatcgaccc ctcttgtgtc gtcgctaacg cattaagcac tccgcctggg gagtacggcc    840
gcaaggttga aactcaaagg aattgacggg ggcccgcaca agcggtggag catgtggatt    900
aattcgtcac taaccgaaga accttaccca ggtttgacat cctaggaacc ctgatgaaag    960 ttggggtgc tcgcaagaga gcctagagac aggtgttgca tggctgtcgt cagctcgtgt    1020
cgtgagatgt tgggttaagt cccgcaacga gcgcaaccct caccgtatgt tggcagcgta    1080
aagtcggcaa ctcttacgga actgcccgtg caagcgggag gaaggtgggg atgacgtcaa    1140
gtcggcatgg cccttacgcc tggggcttca cacatgctac aatgggtggc aacaaagggc    1200
tgctaaaccg tgaggtcaag caaatcccaa aaatccatcc tcagttcgga ttgtaggctg    1260
caactcgcct acatgaagcc ggaatcgcta gtaaccgcag gtcagctaaa ctgcggtgaa    1320
tacgttcccg ggccttgtac acaccgcccg tcaagtcacc tgaattgtct gcacccgaag    1380
ccggtggcca aactcgcaag agatggagcc gtctaaggtg tggggagtaa ggggact        1438
```

<210> SEQ ID NO 6
<211> LENGTH: 1480
<212> TYPE: DNA
<213> ORGANISM: Pseudoramibacter alactolyticus

<400> SEQUENCE: 6

```
taagtcaaaa agaacagttt gatcatggct caggacgaac gctggcggta tgcttaacac     60
atgcaagtcg aacgagaagt ttttattga ccttcggggg atataagaga cagacagtgg    120
```

```
cgaacgggtg agtaacgcgt gggcaaccta cctatcggag cgggatagcc tcgagaaatc    180
gggagtaaaa ccgcataaca cagcagaatc gcatgacttt gctgtcaaaa ctccggtgcc    240
gatagatggg cccgcgtctg attagctagt tggtaaggta agggcttacc aaggcaacga    300
tcagtagccg gtctgagagg gcgaacggcc acactgaaac tgagacacgg tccagactcc    360
tacgggaggc agcagtgggg aatattgcgc aatgggggca accctgacgc agcaataccg    420
cgtgagtgaa gaaggtttc ggatcgtaaa gctctgttat ggggaagaa gcagtgacgg    480 tacccaatga ggaagtcccg gctaactacg tgccagcagc cgcggtaata cgtaggggac    540
gagcgttgtc cggaatcact gggcgtaaag ggcgcgtagg cggttttata agtcagatgt    600
gaaaggtacc ggctcaaccg gtgacgtgca tttgaaactg taagacttga gtactgaaga    660
ggcaagcgga attcctagtg tagcggtgaa atgcgtagat attaggaaga acaccggtgg    720
cgaaggcggc ttgctgggca gatactgacg ctgaggtgcg aaagcgtggg gagcgaacag    780
gattagatac cctggtagtc cacgccgtaa acgatgaata ctaggtgttg gcgaataagt    840
cagtgccgga gttaacacaa taagtattcc gcctggggag tacgaccgca aggttgaaac    900
tcaaaggaat tgacggggac ccgcacaagc agcggagcat gtggtttaat tcgaagcaac    960
gcgaagaacc ttaccaggcc ttgacatcct ctgagcgcaa tagagatatt gctttccctt   1020
cggagacaga gagacaggtg gtgcatggtt gtcgtcagct cgtgtcgtga tgttgggt    1080 taagtcccgc aacgagcgca accctgtca ttagttgcca tcattgagtt gggcactcta   1140
atgagactgc cgtagacaat acggaggaag gtggggacga cgtcaaatca tcatgcccct   1200
tatggcctgg gctacacacg tgctacaatg gtctgaacaa agggaagcga aggagcgatt   1260
cggagcgaat ctcataaaac agatcccagt tcggattgca ggctgcaact cgcctgcatg   1320
aagatggagt tgctagtaat cgcggatcag aatgtcgcgg tgaatgcgtt cccgggtctt   1380
gtacacaccg cccgtcacac cacgagagtc ggtaacaccc gaagccagtg agacaaccgg   1440
aaggagtcag ctgtcgaagg tgggatcggt aattggggtg                         1480
```

<210> SEQ ID NO 7
<211> LENGTH: 1483
<212> TYPE: DNA
<213> ORGANISM: Finegoldia magna

<400> SEQUENCE: 7

```
agagtttgat cctggctcag gacgaacgct ggcggcgtgc ttaacacatg caagtcgaac     60
gggatttagt agacagaagc ttcggtggaa gattactaat gagagtggcg aacgggtgag    120
taacgcgtga gcaacctgcc tatgacagtg ggatagcctc gggaaaccgg gattaatacc    180
gcataaaatc gtagaaacac atgttttaac ggtcaaagat ttatcggtca tagatgggct    240
cgcgtctgat tagctagttg gtgagataac agcccaccaa ggcgacgatc agtagccggt    300
ctgagaggat gaacggccac attggaactg agacacggtc caaactccta cgggaggcag    360
cagtggggaa tattgcacaa tgggggaaac cctgatgcag cgacgccgcg tgaacgaaga    420
aggtattcgt atcgtaaagt tctgtcctat gggaagataa tgacagtacc atagaagaaa    480
gctccggcta aatacgtgcc agcagccgcg gtaatacgta tggagcgagc gttgtccgga    540
attattgggc gtaaagggta cgcaggcggt ttaataagtc gaatgttaaa gatcggggct    600
caaccccgta aagcattgga aactgataaa cttgagtagt ggagaggaaa gtggaattcc    660
tagtgtagtg gtgaaatacg tagatattag gaggaatacc agtagcgaag gcgactttct    720
```

| | |
|---|---|
| ggacacaaac tgacgctgag gtacgaaagc gtggggagca acaggattaga gataccctgg | 780 |
| tagtccacgc cgtaaacgat gaatgctagg tgttgggggt caaacctcgg tgccgaagtt | 840 |
| aacacattaa gcattccgcc tggggagtac gcacgcaagt gtgaaactca aaggaattga | 900 |
| cggggacccg cacaagcagc ggagcatgtg gtttaattcg atgcaacgcg aagaacctta | 960 |
| ccagggcttg acatgtgggt gaaaggtata gagatatacc cctctcttta tgagacatcc | 1020 |
| atacaggtgg tgcatggttg tcgtcagctc gtgtcgtgag atgttgggtt aagtcccgca | 1080 |
| acgagcgcaa cccctatact tagttaccag cgagtaaagt cggggactct aagtagactg | 1140 |
| ccgatgacaa atcggaggaa ggtggggatg acgtcaaatc atcatgccct ttatgtcctg | 1200 |
| ggctacacac gtgctacaat ggttggtaca gagggaagct atatagtgat ataatgcaaa | 1260 |
| actccaaagc caatcccagt tcggattgta ggctgcaact cgcctacatg aagtcggagt | 1320 |
| tgctagtaat cgcggatcag aatgtcgcgg tgaatgcgtt cccgggtctt gtacacaccg | 1380 |
| cccgtcacac catgggagtt gataataccc gaagcctgtg acctaattga ggagcagtcg | 1440 |
| aaggtaggat tgatgactgg ggtgaagtcg taacaaggta acc | 1483 |

<210> SEQ ID NO 8
<211> LENGTH: 1362
<212> TYPE: DNA
<213> ORGANISM: Murdochiella asaccharolytica
<220> FEATURE:
<221> NAME/KEY: misc_feature
<222> LOCATION: (643)..(643)
<223> OTHER INFORMATION: n is a, c, g, or t

<400> SEQUENCE: 8

| | |
|---|---|
| aacgagaatg tactgacgga tccttagggt gaagatagta caggacagtg gcggatgggt | 60 |
| gagtaacgcg taagaaacct gcctttcaca ccgggatagc agctggaaac ggctattaat | 120 |
| accggatgac acttttttccc cgcatgagga agaggttaaa gaatttcggt gaaagatggt | 180 |
| cttgcgtctg attagctagt tggtgggggta acggcctacc aaggcgacga tcagtagccg | 240 |
| gcctgagagg gtgtacggcc acattgggac tgagacacgg cccaaactcc tacgggaggc | 300 |
| agcagtgggg aattttgcac aatggaggaa actctgatgc agcgacgccg cgtgaacgaa | 360 |
| gaaggtcttc ggattgtaaa gttctgtcct gggtgaagat aatgacggta actcaggagg | 420 |
| aagccccggc taactacgtg ccagcagccg cggtaatacg tagggggcga gcgttgttcg | 480 |
| gaattattgg gcgtaaaggg tacgtaggcg gtttgttaag tttggcgtta aatcacgggg | 540 |
| ctcaaccccg ttcagcgttg aaaactggca aacttgagta gtagagggga cagtggaatt | 600 |
| cctagtgtag cggtgaaatg cgtagagatt aggaagaata ccngtggcga aggcgactgt | 660 |
| ctggatacat actgacgctc aggtacgaaa gcgtggggag caaacaggat tagataccct | 720 |
| ggtagtccac gccctaaacg atgagtgcta ggtgtcgggt gtcaaagctc ggtgccgccg | 780 |
| ttaacacatt aagcactccg cctggggagt acgcacgcaa gtgtgaaact caaatgaatt | 840 |
| gacggagacc cgcacaagta gcggagcatg tggtttaatt cgaagcaacg cgaagaacct | 900 |
| taccagggct tgacataaca gtgacgggtt aagagattaa ccgttccctt cggggacact | 960 |
| gctacaggtg gtgcatggtt gtcgtcagct cgtgtcgtga tgttgggt taagtcccgc | 1020 |
| aacgagcgca acccttgtcg ttagttgcca gcattgagtt ggggactcta gcgagactgc | 1080 |
| cggtgataaa ccggaggaag gtggggatga cgtcaaatca tcatgccctt tatgtcctgg | 1140 |
| gctacacacg tgctacaatg gccgaaaaca gcgtgaagca acctcgtgag agcaagcgaa | 1200 |
| ccacgaaaag tcggtctcag ttcggactgt aggctgcaac tcgcctacac gaagtcggag | 1260 |

<210> SEQ ID NO 9
<211> LENGTH: 1489
<212> TYPE: DNA
<213> ORGANISM: Levyella massiliensis

<400> SEQUENCE: 9

```
tagagtttga tcctggctca ggataaacgc tggcggcgtg cgtaacacat gcaagtcgaa      60
cgagaatgtg ctgacggatc cttagggtga agatagcaca ggacagtggc ggatgggtga     120
gtaacgcgta agaaacctgc ctttcacacc gggatagcag ctggaaacgg ctattaatac     180
cggatgacac ttttcccccg catgaggaag aggttaaaga atttcggtga agatggtct      240
tgcgtctgat tagctagttg gtggggtaac ggcctaccaa ggcgacgatc agtagccggc     300
ctgagagggt gtacggccac attgggactg agacacggcc caaactccta cgggaggcag     360
cagtggggaa ttttgcacaa tggaggaaac tctgatgcag cgacgccgcg tgaacgaaga     420
aggtcttcgg attgtaaagt tctgtcctgg gtgaagataa tgacggtaac tcaggaggaa     480
gccccggcta actacgtgcc agcagccgcg gtaatacgta ggggcgagc gttgttcgga     540
attattgggc gtaaagggta cgtaggcggt ttgttaagtt tggcgttaaa tcacggggct     600
caacccgtt cagcgttgaa aactggcaaa cttgagtagt agaggggaca gtggaattcc     660
tagtgtagcg gtgaaatgcg tagagattag gaagaatacc ggtggcgaag gcgactgtct     720
ggatacatac tgacgctcag gtacgaaagc gtggggagca acaggattta gatacctgg     780
tagtccacgc cctaaacgat gagtgctagg tgtcgggtgt caaagcccgg tgccgccgtt     840
aacacattaa gcactccgcc tggggagtac gcacgcaagt gtgaaactca aaggaattga     900
cggggacccg cacaagtagc ggagcatgtg gtttaattcg aagcaacgcg aagaacctta     960
ccagggcttg acataacagt gacgggttaa gagattaacc gttcccttcg ggacactgc    1020
tacaggtggt gcatggttgt cgtcagctcg tgtcgtgaga tgttgggtta agtcccgcaa    1080
cgagcgcaac ccttgtcgtt agttgccagc attaagttgg ggactctagc gagactgccg    1140
gtgataaacc ggaggaaggt ggggatgacg tcaaatcatc atgcccttta tgtcctgggc    1200
tacacacgtg ctacaatggc cgaaaacagc gtgaagcaac ctcgtgagag caagcgaacc    1260
acgaaaagtc ggtctcagtt cggactgtag gctgcaactc gcctacacga agtcggagtt    1320
actagtaatc gcgaatcagc atgtcgcggt gaatgcgttc ccgggtcttg tacacaccgc    1380
ccgtcacacc atggaagttg gtaatacccg aagccgctga gcgaacctat gacgcaggcg    1440
tcgaaggtag gatcaatgac tggggtgaag tcgtaacaag gtagccgta              1489
```

<210> SEQ ID NO 10
<211> LENGTH: 1357
<212> TYPE: DNA
<213> ORGANISM: Gallicola barnesae
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (493)..(496)

<223> OTHER INFORMATION: n is a, c, g, or t
<220> FEATURE:
<221> NAME/KEY: misc_feature
<222> LOCATION: (888)..(895)
<223> OTHER INFORMATION: n is a, c, g, or t

<400> SEQUENCE: 10

| | | | | | |
|---|---|---|---|---|---|
| cgaacgctgg | cggcgtgatn | aaaacatgca | agtcgaacga | tcaccctttcc | attntctat | 60 |
| tcggagagat | tgaggagcgg | gttaggggag | aggggttgaa | taacgtgtga | gccaccctgt | 120 |
| ctaaacaagg | ggatagcctc | gggactccgg | gatttattcc | gtatgagacc | ccgccttccc | 180 |
| atgtagaaga | ggttcaaaga | tttttatcggt | ttaagatggg | ctcgcgtctg | attagctagt | 240 |
| tggtgagata | aaagcccacc | aagtcaacga | tcagtaaccg | gcttgagaga | gtgaacggtc | 300 |
| acattggaca | ctgagacacg | gtccaaactc | ctcagggagg | cagcagtggg | gaatattgca | 360 |
| caatggggga | aaccctgatg | cagcgacgcc | gcgtgagcga | tgaaggaatt | cgtttcgtaa | 420 |
| agctctgtcc | taggggaaga | taatgacagt | acccttggag | gaagcccggg | ctaaatacgt | 480 |
| gcgcagcagc | cgnnnnttac | gtatgggcg | agcgttgtcc | ggaattattg | ggcgtaaagg | 540 |
| gtacgtaggc | ggtttcataa | gtcagatgta | aaagcgtggg | gctcaacccc | ataaagcatt | 600 |
| tgaaactgtg | gaacttgagt | agtggagagg | aaagtggaat | tcctagtgta | gcggtgaaat | 660 |
| gcgtagatat | taggaggaat | accagtggcg | aaggcgactt | tctggacaca | aactgacgct | 720 |
| gaggtacgaa | agcatgggga | gcacacagga | ttagataccc | tggtagtcca | tgccgtaaac | 780 |
| gatgaatgct | aggtgtcggg | ggtcaaacct | cggtgccgca | gttaacacag | taagcattcc | 840 |
| gcctggggag | tacggtggca | acactgaaac | tcaatggatc | aaatgaannn | nnnnnggccc | 900 |
| gcgcaagcag | cggagcatgt | ggtttatttc | gatgcaacgc | gaagaacctt | accaggactt | 960 |
| gacatataga | tgaaagatct | agagatagat | ccctctcttc | ggagacagct | atacaggtgg | 1020 |
| tgcatggttg | tcgtcagctc | gtgtcgtgag | atgttgggtt | aagtcccgca | acgagcgcac | 1080 |
| cccctatagc | tagttaccag | cacttcgggt | ggggactcta | gttagactgc | cgatgataaa | 1140 |
| tcggaggaag | gtggggatga | cgtcaaatca | tcatgccctt | tatgtcctgg | gctacacacg | 1200 |
| tgctacaatg | gtcggtacag | agggcagcga | gactgtgaag | ttaagcgaat | ctcagaaagc | 1260 |
| cgaccccagt | tcggattgca | ggcttgcaac | tcgcctgcat | gaagtcggag | ttggtagtaa | 1320 |
| tcgcagatca | gaatgctgcg | gtgaatgctt | gccgctc | | | 1357 |

<210> SEQ ID NO 11
<211> LENGTH: 1438
<212> TYPE: DNA
<213> ORGANISM: Eubacterium brachy

<400> SEQUENCE: 11

| | | | | | |
|---|---|---|---|---|---|
| gatgaacgct | ggcggcgtgc | ttaacacatg | caagtcgagc | gagaagtttt | gaaaagattc | 60 |
| ttcggatgaa | atttaaaatg | gaaagcggcg | gacgggtgag | taacgcgtag | gcaaccatac | 120 |
| aaagggatag | catttggaaa | cgaatattaa | taccttatga | aacttaacta | gtgcatgcta | 180 |
| ggtaggtcaa | agatttatcg | gtatgggatg | ggcctgcgtc | tgactgccct | tagctagttg | 240 |
| gtgaggtaac | ggctcaccaa | ggcgacgatc | agtagccgac | ctgagagggt | gaacggccac | 300 |
| attggaactg | agacacggtc | caaactccta | cgggaggcag | cagtggggaa | tattgcacaa | 360 |
| tggggggaaac | cctgatgcag | caacgccgcg | tgaacgatga | aggcctttgg | gtcgtaaagt | 420 |
| tctgttctag | gtgatgaaaa | ctgacagtaa | cctaggagaa | agcccggct | aactccgtgc | 480 |
| cagcagccgc | ggtaatactg | gaggggggcaa | gcgttatccg | gaattattgg | gcgtaaaggg | 540 |

-continued

```
tacgtaggtg gccttttaag cgtagggtat aaggcaatgg ctcaaccatt gttcgcccta      600
tgaactggaa ggcttgagtg caggagagga aagcggaatt cctagtgtag cggtggaatg      660
catagatatt aggaggaaca tcagcggcga aggcggcttt ctggactgca actgacactg      720
aggtacgaaa gcgtggggag caaacaggat tagataccct ggtagtccac gccgtaaacg      780
atgagcacta ggtgtcgggg tcgtaaggct tcggtgccgt agttaacgca ttaagtgctc      840
cgcctgggga gtacgcacgc aagtgtgaaa ctcaaaggaa ttgacgggga cccgcacaag      900
cagcggagca tgtggtttaa ttcgaagcaa cgcgagaacc ttaccaggac ttgacatcct      960
tctgaccggt ctttaatagg acctttcttt gacagaaga acaggtggt gcatggttgt      1020
cgtcagctcg tgtcgtgaga tgttgggtta agtcccgcaa cgagcgcaac ccttgtcatt     1080
agttgccatc attaagttgg gcactctagt gagactgccg ggacaactc ggaggaaggt      1140
ggggatgacg tcaaatcatc atgcccctta tgttctgggc tacacacgtg ctacaatggc     1200
tggtacaaag agaagcaaga ccgcaaggtg agcaaagct caaaaaccag ccccagttcg      1260
gattgtaggc tgaaactcgc ctacatgaag tcggagttgc tagtaatcgc agatcagaat     1320
gctgcggtga atgcgttccc gggtcttgta cacaccgccc gtcacaccat ggaagttggg     1380
ggcgcccaaa gttggcagat aaatatgcta cctaaggtga aaccaatgac tggggtga      1438
```

<210> SEQ ID NO 12
<211> LENGTH: 1487
<212> TYPE: DNA
<213> ORGANISM: Parvimonas micra

<400> SEQUENCE: 12

```
agagtttgat cctggctcag gacgaacgct ggcggcgtgc ttaacacatg caagtcgaac       60
gtgattttg tggaaattct ttcgggaatg gaaatgaaat gaaagtggcg aacgggtgag      120
taacacgtga gcaacctacc ttacacaggg ggatagccgt tggaaacgac gattaatacc     180
gcatgagacc acagaatcgc atgatatagg ggtcaaagat ttatcggtgt aagaagggct     240
cgcgtctgat tagctagttg gaagggtaaa ggcctaccaa ggcgacgatc agtagccggt     300
ctgagaggat gaacggccac attggaactg agacacggtc caaactccta cgggaggcag    360
cagtggggaa tattgcacaa tggggggaac cctgatgcag cgacgccgcg tgagcgaaga    420
aggttttcga atcgtaaagc tctgtcctat gagaagataa tgacggtatc ataggaggaa     480
gccccggcta atacgtgcc agcagccgcg gtaatacgta tgggcgagc gttgtccgga      540
attattgggc gtaaagggta cgtaggcggt tttttaagtc aggtgtgaaa gcgtgaggct     600
taacctcatt aagcacttga aactggaaga cttgagtgaa ggagaggaaa gtggaattcc    660
tagtgtagcg gtgaaatgcg tagatattag gaggaatacc ggtggcgaag gcgactttct    720
ggacttttac tgacgctcag gtacgaaagc gtggggagca acaggatta gataccctgg     780
tagtccacgc cgtaaacgat gaatgctagg tgttgggagt caaatctcgg tgccgaagtt   840
aacacattaa gcattccgcc tggggagtac ggtggcaaca ctgaaactca aggaattga     900
cggggacccg cacaagcagc ggagcatgtg gtttaattcg aagcaacgcg aagaacctta    960
ccaaggcttg acatatagtt gagttattga aaattgata agtccctcgg acaactata     1020
caggtggtgc atggttgtcg tcagctcgtg tcgtgagatg ttgggttaag tcccgcaacg    1080
agcgcaaccc ttatcttcag ttgccagcac gtagaggtgg gaactctgga gagactgccg    1140
atgacaaatc ggaggaaggt ggggatgacg tcaaatcatc atgcccttta tgtcttgggc    1200
```

```
tacacacgtg ctacaatggt tggtacaacg agaagcgaga tagagatgtt aagcgaaact    1260
ctaaaaacca atctcagttc ggattgtagg ctgcaactcg cctacatgaa gtcggagttg    1320
ctagtaatcg cgaatcagaa tgtcgcggtg aatgcgttcc cgggtcttgt acacaccgcc    1380
cgtcacacca tgggagttgg caatacccga agccgccgat ctaaccgcaa ggaggaaggc    1440
gtcgaaggta gggttaatga ctggggtgaa gtcgtaacaa ggtaacc                  1487
```

<210> SEQ ID NO 13
<211> LENGTH: 1478
<212> TYPE: DNA
<213> ORGANISM: Streptococcus anginosus

<400> SEQUENCE: 13

```
gacgaacgct ggcggcgtgc ctaatacatg caagtaggac gcacagttta taccgtagct     60
tgctacacca tagactgtga gttgcgaacg ggtgagtaac gcgtaggtaa cctgcctatt    120
agagggggat aactattgga aacgatagct aataccgcat aacagtatgt aacacatgtt    180
agatgcttga aagatgcaat tgcatcgcta gtagatggac ctgcgttgta ttagctagta    240
ggtagggtaa tggcctacct aggcgacgat acatagccga cctgagaggg tgatcggcca    300
cactgggact gagacacggc ccagactcct acggaggca gcagtaggga atcttcggca    360 atgggggaa ccctgaccga gcaacgccgc gtgagtgaag aaggttttcg gatcgtaaag    420
ctctgttgtt aaggaagaac gagtgtgaga atggaaagtt catactgtga cggtacttaa    480
ccagaaaggg acggctaact acgtgccagc agccgcggta atacgtaggt cccgagcgtt    540
gtccggattt attgggcgta aagcgagcgc aggcggttag aaaagtctga agtgaaaggc    600
agtggctcaa ccattgtagg ctttggaaac tgtttaactt gagtgcagaa ggggagagtg    660
gaattccatg tgtagcggtg aaatgcgtag atatatggag gaacaccggt ggcgaaagcg    720
gctctctggt ctgtaactga cgctgaggct cgaaagcgtg gggagcgaac aggattagat    780
accctggtag tccacgccgt aaacgatgag tgctaggtgt tgggtccttt ccgggactca    840
gtgccgcagc taacgcatta agcactccgc ctggggagta cgaccgcaag gttgaaactc    900
aaaggaattg acgggggccc gcacaagcgg tggagcatgt ggtttaattc gaagcaacgc    960
gaagaacctt accaggtctt gacatcccga tgctatttct agagatagga agtttcttcg   1020
gaacatcggt gacaggtggt gcatggttgt cgtcagctcg tgtcgtgaga tgttgggtta   1080
agtcccgcaa cgagcgcaac ccttattgtt agttgccatc attaagttgg gcactctagc   1140
gagactgccg gtaataaacc ggaggaaggt ggggatgacg tcaaatcatc atgcccctta   1200
tgacctgggc tacacacgtg ctacaatggc tggtacaacg agtcgcaagc cggtgacggc   1260
aagctaatct ctgaaagcca gtctcagttc ggattgtagg ctgcaactcg cctacatgaa   1320
gtcggaatcg ctagtaatcg cggatcagca cgccgcggtg aatacgttcc cgggccttgt   1380
acacaccgcc cgtcacacca cgagagtttg taacacccga agtcggtgag gtaaccgtaa   1440
ggagccagcc gcctaaggtg ggatagatga ttggggtg                           1478
```

<210> SEQ ID NO 14
<211> LENGTH: 1487
<212> TYPE: DNA
<213> ORGANISM: Eubacterium biforme
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature

```
<222> LOCATION: (120)..(120)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (341)..(342)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (928)..(929)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (968)..(968)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1385)..(1385)
<223> OTHER INFORMATION: n is a, c, g, or t

<400> SEQUENCE: 14
caaatggaga gtttgatcct ggctcaggat naacgctggc ggcatgccta atacatgcaa      60
gtcgaacgag aggaaggaaa gcttgctttt ctgaatctag tggcgaacgg gtgagtaacn    120
cgtaggtaac ctgcccatgt gcccgggata acttctggaa acggatgcta aaccggata     180 ggtagcagac aagcatttga ctgctattaa agtggctaag gccatgaaca tggatggacc    240
tncggtgcat tagctagttg gtgaggtaac ggcccaccaa ggcgacgatg catagccggc    300
ctgagagggc ggacggccac attgggactg agacacggcc nnaactccta cgggaggcag    360
cagtagggaa ttttcgtcaa tgggggggaac cctgaacaga caatgccgcg tgagtgagga    420
aggtcttcgg atcgtaaagc tctgttgtaa gagaaaaacg acattcatag ggaatgatga    480
gtgagtgatg gtatcttacc agaaagtcac ggctaactac gtgccagcag ccgcggtaat    540
acgtaggtgg cgagcgttat ccggaatgat tgggcgtana gggtgcgtag gtggcagaac    600
aagtctggag taaaaggtat gggctcaacc cgtactggct ctggaaactg ttcagctaga    660
gaacagaaga ggacggcgga actccatgtg tagcggtaaa atgcgtagat atatggaaga    720
acaccggtgg cgaaggcggc cgtctggtct gttgctgaca ctgaagcacg aaagcgtggg    780
gagcaaatag gattagatac cctagtagtc cacgccgtaa acgatgagaa ctaggtgttg    840
ggggaataac tcagtgccgc agttaacgca ataagttctc cgcctgggga gtatgcacgc    900
aagtgtgaaa ctcaaaggaa ttgacggnng ccngcacaag cggtggagta tgtggtttaa    960
ttcgaagnaa cgcgaagaac cttaccaggc cttgacatcc cttgcagagr tatagagata   1020
tatccgaggt taacaaggag acaggtggtg catggttgtc gtcagctcgt gtcgtgagat   1080
gttgggttaa gtcccgcaac gagcgcaacc cttgtgatat gttactaaca ttgagttgag   1140
gactcatatc agactgccgg tgataaaccg gaggaaggtg gggatgacgt caaatcatca   1200
tgccccttat ggcctgggct acacacgtnc tacaatggcg tctacaaaga gcggcaagcc   1260
```

-continued

```
tgtgaaggca agcgaatctc ataaaggacg tctcagttcg gattgaagtc tgcaacccga    1320
cttcatgaag ctggaatcgc tagtaatcgc gaatcagcat gtcgcggtga atacgttctc    1380
gggcnttgta cacaccgccc gtcaaaccat gggagttggt aatgcccgaa gccggtggca    1440
taacctttcg aggagtgagc cgtcgaaggc aggaccgatg actgggg                  1487
```

<210> SEQ ID NO 15
<211> LENGTH: 1439
<212> TYPE: DNA
<213> ORGANISM: Acidaminococcus intestini

<400> SEQUENCE: 15

```
gcggagactt atttcggtaa gttcttagtg gcgaacgggt gagtaacgcg tgggcaacct     60 gcccctccagt tggggacaac attccgaaag ggatgctaat accgaatgtg ctccctcctc   120
cgcatggagg agggaggaaa gatggcctct gcttgcaagc tatcgctgga agatgggccc   180
gcgtctgatt agctagttgg tgggtaacg gctcaccaag gcgatgatca gtagccggtc    240
tgagaggatg aacggccaca ttgggactga gacacggccc aaactcctac gggaggcagc   300
agtggggaat cttccgcaat ggacgaaagt ctgacggagc aacgccgcgt gagtgatgaa   360
ggtcttcgga ttgtaaaact ctgttgttag ggacgaaagc accgtgttcg aacaggtcat   420
ggtgttgacg gtacctaacg aggaagccac ggctaactac gtgccagcag ccgcggtaat   480
acgtaggtgg caagcgttgt ccggaattat tgggcgtaaa gagcatgtag gcgggctttt   540
aagtctgacg tgaaaatgcg gggcttaacc ccgtatggcg ttggatactg aagtcttga    600 gtgcaggaga ggaaagggga attcccagtg tagcggtgaa atgcgtagat attgggagga   660
acaccagtgg cgaaggcgcc tttctggact gtgtctgacg ctgagatgcg aaagccaggg   720
tagcaaacgg gattagatac cccggtagtc ctggccgtaa acgatggata ctaggtgtag   780
gaggtatcga cccttctgt gccggagtta acgcaataag tatcccgcct ggggactacg   840
atcgcaagat tgaaactcaa aggaattgac ggggccccgc acaagcggtg gagtatgtgg   900
tttaattcga cgcaacgcga agaaccttac caaggcttga cattgagtga agacctaga   960 gataggtccc tcccttcggg gacacgaaaa caggtggtgc atggctgtcg tcagctcgtg   1020
tcgtgagatg ttgggttaag tcccgcaacg agcgcaaccc ctatcctatg ttaccagcgc   1080
gtaatggcgg ggactcatag gagactgcca gggataactt ggaggaaggc ggggatgacg   1140
tcaagtcatc atgccccctta tgtcttgggc tacacacgta ctacaatggt cggcaacaaa   1200
gggcagcgaa accgcgaggt ggagcaaatc ccagaaaccc gacccagtt cggatcgtag   1260 gctgcaaccc gcctacagtg aagttggaat cgctagtaat cgcaggtcag catactgcgg   1320
tgaatacgtt cccgggcctt gtacacaccg cccgtcacac cacgaaagtt ggtaacaccc   1380
gaagccggtg agataacctt ttaggagtca gctgtctaag gtggggccga tgattgggg   1439
```

<210> SEQ ID NO 16
<211> LENGTH: 1493
<212> TYPE: DNA
<213> ORGANISM: Clostridium glycyrrhizinilyticum
<220> FEATURE:
<221> NAME/KEY: misc_feature
<222> LOCATION: (207)..(207)
<223> OTHER INFORMATION: n is a, c, g, or t

<400> SEQUENCE: 16

```
agagtttgat cctggctcag gatgaacgct ggcggcgtgc ttaacacatg caagtcgaac     60
gaagcacttt accggatttc ttcggaatga aagttttgtg actgagtggc ggacgggtga   120
```

```
gtaacgcgtg ggtaacctgc ctcatacagg gggataacag ttagaaatga ctgctaatac      180
cgcataagac cacaggaccg catggtncgg tggtaaaaac tccggtggta tgagatggac      240
ccgcgtctga ttagctagtt ggtaaggtaa cggcttacca aggcgacgat cagtagccga      300
cctgagaggg tgaccggcca cattgggact gagacacggc ccaaactcct acgggaggca      360
gcagtgggga atattgcaca atgggggaaa ccctgatgca gcgacgccgc gtgagcgatg      420
aagtatttcg gtatgtaaag ctctatcagc agggaagaat taggacggta cctgactaag      480
aagcaccggc taaatacgtg ccagcagccg cggtaatacg tatggtgcaa gcgttatccg      540
gatttactgg gtgtaaaggg agcgtagacg gagaggcaag tctgatgtga aacccgggg      600 ctcaaccccg ggactgcatt ggaaactgtt tttctagagt gtcggagagg taagtggaat      660
tcctagtgta gcggtgaaat gcgtagatat taggaggaac accagtggcg aaggcggctt      720
actggacgat gactgacgtt gaggctcgaa agcgtgggga gcaaacagga ttagataccc      780
tggtagtcca cgccgtaaac gatgactgct aggtgtcggg aggcaaagcc tttcggtgcc      840
gcagcaaacg caataagcag tccacctggg gagtacgttc gcaagaatga aactcaaagg      900
aattgacggg gacccgcaca gcggtggag catgtggttt aattcgaagc aacgcgaaga      960
accttacctg cccttgacat ccggctgacc ggcgagtaat gtcgccttc cttcgggaca     1020 gccgagacag gtggtgcatg gttgtcgtca gctcgtgtcg tgagatgttg ggttaagtcc     1080
cgcaacgagc gcaacccctta tctttagtag ccagcatttc ggatgggcac tctagagaga     1140
ctgccaggga taacctggag gaaggtgggg atgacgtcaa atcatcatgc cccttatggg     1200
cagggctaca cacgtgctac aatggcgtaa acaaagggag gcaagcctgc gagggtgagc     1260
aaatcccaaa aataacgtct cagttcggat tgtagtctgc aactcgacta catgaagctg     1320
gaatcgctag taatcgcgaa tcagaatgtc gcggtgaata cgttcccggg tcttgtacac     1380
accgcccgtc acaccatggg agttggtaac gcccgaagtc agtgacccaa ccgtaaggag     1440
ggagctgccg aaggtgggac cgataactgg ggtgaagtcg taacaaggta acc            1493

<210> SEQ ID NO 17
<211> LENGTH: 1553
<212> TYPE: DNA
<213> ORGANISM: Desulfosporosinus lacus

<400> SEQUENCE: 17
gatcctggct caggacgaac gctggcggcg tgcctaacac atgcaagtcg aacggagaat       60
ttcaataagt ttacttagag aagttttttag tggcggacgg gtgagtaacg cgtgggtaac      120
ctacccataa agccgggaca accttggaa acgagggcta ataccggata atctttgatg       180
ttggcatcaa ggttaaagga aaggtggcct ctgaagatgc taccgattat ggatggaccc      240
gcgtctgatt agctagttgg tggggtaaag gcctaccaag gcgacgatca gtagccggcc      300 tgagagggt aacggccaca ctgggactga gacacgccc agactcctac gggaggcagc       360
agtggggaat cttccgcaat ggacgaaagt ctgacgagc aacgccgcgt gtatgatgaa      420
ggtcttcgga ttgtaaagta ctgtcttgg ggaagaatga ctgatttgaa atattgagt       480 cagtatgacg gtacccaagg aggaagcccc ggctaactac gtgccagcag ccgcggtaat      540
acgtaggggg caagcgttgt ccggaattat tgggcgtaaa gggcgcgtag gcggattttt      600
aagtctggtg tgaaagatca gggctcaacc ctgagagtgc atcggaaact ggagatcttg      660
aggacaggag aggaaagtgg aattccacgt gtagcggtga aatgcgtaga tatgtggagg      720
```

-continued

```
aacaccagtg gcgaaggcga ctttctggac tgtaactgac gctgaggcgc gaaagcgtgg    780
ggagcaaaca ggattagata ccctggtagt ccacgctgta aacgatgagt gctaggtgta    840
gagggtatcg acccettctg tgccgcagtt aacacaataa gcactccgcc tggggagtac    900
ggccgcaagg ttgaaactca aaggaattga cgggggcccg cacaagcggt ggagcatgtg    960
gtttaattcg acgcaacgcg aagaacctta ccaaggcttg acatccacag aatcctaagg   1020
aaacttggga gtgcccttcg gggagctgtg agacaggtgg tgcatggttg tcgtcagctc   1080
gtgtcgtgag atgttgggtt aagtcccgca acgagcgcaa ccctgtgtt tagttgctaa    1140 cgcgtaatgg cgagcactct agacagactg ccggtgataa accggaggaa ggtggggatg   1200
acgtcaaatc atcatgcccc ttatgtcttg ggctacacac gtgctacaat ggccggtaca   1260
gacggaagcg aagccgcgag gtgaagccaa tcccgagaaag ccggtctcag ttcggattgc  1320
aggctgcaac tcgcctgcat gaagtcggaa tcgctagtaa tcgcaggtca gcatactgcg   1380
gtgaatacgt tcccgggcct tgtacacacc gcccgtcaca ccacgaaagt ctgcaacacc   1440
cgaagccggt gaggtaaccc gaaagggagc tagccgtcga aggtggggcc gatgattggg   1500
gtgaagtcgt aacaaggtag ccgtatcgga aggtgcggct ggatcacctc ctt          1553
```